(12) United States Patent
Ikeda et al.

(10) Patent No.: US 8,703,922 B2
(45) Date of Patent: Apr. 22, 2014

(54) LOW-VISCOSITY LIQUID CRYSTAL COMPOUND

(75) Inventors: Yutaka Ikeda, Tokyo (JP); Jun Yamashita, Tokyo (JP); Ichiro Hijikuro, Tokyo (JP); Satoshi Imuta, Tokyo (JP); Yasuhiro Hiroki, Tokyo (JP); Takashi Takahashi, Tokyo (JP)

(73) Assignee: Chemgenesis Incorporated (JP)

( * ) Notice: Subject to any disclaimer, the term of this patent is extended or adjusted under 35 U.S.C. 154(b) by 0 days.

(21) Appl. No.: 13/518,932

(22) PCT Filed: Dec. 27, 2010

(86) PCT No.: PCT/JP2010/073621
§ 371 (c)(1),
(2), (4) Date: Jun. 25, 2012

(87) PCT Pub. No.: WO2011/078383
PCT Pub. Date: Jun. 30, 2011

(65) Prior Publication Data
US 2012/0264923 A1    Oct. 18, 2012

(30) Foreign Application Priority Data

Dec. 25, 2009  (JP) .................. 2009-295658

(51) Int. Cl.
| | | |
|---|---|---|
| *C07H 15/00* | (2006.01) | |
| *C07H 15/04* | (2006.01) | |
| *A61K 31/70* | (2006.01) | |
| *A61K 31/7028* | (2006.01) | |
| *C07C 57/03* | (2006.01) | |

(52) U.S. Cl.
USPC .............................. 536/4.1; 514/25; 554/223

(58) Field of Classification Search
USPC ................. 536/4.1; 514/25; 554/223
See application file for complete search history.

(56) References Cited

U.S. PATENT DOCUMENTS

2008/0113923 A1   5/2008   Hatoh et al.
2010/0279934 A1   11/2010  Lindahl

FOREIGN PATENT DOCUMENTS

| JP | 60028945 | * | 2/1985 |
|---|---|---|---|
| JP | 60028946 | | 2/1985 |
| WO | WO 2006/043705 | | 4/2006 |
| WO | WO 2009/087485 | | 7/2009 |

OTHER PUBLICATIONS

STN abstract of Kao Corp.; JP 60028945; Feb. 14, 1985.*
Barauskas, Justas, et al., "Phase Behavior of the Phyantriol/Water System", Langmuir, vol. 19, No. 23, 2003, pp. 9562-9565.

* cited by examiner

*Primary Examiner* — Shaojia Anna Jiang
*Assistant Examiner* — Michael C Henry
(74) *Attorney, Agent, or Firm* — McCarter & English

(57) ABSTRACT

The present invention relates to a liquid crystal compound that can be used as a base for injection formulations. The present invention provides an amphipathic compound having the following general formula (I):

(I)

$$R-O-\underset{X\ Y}{\overset{}{C}}-(CH_2)_n-CH=CH-(CH_2)_m-CH(CH_3)_2$$

wherein X and Y each denotes a hydrogen atom or together denote an oxygen atom, n denotes an integer from 0 to 2, m denotes the integer 1 or 2, and R denotes a hydrophilic group generated by removal of one hydroxyl group from any one selected from the group consisting of glycerol, erythritol, pentaerythritol, diglycerol, triglycerol, xylose, sorbitol, ascorbic acid, glucose, galactose, mannose, dipentaerythritol, maltose, mannitol, and xylitol; as well as a base for injection formulations and depot formulation comprising the same.

10 Claims, 2 Drawing Sheets

LOW-VISCOSITY LIQUID CRYSTAL COMPOUND

RELATED APPLICATIONS

This application is a national stage application filed under 35 USC §371 of PCT/JP2010/073621, filed Dec. 27, 2010, which claims the benefit of Japanese Patent Application No. 2009-295658, filed Dec. 25, 2009, both of which are incorporated herein, in entirety, by reference.

TECHNICAL FIELD

The present invention relates to a liquid crystal compound useful as a base for injection formulations.

BACKGROUND ART

Amphipathic compounds having both hydrophilic and hydrophobic groups within the same molecules spontaneously form various shapes of molecular assemblies in water. Amphipathic compounds form various molecular assemblies in water at the Krafft temperature (TK; referred to as Krafft eutectic temperature, Krafft point, or the like) or higher, as determined depending on the types or concentrations thereof (Non-patent Document 1). Examples of such molecular clusters include closed micelles (e.g., spherical micells and rod micells) with hydrophilic groups oriented outward, closed reversed micelles with hydrophobic groups oriented outward, sponge phases wherein hydrophobic groups or hydrophilic groups of amphipathic compounds are aligned facing each other in bilayer membranes and the bilayer membranes are randomly connected, and various lyotropic liquid crystal phases. Known examples of the lyotropic liquid crystal phase include hexagonal liquid crystal and reverse hexagonal liquid crystal wherein infinitely long cylindrical clusters form a two-dimensional hexagonal lattice, lamellar liquid crystal wherein bilayer membrane sheets are layered at regular intervals in the direction of the Z axis, and cubic liquid crystal having a three-dimensional lattice structure. Amphipathic compounds forming liquid crystal are referred to as liquid crystal compounds.

These molecular clusters, and amphipathic compounds forming liquid crystal in particular, are used for various applications in the fields of cosmetics, pharmaceutical products, and the like. For example, drug delivery systems (DDS) using amphipathic compounds are under active development. Various forms of drug delivery carriers have been produced, including a drug delivery system (Non-patent Document 2) in which a drug is embedded in an intraliposomal aqueous phase or a lipid bilayer prepared from lamellar liquid crystal (Patent Documents 1 and 2). In particular, non-lamellar liquid crystal such as cubic liquid crystal or reverse hexagonal liquid crystal has a high degree of structural stability and is capable of stably retaining various drugs within itself, and thus is attracting attention as a particularly useful drug delivery carrier.

Meanwhile, most forms of cubic liquid crystal found in an amphipathic compound/water system can remain stable only within a narrow concentration range between other phase regions, such as an aqueous micelle solution, hexagonal liquid crystal, lamellar liquid crystal, and reverse hexagonal liquid crystal, which occupy large areas on a two-component (amphipathic compound/water) phase diagram (Non-patent Document 3). Thus, the cubic liquid crystal is used with difficulty as a drug delivery carrier or the like. In recent years, it has been reported that monoacylglycerols including monoolein and phytantriols form "type II cubic crystal" wherein a cubic phase and an aqueous phase are adjacent to each other on a two-component (amphipathic compound/water) phase diagram. It has also been reported that the liquid crystal is relatively stable even when it coexists with excess water. Thus, application of the liquid crystal to a drug delivery system or the like has been attempted (Non-patent Document 4). However, liquid crystal formed by monoolein and the like has low stability at low temperatures. Accordingly, an amphipathic compound capable of forming cubic liquid crystal that exhibits high stability at low temperatures (less than 6° C.) has been developed and the use of the liquid crystal in a sustained release formulation has also been disclosed (Patent Document 3).

However, such liquid crystal compounds stably forming cubic liquid crystal have high viscosity and thus do not allow the compounds to pass through a thin injection needle (e.g., 30 gauge). Hence, these liquid crystal compounds are problematic in that they are used with difficulty as bases for injection formulations.

REFERENCES

Patent Documents

Patent Document 1: JP Patent Publication (Kohyo) No. 2002-505307 A

Patent Document 2: JP Patent Publication (Kokai) No. 2001-231845 A

Patent Document 3: International Patent Publication WO2006/043705

Non-Patent Documents

Non-Patent Document 1: Laughlin, R. G., "The Aqueous Phase Behavior of Surfactants" (1994) Academic Press London, p. 106-117

Non-Patent Document 2: Lasic D. D., TIBTECH 16, (1998) p. 307-321

Non-Patent Document 3: Fontell, K. Colloid & Polymer Sci., 268 (1990) p. 264-285

Non-Patent Document 4: Barauskas, J., Landh, T., Langmuir, (2003) 19, p. 9562-9565

DISCLOSURE OF THE INVENTION

Problem to be Solved by the Invention

An object of the present invention is to provide a liquid crystal compound that can be used as a base for injection formulations.

Means for Solving the Problem

As a result of intensive studies to achieve the above object, the present inventors have found that an amphipathic compound having a predetermined general formula, in which long chain unsaturated hydrocarbon is linked to polyhydric alcohol via ester, ether, or glycosidic linkage, has particularly low viscosity, and is capable of forming type II (water-in-oil) non-lamellar liquid crystal useful as a drug delivery carrier in an aqueous medium. Thus, the present inventors have completed the present invention.

The present invention encompasses the following (1) to (3).

[1] An amphipathic compound having the following general formula (I):

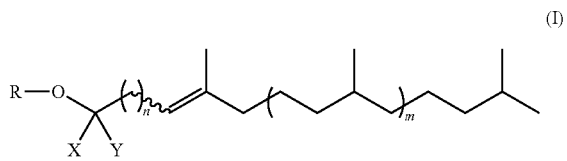

wherein X and Y each denotes a hydrogen atom or together denote an oxygen atom, n denotes an integer from 0 to 2, m denotes the integer 1 or 2, and R denotes a hydrophilic group generated by removal of one hydroxyl group from any one selected from the group consisting of glycerol, erythritol, pentaerythritol, diglycerol, triglycerol, xylose, sorbitol, ascorbic acid, glucose, galactose, mannose, dipentaerythritol, maltose, mannitol, and xylitol.

This amphipathic compound has preferably viscosity of 11.0 Pa·s or less as determined at 25° C.

This amphipathic compound has more preferably viscosity of 4.0 Pa·s or less as determined at 25° C.

In one embodiment, preferred examples of the amphipathic compound include the following compounds:
1) mono-O-(5,9,13,17-tetramethyloctadec-4-enoyl)pentaerythritol,
2) mono-O-(5,9,13,17-tetramethyloctadec-4-enoyl)erythritol,
3) mono-O-(5,9,13,17-tetramethyloctadec-4-enoyl)glycerol,
4) mono-O-(5,9,13,17-tetramethyloctadec-4-enoyl)diglycerol,
5) 1-O-(5,9,13,17-tetramethyloctadec-4-enyl)-D-xylopyranoside,
6) mono-O-(5,9,13,17-tetramethyloctadec-4-enyl)pentaerythritol,
7) mono-O-(5,9,13,17-tetramethyloctadec-4-enyl)glycerol,
8) mono-O-(5,9,13,17-tetramethyloctadec-4-enyl)erythritol,
9) mono-O-(5,9,13,17-tetramethyloctadec-4-enyl)diglycerol,
10) mono-O-(3,7,11,15-tetramethylhexadec-2-enoyl)glycerol,
11) mono-O-(3,7,11,15-tetramethylhexadec-2-enoyl)erythritol,
12) mono-O-(3,7,11,15-tetramethylhexadec-2-enoyl)pentaerythritol,
13) mono-O-(3,7,11,15-tetramethylhexadec-2-enoyl)diglycerol,
14) 1-O-(3,7,11,15-tetramethylhexadec-2-enyl)-D-xylopyranoside,
15) mono-O-(3,7,11,15-tetramethylhexadec-2-enyl)glycerol,
16) mono-O-(3,7,11,15-tetramethylhexadec-2-enyl)erythritol,
17) mono-O-(3,7,11,15-tetramethylhexadec-2-enyl)pentaerythritol,
18) mono-O-(3,7,11,15-tetramethylhexadec-2-enyl)diglycerol,
19) mono-O-(5,9,13-trimethyltetradec-4-enoyl)glycerol,
20) mono-O-(5,9,13-trimethyltetradec-4-enoyl)erythritol,
21) mono-O-(5,9,13-trimethyltetradec-4-enoyl)pentaerythritol,
22) mono-O-(5,9,13-trimethyltetradec-4-enoyl)diglycerol,
23) 1-O-(5,9,13-trimethyltetradec-4-enyl)-D-xylopyranoside,
24) mono-O-(5,9,13-trimethyltetradec-4-enyl)glycerol,
25) mono-O-(5,9,13-trimethyltetradec-4-enyl)erythritol,
26) mono-O-(5,9,13-trimethyltetradec-4-enyl)pentaerythritol,
27) mono-O-(5,9,13-trimethyltetradec-4-enyl)diglycerol,
28) mono-O-(3,7,11-trimethyldodec-2-enoyl)glycerol,
29) mono-O-(3,7,11-trimethyldodec-2-enoyl)erythritol,
30) mono-O-(3,7,11-trimethyldodec-2-enoyl)pentaerythritol,
31) mono-O-(3,7,11-trimethyldodec-2-enoyl)diglycerol,
32) 1-O-(3,7,11-trimethyldodec-2-enyl)-D-xylopyranoside,
33) mono-O-(3,7,11-trimethyldodec-2-enyl)glycerol,
34) mono-O-(3,7,11-trimethyldodec-2-enyl)erythritol,
35) mono-O-(3,7,11-trimethyldodec-2-enyl)pentaerythritol, and
36) mono-O-(3,7,11-trimethyldodec-2-enyl)diglycerol.

In another embodiment, particularly preferable examples of the amphipathic compound include the following compounds:
(1) mono-O-(5,9,13,17-tetramethyloctadec-4-enoyl)pentaerythritol,
(2) mono-O-(5,9,13,17-tetramethyloctadec-4-enoyl)erythritol,
(3) mono-O-(5,9,13,17-tetramethyloctadec-4-enoyl)glycerol,
(4) mono-O-(5,9,13,17-tetramethyloctadec-4-enoyl)diglycerol,
(5) mono-O-(5,9,13,17-tetramethyloctadec-4-enoyl)triglycerol,
(6) mono-O-(5,9,13,17-tetramethyloctadec-4-enoyl)sorbitol,
(7) 1-O-(5,9,13,17-tetramethyloctadec-4-enyl)-D-xylopyranoside,
(8) mono-O-(5,9,13,17-tetramethyloctadec-4-enyl)pentaerythritol, and
(9) mono-O-(5,9,13,17-tetramethyloctadec-4-enyl)erythritol.

[2] A base for an injection formulation, which comprises at least one type of the compound of [1] above.

This base is more preferably a base for a depot formulation.

[3] A depot formulation, which comprises the base for depot formulations of [2] above.

Effects of the Invention

The amphipathic compound according to the present invention exhibits significantly low viscosity. Hence, an injection formulation having viscosity that enables injection can be easily prepared by adding a drug to the amphipathic compound according to the present invention. Also, the amphipathic compound according to the present invention can retain a drug by forming non-lamellar liquid crystal in an aqueous solvent. Therefore, the amphipathic compound according to the present invention is administered in vivo, so that it forms non-lamellar liquid crystal in a body fluid so as to be able to retain a drug.

EMBODIMENTS FOR CARRYING OUT THE INVENTION

Figure 1:
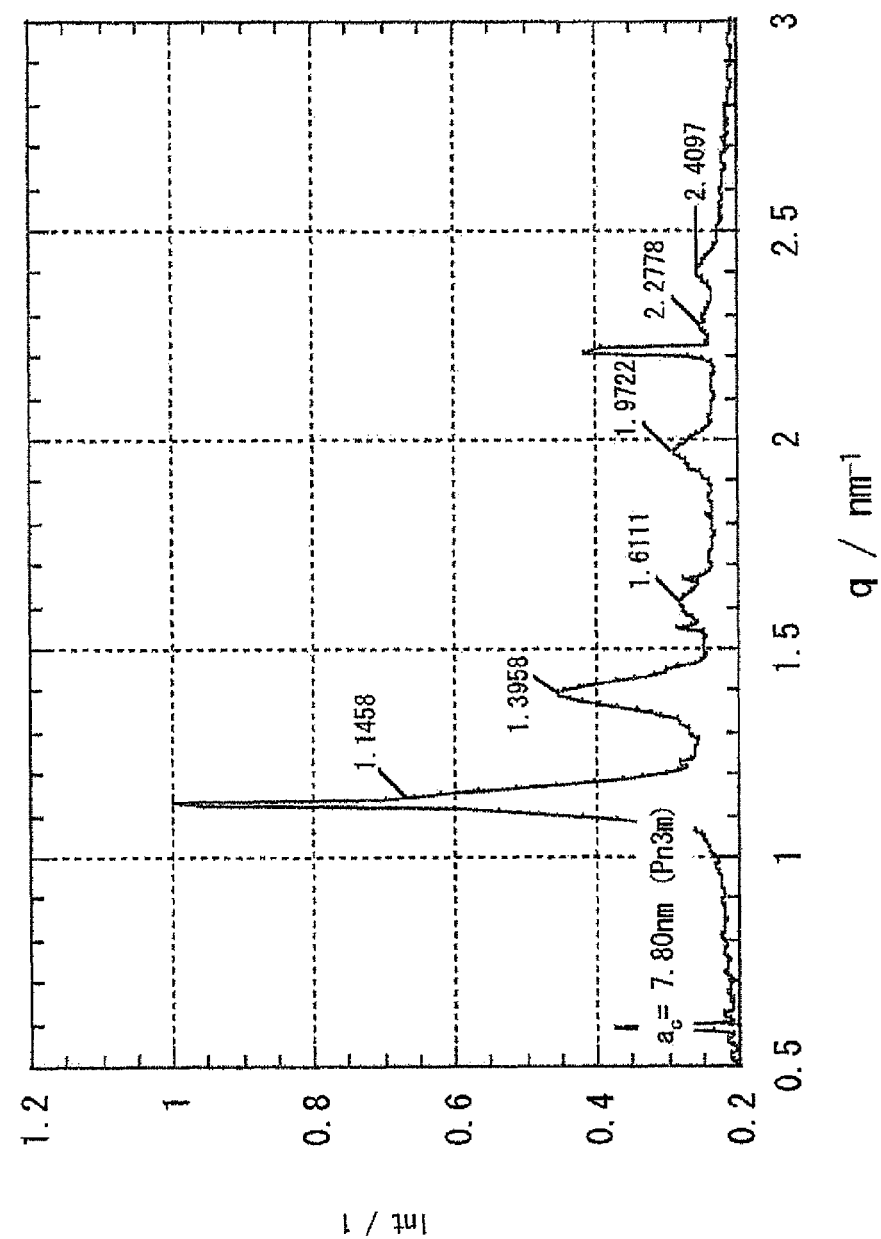
FIG. 1 shows a scattering curve showing the results of the SAXS analysis (small-angle scattering measurement) of a mono-O-(5,9,13,17-tetramethyloctadec-4-enoyl)pentaerythritol/water system sample. The scattering curve was plotted against scattering vector length $q=(4\pi/\lambda)\sin(\theta/2)$, wherein $\theta$ denotes scattering angle. The vertical axis indicates relative intensity compared to the intensity of direct beam attenuated by a semi-transparent beam stopper having a base index of 1.

The present invention is described in detail as follows.
1. Amphipathic Compound The amphipathic compound according to the present invention is a compound having the following general formula (I):

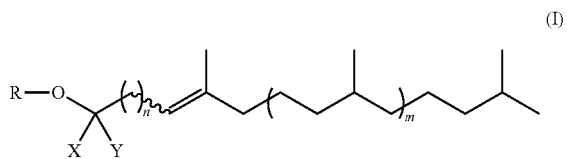

(I)

In the above formula (I), X and Y each denotes a hydrogen atom or together denote an oxygen atom, n denotes an integer from 0 to 2, m denotes the integer 1 or 2, or R denotes a hydrophilic group.

The hydrophilic group R is preferably, but not limited to, a residue that is generated by removal of one hydroxyl group from any one selected from the group consisting of glycerol, erythritol, pentaerythritol, diglycerol, triglycerol, xylose, xylitol, mannitol, sorbitol, ascorbic acid, glucose, galactose, mannose, dipentaerythritol, and maltose.

In addition, the designation in the above formula: ⌇ means that the amphipathic compound according to the present invention is an E-(cis-) or Z-(trans-)geometric isomer, or a mixture thereof.

The amphipathic compound names with prefix "mono" as used herein are, if two or more positional isomers are present, generally mean each of corresponding positional isomers and a mixture thereof. For example, when hydrophilic group R above is a glycerol, an erythritol, or a diglycerol residue, the corresponding amphipathic compound names with prefix "mono" according to the present invention generally mean a 1-ester, a 2-ester, and a mixture thereof; or a 1-ether, a 2-ether, and a mixture thereof. Specific examples thereof are compounds (2) and (5) described later and their meanings are as explained concerning positional isomers. Similarly, when hydrophilic group R is a xylitol, a mannitol, or a sorbitol residue, the corresponding amphipathic compound names with prefix "mono" according to the present invention generally mean 1- to 3-esters and a mixture of two or more of these esters; or 1- to 3-ethers and a mixture of two or more of these ethers. When hydrophilic group R is an ascorbic acid residue, the corresponding amphipathic compound names with prefix "mono" according to the present invention generally mean 2-, 3-, 5-, and 6-esters and a mixture of two or more of these esters; or 2-, 3-, 5-, and 6-ethers and a mixture of two or more of these ethers.

In the above formula of the amphipathic compound of the present invention, "n" may be an integer from 0 to 2, and n=0 or 2 is more preferable, and n=2 is even more preferable. Similarly, in the above formula, "m" may be the integer 1 or 2, and m=2 is more preferable.

In the amphipathic compound of the present invention, a hydrophobic hydrocarbon chain may have a carbon number of C15, C16, or C17 (wherein m=1, n=0, 1, or 2) or C20, C21, or C22 (wherein m=2, n=0, 1, or 2).

One embodiment of the amphipathic compound of the present invention is preferably a compound defined with n=2 and m=2 in the above formula. Specifically, such compound is one having the above formula in which the hydrophilic group R is bound to the hydrophobic hydrocarbon chain being 5,9,13,17-tetramethyloctadec-4-enoyl or 5,9,13,17-tetramethyloctadec-4-enyl, via ester bond or ether bond, respectively. Specific examples of the compound include the following compounds.

(1) mono-O-(5,9,13,17-tetramethyloctadec-4-enoyl)pentaerythritol
(2) mono-O-(5,9,13,17-tetramethyloctadec-4-enoyl)erythritol
 Herein, "mono-O-(5,9,13,17-tetramethyloctadec-4-enoyl)erythritol" includes two positional isomers, 1-O-(5,9,13,17-tetramethyloctadec-4-enoyl)erythritol (that is, 1-ester) and 2-O-(5,9,13,17-tetramethyloctadec-4-enoyl)erythritol (that is, 2-ester), and a mixture thereof.
(3) 1-O-(5,9,13,17-tetramethyl octadec-4-enyl)-D-xylopyranoside
(4) mono-O-(5,9,13,17-tetramethyloctadec-4-enyl)pentaerythritol
(5) mono-O-(5,9,13,17-tetramethyloctadec-4-enyl)erythritol
 Herein, "mono-O-(5,9,13,17-tetramethyloctadec-4-enyl)erythritol" includes two positional isomers, 1-O-(5,9,13,17-tetramethyloctadec-4-enyl)erythritol (that is, 1-ether) and 2-O-(5,9,13,17-tetramethyloctadec-4-enyl)erythritol (that is, 2-ether), and a mixture thereof.
(6) mono-O-(5,9,13,17-tetramethyloctadec-4-enoyl)glycerol
(7) mono-O-(5,9,13,17-tetramethyloctadec-4-enoyl)diglycerol
(8) mono-O-(5,9,13,17-tetramethyloctadec-4-enoyl)triglycerol
(9) mono-O-(5,9,13,17-tetramethyloctadec-4-enoyl)xylitol
(10) mono-O-(5,9,13,17-tetramethyloctadec-4-enoyl)mannitol
(11) mono-O-(5,9,13,17-tetramethyloctadec-4-enoyl)sorbitol
(12) mono-O-(5,9,13,17-tetramethyloctadec-4-enoyl)ascorbic acid
(13) mono-O-(5,9,13,17-tetramethyloctadec-4-enoyl)dipentaerythritol
(14) 1-O-(5,9,13,17-tetramethyloctadec-4-enyl)-D-glucoside
(15) 1-O-(5,9,13,17-tetramethyloctadec-4-enyl)-D-galactoside
(16) 1-O-(5,9,13,17-tetramethyloctadec-4-enyl)-D-mannoside
(17) 1-O-(5,9,13,17-tetramethyloctadec-4-enyl)-D-maltoside
(18) mono-O-(5,9,13,17-tetramethyloctadec-4-enyl)glycerol
(19) mono-O-(5,9,13,17-tetramethyloctadec-4-enyl)diglycerol
(20) mono-O-(5,9,13,17-tetramethyloctadec-4-enyl)triglycerol
(21) mono-O-(5,9,13,17-tetramethyloctadec-4-enyl)xylitol
(22) mono-O-(5,9,13,17-tetramethyloctadec-4-enyl)mannitol
(23) mono-O-(5,9,13,17-tetramethyloctadec-4-enyl)sorbitol

(24) mono-O-(5,9,13,17-tetramethyloctadec-4-enyl)ascorbic acid
(25) mono-O-(5,9,13,17-tetramethyloctadec-4-enyl)dipentaerythritol Herein, the meaning of the designation "mono" for the above compounds (6) to (12) and (18) to (24) is as described above.

Another preferred embodiment of the amphipathic compound of the present invention is a compound having the above formula wherein n=0 and m=2. The hydrophobic hydrocarbon chain of the compound may be from phytol. Specifically, the compound is one having the above formula in which the hydrophilic group R is bound to the hydrophobic hydrocarbon chain being 3,7,11,15-tetramethylhexadec-2-enoyl or 3,7,11,15-tetramethylhexadec-2-enyl, via ester bond or ether bond, respectively. Specific examples of the compound include the following compounds.

(26) mono-O-(3,7,11,15-tetramethylhexadec-2-enoyl)glycerol
(27) mono-O-(3,7,11,15-tetramethylhexadec-2-enoyl)erythritol
(28) mono-O-(3,7,11,15-tetramethylhexadec-2-enoyl)pentaerythritol
(29) mono-O-(3,7,11,15-tetramethylhexadec-2-enoyl)diglycerol
(30) mono-O-(3,7,11,15-tetramethylhexadec-2-enoyl)triglycerol
(31) mono-O-(3,7,11,15-tetramethylhexadec-2-enoyl)xylitol
(32) mono-O-(3,7,11,15-tetramethylhexadec-2-enoyl)mannitol
(33) mono-O-(3,7,11,15-tetramethylhexadec-2-enoyl)sorbitol
(34) mono-O-(3,7,11,15-tetramethylhexadec-2-enoyl)ascorbic acid
(35) mono-O-(3,7,11,15-tetramethylhexadec-2-enoyl)dipentaerythritol
(36) 1-O-(3,7,11,15-tetramethylhexadec-2-enyl)-D-xylopyranoside
(37) 1-O-(3,7,11,15-tetramethylhexadec-2-enyl)-D-glucoside
(38) 1-O-(3,7,11,15-tetramethylhexadec-2-enyl)-D-galactoside
(39) 1-O-(3,7,11,15-tetramethylhexadec-2-enyl)-D-mannoside
(40) 1-O-(3,7,11,15-tetramethylhexadec-2-enyl)-D-maltoside
(41) mono-O-(3,7,11,15-tetramethylhexadec-2-enyl)glycerol
(42) mono-O-(3,7,11,15-tetramethylhexadec-2-enyl)erythritol
(43) mono-O-(3,7,11,15-tetramethylhexadec-2-enyl)pentaerythritol
(44) mono-O-(3,7,11,15-tetramethylhexadec-2-enyl)diglycerol
(45) mono-O-(3,7,11,15-tetramethylhexadec-2-enyl)triglycerol
(46) mono-O-(3,7,11,15-tetramethylhexadec-2-enyl)xylitol
(47) mono-O-(3,7,11,15-tetramethylhexadec-2-enyl)mannitol
(48) mono-O-(3,7,11,15-tetramethylhexadec-2-enyl)sorbitol
(49) mono-O-(3,7,11,15-tetramethylhexadec-2-enyl)ascorbic acid
(50) mono-O-(3,7,11,15-tetramethylhexadec-2-enyl)dipentaerythritol Herein, the meaning of the designation "mono" for the above compounds (26), (27), (29) to (34), (41), (42), and (44) to (49) is as described above.

Another preferred embodiment of the amphipathic compound of the present invention is a compound having the above formula wherein n=2 and m=1. The hydrophobic hydrocarbon chain of the compound can be synthesized using geranylacetone as a starting material. Specifically, the compound is one having the above formula in which the hydrophilic group R is bound to the hydrophobic hydrocarbon chain being 5,9,13-trimethyltetradec-4-enoyl or 5,9,13-trimethyltetradec-4-enyl, via ester bond or ether bond, respectively. Specific examples of the compound include the following compounds.

(51) mono-O-(5,9,13-trimethyltetradec-4-enoyl)glycerol
(52) mono-O-(5,9,13-trimethyltetradec-4-enoyl)erythritol
(53) mono-O-(5,9,13-trimethyltetradec-4-enoyl)pentaerythritol
(54) mono-O-(5,9,13-trimethyltetradec-4-enoyl)diglycerol
(55) mono-O-(5,9,13-trimethyltetradec-4-enoyl)triglycerol
(56) mono-O-(5,9,13-trimethyltetradec-4-enoyl)xylitol
(57) mono-O-(5,9,13-trimethyltetradec-4-enoyl)mannitol
(58) mono-O-(5,9,13-trimethyltetradec-4-enoyl)sorbitol
(59) mono-O-(5,9,13-trimethyltetradec-4-enoyl)ascorbic acid
(60) mono-O-(5,9,13-trimethyltetradec-4-enoyl)dipentaerythritol
(61) 1-O-(5,9,13-trimethyltetradec-4-enyl)-D-xylopyranoside
(62) 1-O-(5,9,13-trimethyltetradec-4-enyl)-D-glucoside
(63) 1-O-(5,9,13-trimethyltetradec-4-enyl)-D-galactoside
(64) 1-O-(5,9,13-trimethyltetradec-4-enyl)-D-mannoside
(65) 1-O-(5,9,13-trimethyltetradec-4-enyl)-D-maltoside
(66) mono-O-(5,9,13-trimethyltetradec-4-enyl)glycerol
(67) mono-O-(5,9,13-trimethyltetradec-4-enyl)erythritol
(68) mono-O-(5,9,13-trimethyltetradec-4-enyl)pentaerythritol
(69) mono-O-(5,9,13-trimethyltetradec-4-enyl)diglycerol
(70) mono-O-(5,9,13-trimethyltetradec-4-enyl)triglycerol
(71) mono-O-(5,9,13-trimethyltetradec-4-enyl)xylitol
(72) mono-O-(5,9,13-trimethyltetradec-4-enyl)mannitol
(73) mono-O-(5,9,13-trimethyltetradec-4-enyl)sorbitol
(74) mono-O-(5,9,13-trimethyltetradec-4-enyl)ascorbic acid
(75) mono-O-(5,9,13-trimethyltetradec-4-enyl)dipentaerythritol Herein, the meaning of the designation "mono" for the above compounds (51), (52), (54) to (59), (66), (67), and (69) to (74) is as described above.

Another preferred embodiment of the amphipathic compound of the present invention is a compound having the above formula wherein n=0 and m=1. The hydrophobic hydrocarbon chain of the compound may be from tetrahydro farnesol. Specifically, the compound is one having the above formula in which the hydrophilic group R is bound to the hydrophobic hydrocarbon chain being 3,7,11-trimethyldodec-2-enoyl or 3,7,11-trimethyldodec-2-enyl, via ester bond or ether bond, respectively. Specific examples of the compound include the following compounds.

(76) mono-O-(3,7,11-trimethyldodec-2-enoyl)glycerol
(77) mono-O-(3,7,11-trimethyldodec-2-enoyl)erythritol
(78) mono-O-(3,7,11-trimethyldodec-2-enoyl)pentaerythritol
(79) mono-O-(3,7,11-trimethyldodec-2-enoyl)diglycerol
(80) mono-O-(3,7,11-trimethyldodec-2-enoyl)triglycerol
(81) mono-O-(3,7,11-trimethyldodec-2-enoyl)xylitol
(82) mono-O-(3,7,11-trimethyldodec-2-enoyl)mannitol
(83) mono-O-(3,7,11-trimethyldodec-2-enoyl)sorbitol

(84) mono-O-(3,7,11-trimethyldodec-2-enoyl)ascorbic acid
(85) mono-O-(3,7,11-trimethyldodec-2-enoyl)dipentaerythritol
(86) 1-O-(3,7,11-trimethyldodec-2-enyl)-D-xylopyranoside
(87) 1-O-(3,7,11-trimethyldodec-2-enyl)-D-glucoside
(88) 1-O-(3,7,11-trimethyldodec-2-enyl)-D-galactoside
(89) 1-O-(3,7,11-trimethyldodec-2-enyl)-D-mannoside
(90) 1-O-(3,7,11-trimethyldodec-2-enyl)-D-maltoside
(91) mono-O-(3,7,11-trimethyldodec-2-enyl)glycerol
(92) mono-O-(3,7,11-trimethyldodec-2-enyl)erythritol
(93) mono-O-(3,7,11-trimethyldodec-2-enyl)pentaerythritol
(94) mono-O-(3,7,11-trimethyldodec-2-enyl)diglycerol
(95) mono-O-(3,7,11-trimethyldodec-2-enyl)triglycerol
(96) mono-O-(3,7,11-trimethyldodec-2-enyl)xylitol
(97) mono-O-(3,7,11-trimethyldodec-2-enyl)mannitol
(98) mono-O-(3,7,11-trimethyldodec-2-enyl)sorbitol
(99) mono-O-(3,7,11-trimethyldodec-2-enyl)ascorbic acid
(100) mono-O-(3,7,11-trimethyldodec-2-enyl)dipentaerythritol Herein, the meaning of the designation "mono" for the above compounds (76), (77), (79) to (84), (91), (92), and (94) to (99) is as described above.

Another preferred embodiment of the amphipathic compound of the present invention is a compound having the above formula wherein n=1 and The hydrophobic hydrocarbon chain of the compound may be from phytol. Specifically, the compound is one having the above formula in which the hydrophilic group R is bound to the hydrophobic hydrocarbon chain being 4,8,12,16-tetramethylheptadec-3-enoyl or 4,8,12,16-tetramethylheptadec-3-enyl, via ester bond or ether bond, respectively. Specific examples of the compound include the following compounds.

(101) mono-O-(4,8,12,16-tetramethylheptadec-3-enoyl)glycerol
(102) mono-O-(4,8,12,16-tetramethylheptadec-3-enoyl)erythritol
(103) mono-O-(4,8,12,16-tetramethylheptadec-3-enoyl)pentaerythritol
(104) mono-O-(4,8,12,16-tetramethylheptadec-3-enoyl)diglycerol
(105) mono-O-(4,8,12,16-tetramethylheptadec-3-enoyl)triglycerol
(106) mono-O-(4,8,12,16-tetramethylheptadec-3-enoyl)xylitol
(107) mono-O-(4,8,12,16-tetramethylheptadec-3-enoyl)mannitol
(108) mono-O-(4,8,12,16-tetramethylheptadec-3-enoyl)sorbitol
(109) mono-O-(4,8,12,16-tetramethylheptadec-3-enoyl)ascorbic acid
(110) mono-O-(4,8,12,16-tetramethylheptadec-3-enoyl)dipentaerythritol
(111) 1-O-(4,8,12,16-tetramethylheptadec-3-enyl)-D-xylopyranoside
(112) 1-O-(4,8,12,16-tetramethylheptadec-3-enyl)-D-glucoside
(113) 1-O-(4,8,12,16-tetramethylheptadec-3-enyl)-D-galactoside
(114) 1-O-(4,8,12,16-tetramethylheptadec-3-enyl)-D-mannoside
(115) 1-O-(4,8,12,16-tetramethylheptadec-3-enyl)-D-maltoside
(116) mono-O-(4,8,12,16-tetramethylheptadec-3-enyl)glycerol
(117) mono-O-(4,8,12,16-tetramethylheptadec-3-enyl)erythritol
(118) mono-O-(4,8,12,16-tetramethylheptadec-3-enyl)pentaerythritol
(119) mono-O-(4,8,12,16-tetramethylheptadec-3-enyl)diglycerol
(120) mono-O-(4,8,12,16-tetramethylheptadec-3-enyl)triglycerol
(121) mono-O-(4,8,12,16-tetramethylheptadec-3-enyl)xylitol
(122) mono-O-(4,8,12,16-tetramethylheptadec-3-enyl)mannitol
(123) mono-O-(4,8,12,16-tetramethylheptadec-3-enyl)sorbitol
(124) mono-O-(4,8,12,16-tetramethylheptadec-3-enyl)ascorbic acid
(125) mono-O-(4,8,12,16-tetramethylheptadec-3-enyl)dipentaerythritol Herein, the meaning of the designation "mono" for the above compounds (101), (102), (104) to (109), (116), (117), and (119) to (124) is as described above.

Another preferred embodiment of the amphipathic compound of the present invention is a compound having the above formula wherein n=1 and m=1. The hydrophobic hydrocarbon chain of the compound may be from tetrahydro farnesol. Specifically, the compound is one having the above formula in which the hydrophilic group R is bound to the hydrophobic hydrocarbon chain being 4,8,12-trimethyltridec-3-enoyl or 4,8,12-trimethyltridec-3-enyl, via ester bond or ether bond, respectively. Specific examples of the compound include the following compounds.

(126) mono-O-(4,8,12-trimethyltridec-3-enoyl)glycerol
(127) mono-O-(4,8,12-trimethyltridec-3-enoyl)erythritol
(128) mono-O-(4,8,12-trimethyltridec-3-enoyl)pentaerythritol
(129) mono-O-(4,8,12-trimethyltridec-3-enoyl)diglycerol
(130) mono-O-(4,8,12-trimethyltridec-3-enoyl)triglycerol
(131) mono-O-(4,8,12-trimethyltridec-3-enoyl)xylitol
(132) mono-O-(4,8,12-trimethyltridec-3-enoyl)mannitol
(133) mono-O-(4,8,12-trimethyltridec-3-enoyl)sorbitol
(134) mono-O-(4,8,12-trimethyltridec-3-enoyl)ascorbic acid
(135) mono-O-(4,8,12-trimethyltridec-3-enoyl)dipentaerythritol
(136) 1-O-(4,8,12-trimethyltridec-3-enyl)-D-xylopyranoside
(137) 1-O-(4,8,12-trimethyltridec-3-enyl)-D-glucoside
(138) 1-O-(4,8,12-trimethyltridec-3-enyl)-D-galactoside
(139) 1-O-(4,8,12-trimethyltridec-3-enyl)-D-mannoside
(140) 1-O-(4,8,12-trimethyltridec-3-enyl)-D-maltoside
(141) mono-O-(4,8,12-trimethyltridec-3-enyl)glycerol
(142) mono-O-(4,8,12-trimethyltridec-3-enyl)erythritol
(143) mono-O-(4,8,12-trimethyltridec-3-enyl)pentaerythritol
(144) mono-O-(4,8,12-trimethyltridec-3-enyl)diglycerol
(145) mono-O-(4,8,12-trimethyltridec-3-enyl)triglycerol
(146) mono-O-(4,8,12-trimethyltridec-3-enyl)xylitol
(147) mono-O-(4,8,12-trimethyltridec-3-enyl)mannitol
(148) mono-O-(4,8,12-trimethyltridec-3-enyl)sorbitol
(149) mono-O-(4,8,12-trimethyltridec-3-enyl)ascorbic acid
(150) mono-O-(4,8,12-trimethyltridec-3-enyl)dipentaerythritol Herein, the meaning of the designation "mono" for the above compounds (126), (127), (129) to (134), (141), (142), and (144) to (149) is as described above.

The amphipathic compound according to the present invention is more generally an ether or ester compound, wherein one molecule of long chain unsaturated hydrocarbon, preferably, long chain unsaturated fatty acid or long chain unsaturated alcohol, is bound via an ether bond or an ester bond to one molecule of polyhydric alcohol (preferably, glycerol, erythritol, pentaerythritol, diglycerol, triglycerol, xylose, sorbitol, ascorbic acid, glucose, galactose, mannose, dipentaerythritol, or maltose).

The amphipathic compound according to the present invention can be synthesized in reference to the Examples described later. More generally, the amphipathic compound according to the present invention can be produced as described below, for example.

First, among compounds having the above general formula (I), an ester compound (the compound having the following general formula (I-1)) wherein X and Y together denote an oxygen atom can be produced by transesterification reaction between an ester compound having the following general formula (II) and a hydrophilic compound R—OH, for example. Reaction conditions for transesterification are not particularly limited, and transesterification is carried out using an acid or base catalyst, for example.

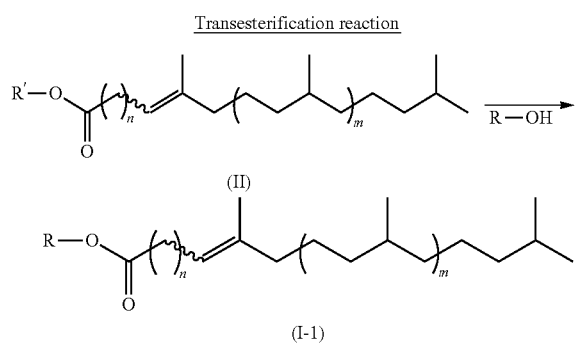

Furthermore, an ester compound (the compound having general formula (I-1)) can be produced by esterification between carboxylic acid corresponding to an ester compound having general formula (II) and a hydrophilic compound R—OH. Reaction conditions for esterification are not particularly limited and, for example, esterification is carried out using an acid or base catalyst or a condensing agent.

Some or all hydroxyl groups within R of a hydrophilic compound R—OH may be protected during transesterification or esterification reaction. In this case, an ester compound (I-1) can be produced by transesterification or esterification reaction followed by deprotection.

Second, among compounds having the above general formula (I), an ether compound (the compound having the following general formula (I-2)) wherein X and Y are both hydrogen atoms can be produced by etherification reaction between a compound having the following general formula (III) that has a leaving group Z and a hydrophilic compound R—OH, or by etherification reaction between an alcohol having the following general formula (IV) and a compound R—Z having a leaving group Z, for example. Reaction conditions for etherification are not particularly limited, and, for example, etherification is carried out using a base. Etherification reaction may also be carried out with protecting some or all hydroxyl groups within R of hydrophilic compound R—OH. In this case, the ether compound (I-2) can be produced by etherification reaction followed by deprotection.

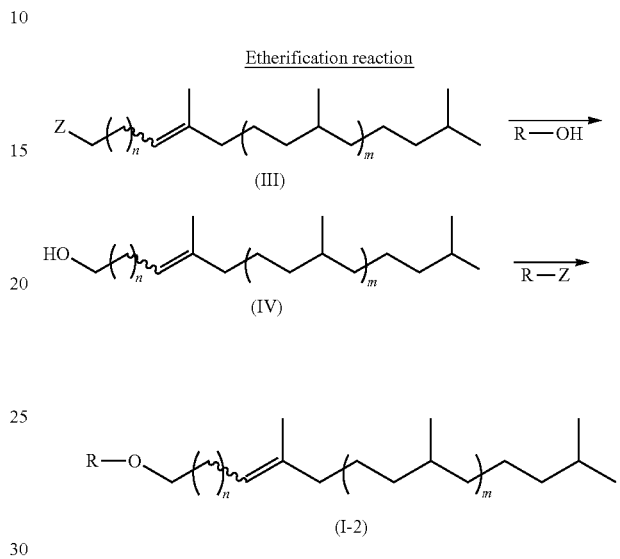

Third, among compounds having the above general formula (I), a glycoside compound having general formula (I-2), wherein X and Y are both hydrogen atoms and R is a sugar residue, can be produced by glycosylation reaction of an alcohol having general formula (IV) with saccharides R″—Z having a protected hydroxyl group and a leaving group Z at the anomeric position, followed by deprotection (R″→R). Reaction conditions for glycosylation are not particularly limited, and, for example, glycosylation is carried out using Lewis acids. Reaction conditions for deprotection are also not particularly limited, and, for example, deprotection is carried out by using elimination reaction conditions selected so that a glycosidic linkage is not impaired at a specific protecting group.

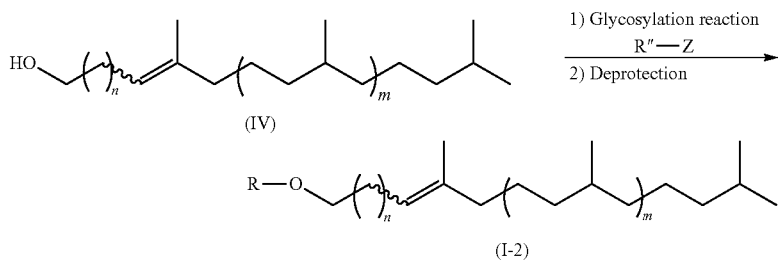

Compounds having the above general formulae (II), (III), and (IV) can be synthesized as described below, but, the synthesis method is not limited thereto.

An ester compound having the formula (II) wherein n=2 and m=2 can be obtained via Johnson-Claisen reaction using orthoacetate from isophytol, for example.

An ester compound having the above formula (II) wherein n=2 and m=1 can be obtained by Johnson-Claisen reaction using orthoacetate from 3,7,11-trimethyldodec-1-en-3-ol (tetrahydronerolidol), for example.

An ester compound having the formula (II) wherein n=1 and m=2 can be obtained by brominating the hydroxyl group of phytols and then causing a Grignard reagent generated by adding metal magnesium to react with carbon dioxide or carrying out substitution reaction with cyanide followed by hydrolysis to produce carboxylic acids, and then further carrying out esterification, for example.

An ester compound having the formula (II) wherein n=1 and m=1 can be obtained by brominating the hydroxyl group of 3,7,11-trimethyldodec-2-en-1-ol (tetrahydro farnesol) and then causing a Grignard reagent generated by adding metal magnesium to react with carbon dioxide or carrying out substitution reaction with cyanide followed by hydrolysis to produce carboxylic acids, and then further carrying out esterification, for example.

An ester compound having the formula (II) wherein n=0 and m=2 can be obtained by oxidizing phytols to produce carboxylic acids and then further carrying out esterification, for example.

An ester compound having the formula (II) wherein n=0 and m=1 can be obtained by oxidizing 3,7,11-trimethyldodec-2-en-1-ol (tetrahydro farnesol) to produce carboxylic acids and then further carrying out esterification, for example.

An alcohol having the formula (IV) wherein n=2 and m=2 can be obtained by reducing ester compounds having the formula (II) wherein n=2 and m=2 or the corresponding carboxylic acid using lithium aluminum hydride or the like. The alcohol having the formula (IV) wherein n=2 and m=1; n=1 and m=2; or n=1 and m=1 can be similarly obtained by reducing the ester compound having the formula (II) wherein n=2 and m=1; n=1 and m=2; or n=1 and m=1, respectively, or its corresponding carboxylic acid using lithium aluminum hydride or the like.

The alcohol having the formula (IV) wherein n=0 and m=2 is a phytol and is commercially available. However, the alcohol can also be obtained by reducing the ester compound having the formula (II) wherein n=0 and m=2 or its corresponding carboxylic acid using lithium aluminum hydride or the like, for example.

The alcohol having the formula (IV) wherein n=0 and m=1 is 3,7,11-trimethyldodec-2-en-1-ol (tetrahydro farnesol), and the compound can be obtained by reducing the ester compound having the formula (II) wherein n=0 and m=1 or its corresponding carboxylic acid using lithium aluminum hydride or the like, for example.

The compound having the formula (III) with the leaving group Z wherein n=2 and m=2 can be obtained by converting the alcohol having the formula (IV) wherein n=2 and m=2 to sulfonyloxy group (e.g., tosyl group or mesyl group) or a leaving group such as a halogen atom (e.g., a bromine atom or an iodine atom). The compound having the formula (III) with the leaving group Z wherein n=2, and m=1; n=1 and m=2; n=0 and m=2; or n=0 and m=1 can be similarly obtained by converting the alcohol having the formula (IV) wherein n=2 and m=1; n=1 and m=2; n=0 and m=2; or n=0 and m=1, respectively, to a leaving group.

The amphipathic compound according to the present invention may be any one of the above compounds (1) to (150) prepared by further substituting a hydrogen atom or a hydroxyl group with any substituent.

It is preferably verified that the thus synthesized compounds are compounds of interest, by using conventional methods such as infrared spectroscopy measurement or NMR measurement.

2. Viscosity of Amphipathic Compound

The amphipathic compound according to the present invention is in a liquid or a semi-solid state with low viscosity within relatively a wide temperature range. The amphipathic compound according to the present invention preferably has viscosity of 11 Pa·s or less, generally 10 Pa·s or less, more preferably 4.0 Pa·s or less (e.g., 3.5 Pa·s or less), and further preferably 2.0 Pa·s or less, as measured using a viscometer at 25° C., for example. Such measured viscosity is typically measured at a shear rate of 105.7 l/s. To obtain such a measured value, an AR Rheometer (AR-G2, TA Instrument) or a viscosity and viscoelasticity measuring apparatus MARS (Thermo Fisher Scientific K.K.) can be used as a viscometer.

The amphipathic compound according to the present invention has low viscosity that allows it to pass through a 22 gauge injection needle (internal diameter: 0.41 mm) or an injection needle having a width of a lower value than the diameter, more preferably a 26 gauge injection needle (internal diameter: 0.26 mm) or an injection needle having a width of a lower value than the diameter, further preferably a 30 gauge injection needle (internal diameter: 0.15 mm) or an injection needle having a width of a lower value than the diameter, and particularly preferably a very thin 31 gauge injection needle (internal diameter: 0.13 min).

3. Liquid Crystal Forming Capacity of Amphipathic Compound

The amphipathic compound according to the present invention is a liquid crystal compound capable of forming non-lamellar liquid crystal in an aqueous medium. In this Description, an aqueous medium containing an amphipathic compound may be referred to as an "amphipathic compound/water system."

Non-lamellar liquid crystal formed by the amphipathic compound according to the present invention is preferably type II (water-in-oil) liquid crystal wherein hydrophobic groups are oriented outward. Specifically, non-lamellar liquid crystal is more preferably cubic liquid crystal or reverse hexagonal liquid crystal.

Cubic liquid crystal is preferably type II cubic liquid crystal. Cubic liquid crystal structures are generally classified into type I and type II. Cubic liquid crystal having an "oil-in-water" structure is referred to as type I cubic liquid crystal, and in contrast, cubic liquid crystal having a "water-in-oil" structure is referred to as type II cubic liquid crystal. Type I and type II can be determined on the basis of the phase behavior of an amphipathic compound/water system. For example, in the case of type I, as the water content of an amphipathic compound/water system is increased, it is transformed to another type of liquid crystal (e.g., lamellar liquid crystal) and then to micells, and it is finally transformed into a uniform aqueous solution. On the other hand, in the case of the type II liquid crystal, when its water content reaches a certain level or higher, it is transformed into a double phase of "liquid crystal+excess water" in which liquid crystal containing a saturated volume of water and excess water coexist. Thus, even if the water content is increased, no uniform aqueous solution is formed.

Cubic liquid crystal may also be cubic liquid crystal belonging to the crystallographic space group Ia3d (hereinafter, Ia3d cubic liquid crystal), cubic liquid crystal belonging to the crystallographic space group Pn3m (hereinafter, Pn3m cubic liquid crystal), or cubic liquid crystal belonging to the crystallographic space group Im3m (hereinafter, Im3m cubic liquid crystal). Cubic liquid crystal is more preferably Pn3m cubic liquid crystal.

Aqueous media in which the amphipathic compound according to the present invention can form non-lamellar liquid crystal include, but not limited to, water such as sterile water, purified water, distilled water, ion exchanged water, and ultrapure water; electrolyte aqueous solutions such as a physiological saline, an aqueous sodium chloride solution, an aqueous calcium chloride solution, an aqueous magnesium chloride solution, an aqueous sodium sulfate solution, an aqueous potassium sulfate solution, an aqueous sodium carbonate solution, and an aqueous sodium acetate solution; buffer solutions such as a phosphate buffer solution and a Tris-HCl buffer solution; aqueous solutions containing water-soluble organic substances such as glycerin, ethylene glycol, and ethanol; aqueous solutions containing sugar molecules such as glucose, sucrose, and maltose; aqueous solutions containing water soluble polymers, such as polyethylene glycol and polyvinyl alcohol; aqueous solutions containing surfactants such as octyl glucoside, dodecyl maltoside, pluronic (polyethylene glycol/polypropylene glycol/polyethylene glycol copolymer); and body fluids such as intracellular fluid, extracellular fluid, intercellular fluid, lymph fluid, spinal fluid, blood, gastric juice, serum, blood plasma, saliva, tears, seminal fluid, and urine.

The amphipathic compound according to the present invention exhibits high stability under broad environmental conditions. For example, the amphipathic compound according to the present invention has high resistance to hydrolysis and high oxidation stability, although it has a double bond. The amphipathic compound according to the present invention has also low Krafft temperature, so that it can stably form liquid crystal even under low temperatures (6° C. or less, preferably 0° C. or less).

The amphipathic compound according to the present invention can form non-lamellar liquid crystal (preferably cubic liquid crystal or reverse hexagonal liquid crystal) in an aqueous medium typically under relatively wide temperature conditions including room temperature. One or more types of amphipathic compound according to the present invention can be added to an aqueous medium at a concentration ranging from 0.1% by mass to 90% by mass, for example, compared to the total mass of the aqueous medium containing the amphipathic compound according to the present invention, preferably, at a concentration forming water-excess conditions (e.g., 50% by mass to 80% by mass). The solution is then mixed, preferably uniformly, under temperature conditions ranging from −10° C. to 80° C., and preferably ranging from 0° C. to 40° C., provided that a subfreezing temperature is employed under conditions that the aqueous medium does not freeze, such as supercooled state and under conditions other than such conditions, temperatures of 0° C. or higher are employed. As a result, liquid crystal can be stably formed in the aqueous medium from the amphipathic compound according to the present invention.

When the amphipathic compound according to the present invention is administered in vivo, for example, it can stably form type II non-lamellar liquid crystal in body fluid, including, but are not limited to, intracellular fluid, extracellular fluid, intercellular fluid, lymph fluid, spinal fluid, blood, gastric juice, serum, blood plasma, saliva, tears, seminal fluid, and urine.

When causing liquid crystal to form in an aqueous medium using the amphipathic compound according to the present invention, one or more types of amphipathic compound are preferably uniformly dispersed in the aqueous medium.

When causing type II non-lamellar liquid crystal to form in vitro, an aqueous solvent containing the amphipathic compound according to the present invention added is preferably, but not particularly limited to, sufficiently mixed for 1 to 50 hours, for example.

Herein, an aqueous medium containing the amphipathic compound according to the present invention, in which liquid crystal is formed by the amphipathic compound is referred to as a liquid crystal composition.

Structural analysis of the thus formed liquid crystal can be carried out by conventional methods, such as the following methods.

(1) Observation with Polarizing Microscope

A penetration method can be used as a method for easily determining whether or not an amphipathic compound can form liquid crystal in an aqueous medium or if the amphipathic compound forms cubic liquid crystal whether or not the thus formed cubic liquid crystal is of type I or type II. A small amount (several mg) of an amphipathic compound is placed on microscopic glass slide, and then pressure is gently applied with a cover glass, so that a thin film of the amphipathic compound, of which thickness is about 10 microns, is formed (at a diameter ranging from about 1 mm to 5 mm) in the gap between the glass slide and the cover glass. Water or an aqueous solvent is added from the side of the gap between the glass slide and the cover glass via capillary action. Water gradually penetrates from the outer edge of the amphipathic compound thin film into the interior, so that a water content gradient is formed from the amphipathic compound thin film/water interface to the interior of the amphipathic compound thin film. Polarizing microscopic observation thereof enables the determination of a phase type formed depending on the concentration of the amphipathic compound/water system. Through observation that a region that imparts the same isotropic texture as that of a water region, adjacent to the water region (cubic liquid crystals), a region that imparts bright texture (lamellar liquid crystals), and a region that imparts isotropic texture (dry amphipathic compounds) are formed, it is confirmed that the amphipathic compound forms cubic liquid crystal. Also, it can be determined that the amphipathic compound is of type II on the basis of the stable formation of cubic liquid crystal in the interface between the excess water and the amphipathic compound.

(2) Confirmation of Liquid Crystal Structure by Small Angle X-Ray Scattering (SAXS) Assay Whether or not a liquid crystal structure has a cubic lattice may be determined by a small-angle X-ray scattering (SAXS) method, for the purpose of confirming whether or not it is cubic liquid crystal. First, an amphipathic compound/water system sample with a predetermined concentration can be added to an X-ray capillary tube made of quartz, for example, and the capillary tube is sealed with an oxy-fuel burner, and subjected to SAXS assay.

Liquid crystal formation can be confirmed by confirming whether or not the following scattering peak ratio (peak interval) peculiar to each liquid crystal structure is exhibited as a result of SAXS measurement Ratio of Pn3m Cubic Liquid Crystal:

$$\sqrt{2}:\sqrt{3}:\sqrt{4}:\sqrt{6}:\sqrt{8}:\sqrt{9}:\sqrt{10}:,,, \quad \text{[Mathematical expression 1]}$$

Ratio of Ia3d Cubic Liquid Crystal:

$$\sqrt{3}:\sqrt{4}:\sqrt{7}:\sqrt{8}:\sqrt{10}:\sqrt{11}:,,, \quad \text{[Mathematical expression 2]}$$

Ratio of Im3m Cubic Liquid Crystal:

$$\sqrt{2}:\sqrt{4}:\sqrt{6}:\sqrt{8}:\sqrt{10}:\sqrt{12}:\sqrt{14}:,,, \quad \text{[Mathematical expression 3]}$$

Ratio Peculiar to Reverse Hexagonal Liquid Crystal:

$$1:\sqrt{3}:2 \qquad \text{[Mathematical expression 4]}$$

A peak value is calculated from SAXS data and then the reciprocal ratio is found therefrom according to a method known by persons skilled in the art, so that the space group and the lattice constant can be easily determined.

4. Use of Amphipathic Compound

The amphipathic compound according to the present invention forms type II (water-in-oil) non-lamellar liquid crystal in an aqueous medium. Upon the liquid crystal formation, the amphipathic compound according to the present invention enables other substances (e.g., a drug) in the aqueous medium to be incorporated and stably retained within the liquid crystal.

The amphipathic compound that forms type II (water-in-oil) non-lamellar liquid crystal in an aqueous medium can gradually release substances incorporated and retained within the liquid crystal. Therefore, the amphipathic compound according to the present invention can be used as a base for sustained release formulations (slow-release formulations).

Type II non-lamellar liquid crystal that is formed by the amphipathic compound according to the present invention in an aqueous medium has strong bioadhesive properties because of the outward orientation of the hydrophobic groups. The type H non-lamellar liquid crystal further exhibits a high degree of drug encapsulation efficiency, can accelerate transdermal absorption of a drug, and can also accelerate the fine particle dispersion of a hardly-soluble compound. Therefore, the amphipathic compound according to the present invention can be broadly and advantageously used as a base for various formulations. Examples of such a formulation include, but are not limited to, any pharmaceutical drugs, quasi drugs, or cosmetics applicable to living organisms. Examples of a formulation that may be produced using the amphipathic compound according to the present invention as a base, include, but are not limited to, liquid formulations or various similar dosage forms thereto, such as injection formulations (e.g., a depot formulation, a subcutaneous injection formulation, an intradermal injection formulation, an intramuscular injection formulation, an intravenous injection formulation, an intravenous drip infusion formulation, and an arterial injection formulation), suppositories, gels, creams (e.g., paste), and oral formulations (e.g., liquids, an emulsions, and syrups). Of these examples, parenteral formulations are more preferable dosage forms. The amphipathic compound according to the present invention can be added with an active ingredient (typically, a drug) to an aqueous medium, and then dispersed in the aqueous medium by stirring or the like, to form an emulsion. This enables the preparation of formulations retaining the active ingredient and having high biocompatibility. Alternatively, a formulation may also be prepared by adding an active ingredient (typically, a drug) to the amphipathic compound according to the present invention and mixing them. When the latter formulation is prepared, a pharmaceutically applicable surfactant may also be added together with an active ingredient to and dispersed in the amphipathic compound according to the present invention. In the present invention, the term "base" in the context of the formulation refers to an ingredient being a constituent of a formulation (e.g., a carrier, an excipient, a diluent, or an inactive additive) other than an active ingredient such as drugs in the case of pharmaceutical drugs or quasi drugs).

The amphipathic compound according to the present invention is a liquid product or a semi-solid product exhibiting significantly low viscosity such that it can pass through a very thin injection needle as described above. Therefore, a formulation prepared by adding and dispersing an active ingredient (typically, a drug) to and in the amphipathic compound according to the present invention can also be used as an injection formulation. Accordingly, the amphipathic compound according to the present invention can be used particularly advantageously as an ingredient of a base for an injection formulation. Hence, the present invention also provides a base for injection formulations containing the amphipathic compound according to the present invention.

An active ingredient (e.g., a drug) to be added to a base for injection formulations is not particularly limited depending on the specific properties of the active ingredient including hydrophilicity or hydrophobicity and molecular sizes (e.g., large or small), for example. Examples of such an active ingredient, preferably a drug, include, but are not limited to, a peptide, a protein, and a low-molecular-weight drug.

When administered in a living body (in vivo), the amphipathic compound according to the present invention stably forms type II (water-in-oil) non-lamellar liquid crystal in body fluid (aqueous medium), incorporates an active ingredient (e.g., a drug that has been administered together) into the liquid crystal, stably retains the active ingredient therein, and can further gradually release it effectively. Thus, the amphipathic compound according to the present invention can be very advantageously used for injection formulations possessing sustained drug release property, and particularly among them, depot formulations. Therefore, the present invention further provides a base for depot formulations containing the amphipathic compound according to the present invention.

The formulation base and preferably a base for injection formulations according to the present invention, such as a base for depot formulations, comprise at least one (one or more) amphipathic compound according to the present invention. The base for injection formulations according to the present invention may further contain one or more carriers, excipients, or inactive additives (e.g., preservatives, colorant, and aroma chemicals). The base for injection formulation according to the present invention may comprise an aqueous medium. Any aqueous medium that can be used for bases for injection formulation according to the present invention can be used. Examples of such an aqueous medium include: water such as sterile water, purified water, distilled water, ion exchanged water, and ultrapure water; aqueous electrolyte solutions such as a physiological saline solution, an aqueous sodium chloride solution, an aqueous calcium chloride solution, an aqueous magnesium chloride solution, an aqueous sodium sulfate solution, an aqueous potassium sulfate solution, an aqueous sodium carbonate solution, and an aqueous sodium acetate solution; buffer solutions such as a phosphate buffer solution and a Tris-HCl buffer solution; aqueous solutions containing water soluble organic substances such as glycerin, ethylene glycol, and ethanol; aqueous solutions containing sugar molecules such as glucose, sucrose, and maltose; aqueous solutions containing water soluble polymers such as polyethylene glycol and polyvinyl alcohol; and aqueous solutions containing surfactants such as octyl glucoside, dodecyl maltoside, and pluronic (polyethylene glycol/polypropylene glycol/polyethylene glycol copolymer). However, the base for depot formulations according to the present invention preferably contains no aqueous medium in view of realization of local administration to a specific site. Similarly, the depot formulation according to the present invention preferably contains no aqueous medium. The depot formulation according to the present invention may be preferably a mixture of the amphipathic compound according to the present invention and an active ingredient (e.g., a drug). The depot formulation according to the present invention may further contain a pharmaceutically applicable surfactant, as necessary.

A depot formulation is used for a depot technique, which involves injecting a base with a drug encapsulated therein in viva and then causing sustained drug release therefrom. A depot formulation prepared by dispersing an active ingredient (typically, a drug) and, further, a pharmaceutically applicable surfactant as necessary in the amphipathic compound according to the present invention has very low viscosity. Hence, such depot formulation can be administered in vivo using a thin injection needle (via e.g., intradermal, subcutaneous or mucous administration). Through administration of the depot formulation, type II (water-in-oil) non-lamellar liquid crystal can be stably formed in body fluid at the administration site. Furthermore, in that case, an active ingredient contained in the depot formulation and thus co-administered is incorporated into the liquid crystal and retained therein, so that it can be gradually released effectively. The depot formulation prepared using the base for injection formulations according to the present invention possesses sustained release property, so that the drug effect can be sustained for a long time period in a single dose and thus the frequency of drug administration can be decreased. Also, the depot formulation can be administered locally to a target site, so that adverse reaction at sites other than the target site can be minimized. Furthermore, the depot formulation comprising the amphipathic compound according to the present invention as a base can be administered using a very thin injection needle, such as a 30 gauge or a 31 gauge injection needle, so that the pain caused by injection can be suppressed to a very low level. With the use of the depot formulation according to the present invention, an active ingredient (e.g., a drug) can be encapsulated and retained within liquid crystal at a higher concentration in vivo and therefore the injection dose to be administered can be decreased. In this way, the depot formulation according to the present invention is very useful for improving patients' QOL (Quality of Life). The present invention further provides the depot formulation comprising the base for injection formulations according to the present invention.

An active ingredient (e.g., a drug) to be contained in the depot formulation is not particularly limited depending on the specific properties of the active ingredient, such as hydrophilicity or hydrophobicity, or by molecular size (large or small), for example. Examples of such an active ingredient, and preferably a drug, include, but are not limited to, a peptide, a protein, and a low-molecular-weight drugs.

This description includes part or all of the content disclosed in the description and/or drawings of Japanese Patent Application No. 2009-295658, which is a priority document of the present application.

All publications, patents, and patent applications cited herein are incorporated herein by reference in their entirety.

EXAMPLES

The present invention will be explained more specifically with reference to the following Examples. However, the technical scope of the present invention is not limited to these Examples.

The viscosity of each of the compounds shown in the Examples 1-11 was measured using AR Rheometer (AR-G2, TA Instrument) after allowing to stand at the temperature of 25° C. for 12 hours.

Each of the above compounds was confirmed to be capable of passing through a needle of up to 31 gauge by using syringes (hypodermic needle; purchased from ASONE Corporation) attached to a 30 gauge needle (bore diameter 0.15 min) or 31 gauge needle (bore diameter 0.13 mm).

Example 1

Synthesis of mono-O-(5,9,13,17-tetramethyloctadec-4-enoyl)pentaerythritol

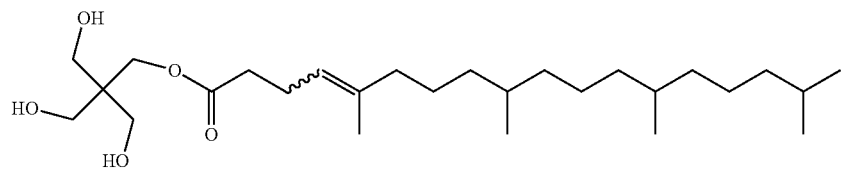 [SMILES: CC(=CCCC(=O)OCC(CO)(CO)CO)CCCC(C)CCCC(C)CCCC(C)C]

Under reduced pressure of 60-70 mmHg and nitrogen gas stream, 250 g (0.71 mol) of methyl 5,9,13,17-tetramethyloctadec-4-enoate was slowly added dropwise at 78-83° C. to a solution of 157 g (1.15 mol) of pentaerythritol and 1.58 g (1.15 mmol) of potassium carbonate in dry N,N-dimethylformamide (700 mL). After the reaction mixture was stirred at the same temperature for 10 hours, formic acid was added at 75° C. to adjust the pH to 4. After the resulting solution was subjected to vacuum concentration, the residue was diluted with t-butylmethylether (1.5 L), and the resulting insoluble matter was separated by filtration. The filtrate was washed with 10% sodium bicarbonate aqueous solution twice, and decolorized with activated carbon (8 g). After filtration, the filtrate was concentrated, and the residue was purified by silica gel column chromatography (hexane/ethyl acetate mixture) to obtain the title compound.

Infrared (IR) spectrum by infrared spectroscopy and viscosity of the obtained compound were measured. The results were as follows.

$^1$H-NMR spectrum (300 MHz, CDCl$_3$, TMS) δ: 0.80-0.95 (m, 12H), 1.00-1.70 (m, 22H), 1.90-2.05 (m, 2H), 2.25-2.45 (m, 4H), 3.64 (s, 6H), 4.24 (s, 2H), 5.07 (brs, 1H).

IR spectrum (NaCl thin film method): 3387, 2926, 2866, 1739, 1461, 1378, 1267, 1139, 1051.

Viscosity: 1.7 Pa·s.

Example 2

Synthesis of mono-O-(5,9,13,17-tetramethyloctadec-4-enoyl)erythritol

Under reduced pressure of 60-70 mmHg and nitrogen gas stream, 199 g (0.564 mol) of methyl 5,9,13,17-tetramethyloctadec-4-enoate was slowly added dropwise to a solution of 191 g (1.56 mol) of erythritol and 1.58 g (1.15 mmol) of potassium carbonate in dry N,N-dimethylformamide (700 mL) at 78-83° C. After the reaction mixture was stirred at the same temperature for 10 hours, formic acid was added at 75° C. to adjust the pH to 4. After the resulting solution was subjected to vacuum concentration, the residue was diluted with t-butylmethylether (1.5 L), and the insoluble matter generated was separated by filtration. The filtrate was washed with 10% sodium bicarbonate aqueous solution twice, and decolorized with activated carbon (8 g). After filtration, the filtrate was concentrated, and the residue was dissolved in ethanol, followed by filtration through cellulose powder. After the filtrate was concentrated, and the resulting residue was purified by silica gel column chromatography (hexane/ethyl acetate mixture) to obtain the title compound.

Infrared (IR) spectrum by infrared spectroscopy and viscosity of the obtained compound were measured. The results were as follows:

$^1$H-NMR spectrum (300 MHz, CDCl$_3$, TMS) δ: 0.80-0.95 (m, 12H), 1.00-1.70 (m, 22H), 1.40-2.05 (m, 2H), 2.25-2.45 (m, 4H), 3.55-3.95 (m, 4H), 4.25-4.40 (m, 2H), 5.09 (dd, J=4.8 Hz, J=4.8 Hz, 1H).

IR spectrum (NaCl thin film method): 3407, 2926, 2867, 1738, 1461, 1377, 1269, 1172, 1081.

Viscosity: 2.0 Pa·s.

Example 3

Synthesis of mono-O-(5,9,13,17-tetramethyloctadec-4-enoyl)glycerol

The title compound was synthesized using the same procedure as employed in Example 2, but with glycerol instead of erythritol, having the following properties:

$^1$H-NMR spectrum (300 MHz, CDCl$_3$, TMS) δ: 0.80-0.95 (m, 12H), 1.00-1.70 (m, 22H), 1.85-2.15 (m, 2H), 2.15-2.55 (m, 4H), 3.53-3.78 (m, 3H), 3.80-4.00 (m, 1H), 4.10-4.25 (m, 2H), 5.08 (dd, J=6.9 Hz, J=6.9 Hz, 1H).

Example 4

Synthesis of mono-O-(5,9,13,17-tetramethyloctadec-4-enoyl)di glycerol

The title compound was synthesized using the same procedure as employed in Example 2, but with diglycerol instead of erythritol, having the following properties:

$^1$H-NMR spectrum (300 MHz, CDCl$_3$, TMS) δ: 0.80-0.90 (m, 12H), 1.00-1.70 (m, 22H), 1.97 (ddd, J=17.4 Hz, J=7.8 Hz, J=6.9 Hz, 2H), 2.20-2.45 (m, 4H), 3.50-4.10 (m, 8H), 4.10-4.25 (m, 2H), 5.08 (dd, J=6.6 Hz, J=6.6 Hz, 1H).

Example 5

Synthesis of mono-O-(5,9,13,17-tetramethyloctadec-4-enoyl)triglycerol

The title compound was synthesized using the same procedure as employed in Example 2, but with triglycerol instead of erythritol, having the following properties:

$^1$H-NMR spectrum (300 MHz, CDCl$_3$, TMS) δ: 0.80-0.90 (m, 12H), 1.00-1.70 (m, 22H), 1.97 (ddd, J=17.4 Hz, J=7.8 Hz, J=7.8 Hz, 2H), 2.25-2.45 (m, 4H), 3.45-4.05 (m, 13H), 4.10-4.20 (m, 2H), 5.08 (brs, 1H).

Example 6

Synthesis of mono-O-(5,9,13,17-tetramethyloctadec-4-enoyl)sorbitol

The title compound was synthesized using the same procedure as employed in Example 2, but with sorbitol instead of erythritol, having the following properties:

$^1$H-NMR spectrum (300 MHz, CDCl$_3$, TMS) δ: 0.80-0.90 (m, 12H), 1.00-1.70 (m, 22H), 1.80-2.05 (m, 2H), 2.25-2.45 (m, 4H), 3.50-4.40 (m, 8H), 5.07 (brs, 1H).

Example 7

Synthesis of 5,9,13,17-tetramethyloctadec-4-en-1-ol

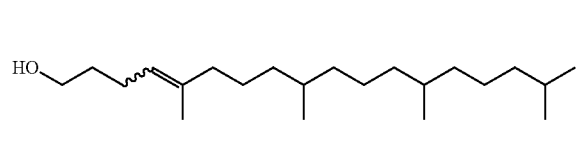 [SMILES: CC(=CCCCO)CCCC(C)CCCC(C)CCCC(C)C]

Under a nitrogen atmosphere, 9.6 g (0.25 mol) of lithium aluminum hydride was added little by little at 0° C. to a solution of 150 g (0.425 mol) of methyl 5,9,13,17-tetramethyloctadec-4-enoate in dry tetrahydrofuran (850 mL). After being stirred at 50° C. for 2 hours, the reaction mixture was cooled on ice, followed by careful addition of water until the resulting gray suspension turned white. Sodium sulfate was added to the solution at room temperature for drying. After filtration, the filtrate was concentrated to obtain 133.8 g of the title compound (97% yield) as a colorless transparent liquid. The results of NMR analysis of the resulting compound are as shown below.

$^1$H-NMR spectrum (400 MHz, CDCl$_3$, TMS) δ: 0.7-0.95 (m, 12), 0.95-1.85 (m, 24H), 1.9-2.1 (m, 4H), 3.63 (t, J=6.5 Hz, 2H), 5.12 (br t, J=7.2 Hz, 1H).

Example 8

Synthesis of 1-O-(5,9,13,17-tetramethyloctadec-4-enyl)-D-xylopyranoside triacetate

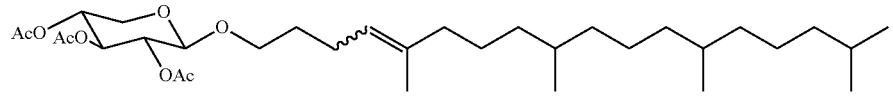 [SMILES: CC(=O)OC1COC(OCCCC=C(C)CCCC(C)CCCC(C)CCCC(C)C)C(OC(C)=O)C1OC(C)=O]

Under a nitrogen atmosphere, 80.0 g (0.251 mol) of β-xylose tetraacetate and 106 g (0.327 mol) of 5,9,13,17-tetramethyloctadec-4-en-1-ol was dissolved in dry acetonitrile (0.30 L), and stirred for 30 min. After the solution was cooled to 0° C., 38 mL (0.30 mol) of boron trifluoride diethyl etherate complex was added. The reaction mixture was allowed to warm up to room temperature while being stirred overnight before addition of 70 mL (0.50 mol) of triethylamine at 0° C. The resulting solution was diluted with ethyl acetate, and washed with water, 3M hydrochloric acid (twice), saturated sodium bicarbonate aqueous solution (twice), and saturated brine, successively, and dried over magnesium sulfate. After filtration, the filtrate was concentrated to obtain 161.95 g of the title compound as a crude product. A part of the crude product was purified by silica gel column chromatography (hexane/ethyl acetate 85:15). The results of NMR analysis of the resulting compound are as shown below.

$^1$H-NMR spectrum (400 MHz, CDCl$_3$, TMS) δ: 0.8-0.95 (m, 12H), 1.0-1.8 (m, 24H), 1.85-2.1 (m, 4H), 2.03 (s, 3H), 2.05 (s, 6H), 3.35 (dd, J=9.12 Hz, 1H), 3.45 (m, 1H), 3.80 (m, 1H), 4.11 (dd, J=5, 12 Hz, 1H), 4.47 (d, J=6.8 Hz, 1H), 4.94 (m, 2H), 5.09 (m, 1H), 5.16 (dd, J=8.7, 8.7 Hz, 1H).

Example 9

Synthesis of 1-O-(5,9,13,17-tetramethyloctadec-4-enyl)-D-xylopyranoside

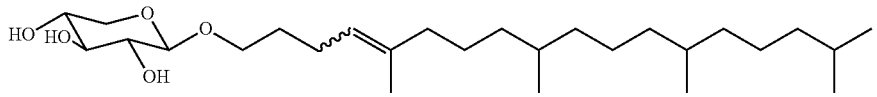 [SMILES: CC(=CCCCOC1OCC(O)C(O)C1O)CCCC(C)CCCC(C)CCCC(C)C]

A solution of 13.4 g (0.248 mmol) of sodium methylate in methanol (250 mL) was added to a solution of 160.33 g of the crude product 1-O-(5,9,13,17-tetramethyloctadec-4-enyl)-D-xylopyranoside triacetate synthesized in Example 8 in methanol/tetrahydrofuran (1:1, 500 mL) at room temperature. After being stirred for 1 hour, 17.7 mL (0.248 mmol) of acetyl chloride was added to the reaction solution and then the solution was confirmed to be neutralized. After addition of water, the solution was extracted with ethyl acetate (twice). The extracts were washed with saturated brine, and dried over magnesium sulfate. After filtration, the filtrate was concentrated, and the resulting residue was purified by silica gel column chromatography (hexane/ethyl acetate=67:33-0:100) to obtain 24.6 g of the title compound (22% yield in 2 steps) as a colorless transparent semi-solid. The results of NMR analysis of the resulting compound are as shown below.

$^1$H-NMR spectrum (400 MHz, CDCl$_3$, TMS) δ: 0.7-0.9 (m, 12H), 1.0-1.7 (m, 24H), 1.85-2.1 (m, 4H), 3.29 (dd, J=9, 11.6 Hz, 1H), 3.41 (m, 1H), 3.45-3.8 (m, 5H), 3.83 (m, 1H), 3.98 (dd, J=4.4, 11.6 Hz, 1H), 4.27 (m, 1H), 4.30 (d, J=6.8 Hz, 1H), 5.10 (m, 1H).

Example 10

Synthesis of mono-O-(5,9,13,17-tetramethyloctadec-4-enyl)pentaerythritol

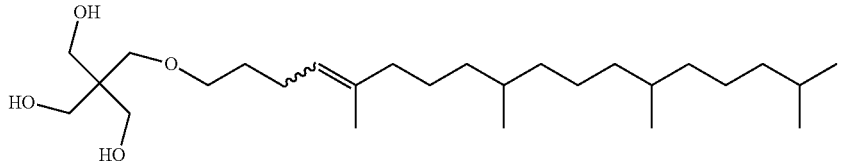 [SMILES: CC(=CCCCOCC(CO)(CO)CO)CCCC(C)CCCC(C)CCCC(C)C]

Under a nitrogen atmosphere, 55 mL (0.39 mol) of triethylamine, 59.9 g (0.314 mol) of p-toluenesulfonyl chloride, and 2.5 g (26 mmol) of trimethylamine hydrochloride were added to a solution of 85.0 g (0.262 mol) of 5,9,13,17-tetramethyloctadec-4-en-1-ol in dry methylene chloride (0.26 L) at 0° C., sequentially. After being stirred for 1 hour, 9.9 mL (79 mmol) of N,N-dimethyl-1,3-propanediamine was added to the reaction solution at 0° C. After being stirred for 1 hour, the mixture was diluted with a mixed solvent of hexane/ethyl acetate. The resulting solution was washed with water, 3M hydrochloric acid (twice), saturated sodium bicarbonate aqueous solution, and saturated brine, successively, and dried over magnesium sulfate. After filtration, the filtrate was concentrated, and the resulting residue was purified by silica gel column chromatography (hexane/ethyl acetate=90:10) to obtain 116 g of (5,9,13,17-tetramethyloctadec-4-enyl)tosylate (93% yield).

Under a nitrogen atmosphere, 2.08 g (11.8 mmol) of 2,2-dimethyl-1,3-dioxane-5,5-dimethanol was added to a solution of 0.51 g (63%, 14 mmol) of sodium hydride in dry N,N-dimethylformamide (18 mL) in several portions, with cooling on ice. After the mixture was stirred for 1 hour at 50° C., a solution of 2.81 g (5.88 mmol) of the above (5,9,13,17-tetramethyloctadec-4-enyl)tosylate in dry N,N-dimethylformamide (9 mL) was added dropwise thereto for 30 min with additional stirring for 3 hours at the same temperature. After addition of water at 0° C., the mixture was extracted with ethyl acetate. The extract was washed with water, saturated sodium bicarbonate aqueous solution, and saturated brine, successively, and dried over magnesium sulfate. After filtration, the filtrate was concentrated, and the resulting residue was purified by silica gel column chromatography (hexane/ethyl acetate=85:15) to obtain 1.52 g of 2,2-dimethyl-1,3-dioxane-5-(5,9,13,17-tetramethyloctadec-4-enoxy)methyl-5-methanol (54% yield).

1.52 g (3.15 mmol) of the above product was dissolved in methanol (50 mL), and 1 mL (1.25 M, 1.25 mmol) of hydrochloric acid/methanol was added at room temperature. The reaction mixture was stirred for 12 hours at room temperature, and subjected to vacuum concentration. The resulting residue was purified by silica gel column chromatography (chloroform/methanol=95:5) to obtain 1.15 g of the title compound (83% yield) as a colorless transparent viscous product. The results of NMR analysis and viscosimetry of the resulting compound are as shown below.

$^1$H-NMR spectrum (400 MHz, CDCl$_3$, TMS) δ: 0.8-0.9 (m, 12H), 1.0-1.7 (m, 24H), 1.9-2.1 (m, 4H), 2.43 (m, 3H), 3.43 (t, J=6.6 Hz, 2H), 3.47 (s, 2H), 3.73 (dd, J=1.0, 5.8 Hz, 6H), 5.09 (br t, J=7.3 Hz, 1H).

Viscosity: 1.9 Pa·s.

Example 11

Synthesis of 1-O-(5,9,13,17-tetramethyloctadec-4-enyl)erythritol (1-ether), and 2-O-(5,9,13,17-tetramethyloctadec-4-enyl)erythritol (2-ether)

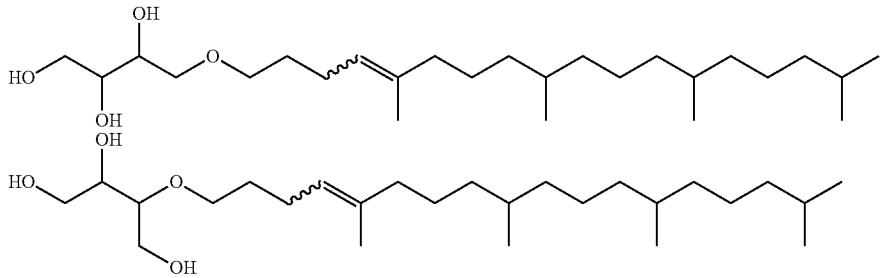

Under a nitrogen atmosphere, 0.45 g (63%, 12 mmol) of sodium hydride was added to a solution of 1.92 g (11.9 mmol) of 1,2-O-isopropylideneerythritol in dry N,N-dimethylformamide (30 mL) in several portions with cooling on ice. After the mixture was stirred for 20 min at room temperature, a solution of 4.2 g (1.0 mmol) of (5,9,13,17-tetramethyloctadec-4-enyl)tosylate in dry N,N-dimethylformamide (30 mL) was added with additional stirring for 3 hours at 50° C. By thin-layer chromatography (TLC) analysis, the ratio of 1,2-O-isopropylidene-4-O-(5,9,13,17-tetramethyloctadec-4-enyl)erythritol to 1,2-O-isopropylidene-3-O-(5,9,13,17-tetramethyloctadec-4-enyl)erythritol generated was approximately 1:1. After addition of water at 0° C., the reaction mixture was extracted with ethyl acetate. The extract was washed with water, saturated sodium bicarbonate aqueous solution, and saturated brine, successively, and dried over magnesium sulfate. After filtration, the filtrate was concentrated, and the resulting residue was purified by silica gel column chromatography (hexane/ethyl acetate=90:10 to 85:15) to obtain 1.12 g of 1,2-O-isopropylidene-4-O-(5,9,13,17-tetramethyloctadec-4-enyl)erythritol (27% yield) and 1.54 g of 1,2-O-isopropyl idene-3-O-(5,9,13,17-tetramethyloctadec-4-enyl)erythritol (37% yield).

1.10 g (2.67 mmol) of the above product 1,2-O-isopropylidene-4-O-(5,9,13,17-tetramethyloctadec-4-enyl)erythritol and 1.50 g (3.63 mmol) of 1,2-O-isopropylidene-3-O-(5,9,13,17-tetramethyloctadec-4-enyl)erythritol were each dissolved in 15 mL of methanol added, and 51 mg (0.30 mmol) of p-toluenesulfonic acid monohydrate was added thereto at room temperature. After being stirred for 5 hours at room temperature, the each reaction mixture was neutralized by addition of triethylamine. After vacuum concentration, the resulting each residue was purified by silica gel column chromatography (chloroform/methanol=98:2) to obtain 0.60 g of the title 1-ether compound (1-O-(5,9,13,17-tetramethyloctadec-4-enyl)erythritol) (60% yield) as a colorless transparent semi-solid and 0.80 g of the title 2-ether compound (2-O-(5,9,13,17-tetramethyloctadec-4-enyl)erythritol) (60% yield) as a colorless transparent viscous product, respectively.

(1) 1-O-(5,9,13,17-tetramethyloctadec-4-enyl)erythritol $^1$H-NMR spectrum (400 MHz, CDCl$_3$, TMS) δ: 0.8-0.9 (m, 12H), 1.0-1.7 (m, 24H), 1.9-2.1 (m, 4H), 2.32 (dd, J=5.8, 10.1 Hz, 1H), 2.66 (dd, J=2.4, 5.8 Hz, 1H), 2.78 (t, J=5.8 Hz, 1H), 3.49 (t, J=6.5 Hz, 2H), 3.57 (d, J=4.8, 9.7 Hz, 1H), 3.60 (d, J=5.8, 9.7 Hz, 1H), 3.7-3.8 (m, 3H), 3.82 (m, 1H), 5.10 (br t, J=7 Hz, 1H).

Viscosity: 2.3 Pa·s.

(2) 2-O-(5,9,13,17-tetramethyloctadec-4-enyl)erythritol $^1$H-NMR spectrum (400 MHz, CDCl$_3$, TMS) δ: 0.8-0.9 (m, 12H), 1.0-1.7 (m, 24H), 1.9-2.1 (m, 4H), 2.3-2.4 (m, 2H), 2.77 (m, 1H), 3.39 (dd, J=5, 10 Hz, 1H), 3.51 (m, 1H), 3.60 (m, 1H), 3.65-3.9 (m, 5H), 5.10 (br t, J=7 Hz, 1H).

Viscosity: 3.2 Pa·s.

Example 12

Synthesis of mono-O-(5,9,13,17-tetramethyloctadec-4-enyl)erythritol

Under a nitrogen atmosphere, 2.19 g (55%, 50.2 mmol) of sodium hydride was added to a solution of 14.1 g (83.6 mmol) of 1,2-O-isopropylideneerythritol in dry N,N-dimethylformamide (100 mL) in several portions, with cooling on ice. After the mixture was stirred for 30 min at room temperature, a solution of 20.0 g (41.8 mmol) of (5,9,13,17-tetramethyloctadec-4-enyl)tosylate in dry N,N-dimethylformamide (20 mL) was added with additional stirring for 2 hours at 50° C. By thin-layer chromatography (TLC) analysis, the ratio of 1,2-O-isopropylidene-4-O-(5,9,13,17-tetramethyloctadec-4-enyl)erythritol to 1,2-O-isopropylidene-3-O-(5,9,13,17-tetramethyloctadec-4-enyl)erythritol generated was approximately 1:1. After addition of saturated ammonium chloride aqueous solution at 0° C., the reaction mixture was extracted with a mixed solvent of hexane/ethyl acetate. The extract was washed with saturated sodium bicarbonate aqueous solution and saturated brine successively, and then dried over magnesium sulfate. After filtration, the filtrate was concentrated to give 20.5 g of a mixture of 1,2-O-isopropylidene-4-O-(5,9,13,17-tetramethyloctadec-4-enyl)erythritol and 1,2-O-isopropylidene-3-O-(5,9,13,17-tetramethyloctadec-4-enyl)erythritol.

20.5 g of the above mixture was dissolved in tetrahydrofuran (190 mL), and 3M hydrochloric acid (60 mL) was added thereto at room temperature. After being stirred at room temperature overnight, the reaction mixture was extracted with ethyl acetate. The extract was washed with water, saturated sodium bicarbonate aqueous solution, and saturated brine, successively, and dried over magnesium sulfate. After filtration, the filtrate was concentrated, and the resulting residue was purified by silica gel column chromatography (hexane/ethyl acetate=50:50 to 0:100) to obtain 10.4 g of the title compound (53% yield in 2 steps) as a colorless transparent viscous product.

$^1$H-NMR spectrum (300 MHz, CDCl$_3$, TMS) δ: 0.8-0.9 (m, 12H), 1.0-1.7 (m, 24H), 1.9-2.1 (m, 4H), 2.75 (m, 15H), 2.96 (m, 0.5H), 3.13 (m, 0.5H), 3.23 (m, 0.5H), 3.38 (m, 0.5H), 3.45-3.7 (m, 3H), 3.7-3.9 (m, 4.5H), 5.11 (m, 1H).

Example 13

Formation of a liquid crystal by mono-O-(5,9,13,17-tetramethyloctadec-4-enoyl)pentaerythritol and analysis thereof Mono-O-(5,9,13,17-tetramethyloctadec-4-enoyl)pentaerythritol and pure water were introduced into a mixing device at the concentration of 50 wt % Mono-O-(5,9,13,17-tetramethyloctadec-4-enoyl)pentaerythritol (water-excess condition), and incubation thereof was carried out while performing 100 or more times of mixing operations at room temperature (25° C.) over the period of 24 hours. Thus, a homogeneously mixed sample of mono-O-(5,9,13,17-tetramethyloctadec-4-enoyl)pentaerythritol/water system was obtained. This sample of mono-O-(5,9,13,17-tetramethyloctadec-4-enoyl)pentaerythritol/water system appeared to be a white turbid gel composition.

Subsequently, the thus obtained sample of mono-O-(5,9,13,17-tetramethyloctadec-4-enoyl)pentaerythritol/water system was confirmed to be a cubic liquid crystal by small-angle x-ray scattering (SAXS). The sample of mono-O-(5,9,13,17-tetramethyloctadec-4-enoyl)pentaerythritol/water system was introduced into a quartz X-ray capillary tube, the tip of the capillary was sealed using an oxygen burner, and the capillary tube was subjected to the SAXS analysis. The NANO-Viewer nano-scale X-ray structure analysis equipment (Rigaku) was used for SAXS analysis. SAXS analysis was performed by X-ray irradiation at room temperature (25° C.), 40 kV, 50 mA, wavelength λ=0.1542 nm (Cu-Kα) for 15 min.

As a result of SAXS analysis, 5 sharp scattering peaks were observed at least. The peak value ratio exhibited the following ratio peculiar to the cubic liquid crystal belonging to the crystallographic space group Pn3m:

$$\sqrt{2}:\sqrt{3}:\sqrt{4}:\sqrt{6}:\sqrt{8}:\sqrt{9}.$$

Thus, the sample of mono-O-(5,9,13,17-tetramethyloctadec-4-enoyl)pentaerythritol/water system was confirmed to form a cubic liquid crystal that belong to the crystallographic space group Pn3m (ac (lattice constant)=7.80 nm).

The result of SAXS analysis of the sample of mono-O-(5,9,13,17-tetramethyloctadec-4-enoyl)pentaerythritol/water system is shown in FIG. 1.

Example 14

Formation of a liquid crystal by mono-O-(5,9,13,17-tetramethyloctadec-4-enoyl)erythritol and analysis thereof mono-O-(5,9,13,17-tetramethyloctadec-4-enoyl)erythritol synthesized in Example 2 and water were homogenously mixed in accordance with the same procedure as in Example 13 to obtain a sample of mono-O-(5,9,13,17-tetramethyloctadec-4-enoyl)erythritol/water system. SAXS analysis of the sample of mono-O-(5,9,13,17-tetramethyloctadec-4-enoyl)erythritol/water system was performed in the same manner as in Example 13. As a result, at least 3 sharp scattering peaks were observed. The peak value ratio exhibited the following ratio peculiar to the reverse hexagonal liquid crystal:

$$1:\sqrt{3}:2.$$

Thus, the sample of mono-O-(5,9,13,17-tetramethyloctadec-4-enoyl)erythritol/water system was confirmed to form a reverse hexagonal liquid crystal.

Figure 2:
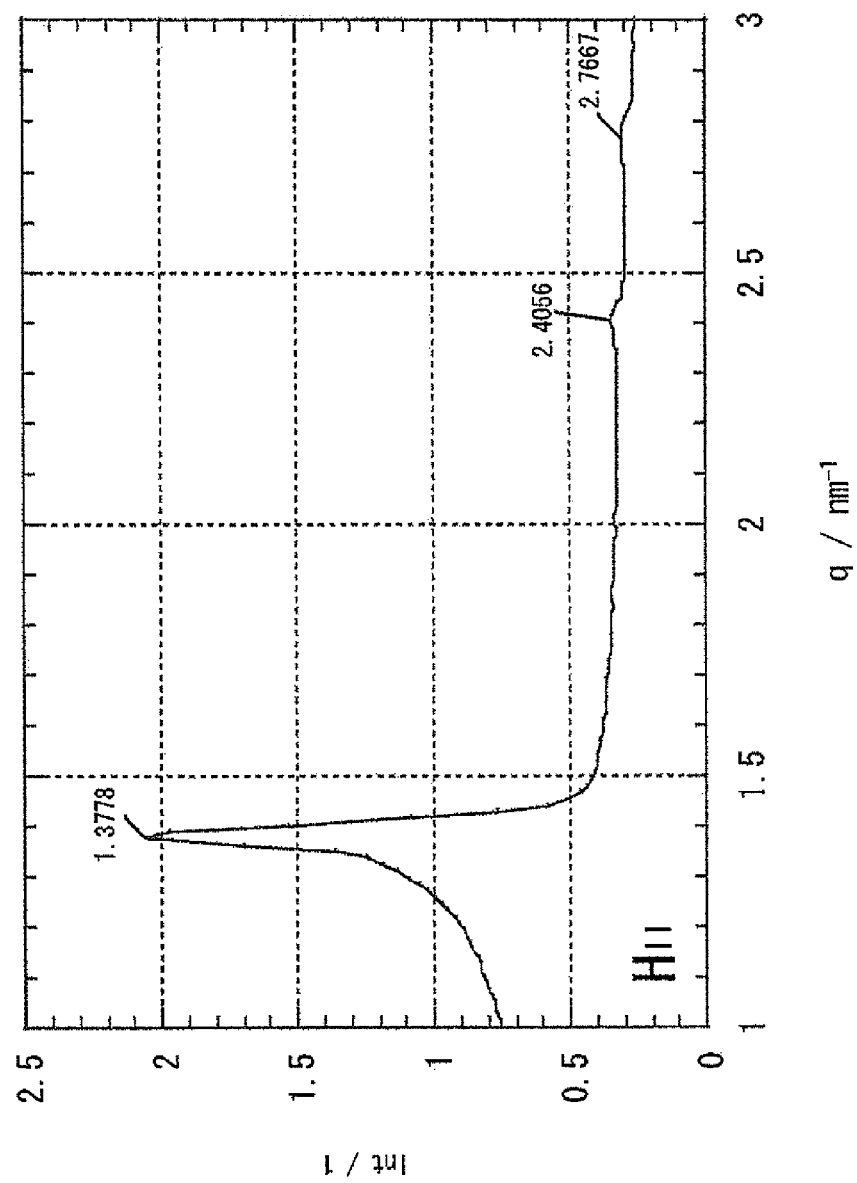
FIG. 2 shows a scattering curve showing the results of SAXS measurement (small-angle scattering measurement) of a 1-O-(5,9,13,17-tetramethyloctadec-4-enoyl)erythritol/ water system sample. The scattering curve is plotted against scattering vector length $q=(4\pi/\lambda)\sin(\theta/2)$, wherein $\theta$ denotes scattering angle. The vertical axis indicates relative intensity compared to the intensity of a direct beam attenuated by a semi-transparent beam stopper having a base index of 1.

The result of SAXS analysis of the sample of mono-O-(5,9,13,17-tetramethyloctadec-4-enoyl)erythritol/water system is shown in FIG. 2.

Example 15

Formation of a liquid crystal by 1-O-(5,9,13,17-tetramethyloctadec-4-enyl)-D-xylopyranoside and analysis thereof 1-O-(5,9,13,17-tetramethyloctadec-4-enyl)-D-xylopyranoside and water were homogeneously mixed in accordance with the same procedure as in Example 13 to obtain a sample of 1-O-(5,9,13,17-tetramethyloctadec-4-enyl)-D-xylopyranoside/water system. SAXS analysis of the sample of 1-O-(5,9,13,17-tetramethyloctadec-4-enyl)-D-xylopyranoside/water system was performed in the same manner as in Example 13. As a result, at least 4 sharp scattering peaks were observed. The peak value ratio exhibited the following ratio peculiar to the cubic liquid crystal belonging to the crystallographic space group Pn3m:

$$\sqrt{2}:\sqrt{3}:\sqrt{4}:\sqrt{6}:\sqrt{8}:\sqrt{9}.$$

Thus, the sample of 1-O-(5,9,13,17-tetramethyloctadec-4-enyl)-D-xylopyranoside/water system was confirmed to form a cubic liquid crystal that belong to the crystallographic space group Pn3m (ac=8.9 nm).

Example 16

Formation of a liquid crystal by mono-O-(5,9,13,17-tetramethyloctadec-4-enyl)pentaerythritol and analysis thereof Mono-O-(5,9,13,17-tetramethyloctadec-4-enyl)pentaerythritol and water were homogeneously mixed in accordance with the same procedure as in Example 13 to obtain a sample of mono-O-(5,9,13,17-tetramethyloctadec-4-enyl)pentaerythritol/water system. SAXS analysis of the sample of mono-O-(5,9,13,17-tetramethyloctadec-4-enyl)pentaerythritol/water system was performed in the same manner as in Example 13. As a result, at least 3 sharp scattering peaks were observed. The peak value ratio exhibited the following ratio peculiar to the reverse hexagonal liquid crystal:

$$1:\sqrt{3}:2.$$

Thus, the sample of mono-O-(5,9,13,17-tetramethyloctadec-4-enyl)pentaerythritol/water system was confirmed to form a reverse hexagonal liquid crystal.

Example 17

Formation of a liquid crystal by 1-O-(5,9,13,17-tetramethyloctadec-4-enyl)erythritol and analysis thereof 1-O-(5,9,13,17-tetramethyloctadec-4-enyl)erythritol and water were homogeneously mixed in accordance with the same procedure as in Example 13 to obtain a sample of 1-O-(5,9,13,17-tetramethyloctadec-4-enyl)erythritol/water system. SAXS analysis of the sample of 1-O-(5,9,13,17-tetramethyloctadec-4-enyl)erythritol/water system was performed in the same manner as in Example 13. As a result, at least 3 sharp scattering peaks were observed. The peak value ratio exhibited the following ratio peculiar to the reverse hexagonal liquid crystal:

$1:\sqrt{3}:2.$

Thus, the sample of 1-O-(5,9,13,17-tetramethyloctadec-4-enyl)erythritol/water system was confirmed to form a reverse hexagonal liquid crystal.

Example 18

Formation of a liquid crystal by 2-O-(5,9,13,17-tetramethyloctadec-4-enyl)erythritol and analysis thereof 2-O-(5,9,13,17-tetramethyloctadec-4-enyl)erythritol and water were homogeneously mixed in accordance with the same procedure as in Example 13 to obtain a sample of 2-O-(5,9,13,17-tetramethyloctadec-4-enyl)erythritol/water system. SAXS analysis of the sample of 2-O-(5,9,13,17-tetramethyloctadec-4-enyl)erythritol/water system was performed in the same manner as in Example 13. As a result, at least 4 sharp scattering peaks were observed. The peak value ratio exhibited the following ratio peculiar to the cubic liquid crystal belonging to the crystallographic space group Pn3m:

$\sqrt{2}:\sqrt{3}:\sqrt{4}:\sqrt{6}:\sqrt{8}:\sqrt{9}.$

Thus, the sample of 2-O-(5,9,13,17-tetramethyloctadec-4-enyl)erythritol/water system was confirmed to form a cubic liquid crystal that belong to the crystallographic space group Pn3m (ac=8.9 nm).

Example 19

Formation of a liquid crystal by a mixture (1:1) of 1-O-(5,9,13,17-tetramethyloctadec-4-enyl)erythritol and 2-O-(5,9,13,17-tetramethyloctadec-4-enyl)erythritol and analysis thereof A mixture (1:1) of 1-O-(5,9,13,17-tetramethyloctadec-4-enyl)erythritol and 2-O-(5,9,13,17-tetramethyloctadec-4-enyl)erythritol and water were homogeneously mixed in accordance with the same procedure as in Example 13 to obtain a sample of the mixture (1:1) of 1-O-(5,9,13,17-tetramethyloctadec-4-enyl)erythritol and 2-O-(5,9,13,17-tetramethyloctadec-4-enyl)erythritol/water system. SAXS analysis of the sample of the mixture (1:1) of 1-O-(5,9,13,17-tetramethyloctadec-4-enyl)erythritol and 2-O-(5,9,13,17-tetramethyloctadec-4-enyl)erythritol/water system was performed in the same manner as in Example 13. As a result, at least 3 sharp scattering peaks were observed. The peak value ratio exhibited the following ratio peculiar to the reverse hexagonal liquid crystal:

$1:\sqrt{3}:2.$

Thus, the sample of the mixture (1:1) of 1-O-(5,9,13,17-tetramethyloctadec-4-enyl)erythritol and 2-O-(5,9,13,17-tetramethyloctadec-4-enyl)erythritol/water system was confirmed to form a reverse hexagonal liquid crystal.

Example 20

Synthesis of mono-O-(5,9,13,17-tetramethyloctadec-4-enoyl)xylitol

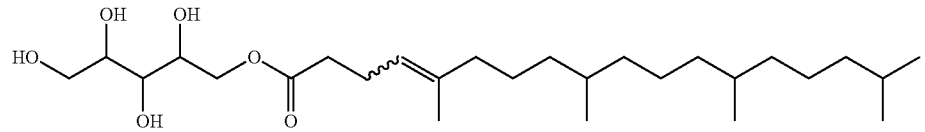 [SMILES: CC(=CCCC(=O)OCC(O)C(O)C(O)CO)CCCC(C)CCCC(C)CCCC(C)C]

1.0 g (2.8 mmol) of methyl 5,9,13,17-tetramethyloctadec-4-enoate was slowly added dropwise to a solution of 0.86 g (2.8 mmol) of xylitol and 0.78 g (5.7 mmol) of potassium carbonate in dry N,N-dimethylformamide (2.5 mL) at 80° C. After the reaction mixture was stirred at 100° C. for 24 hours, the potassium carbonate was separated by filtration. The resulting solution was diluted with t-butylmethylether, and washed with water, 1M hydrochloric acid, saturated sodium bicarbonate aqueous solution, and saturated brine, successively, and dried over magnesium sulfate. After filtration, the filtrate was concentrated, and the resulting residue was purified by silica gel column chromatography (methanol/methylene chloride mixture) to obtain 146 mg of the title compound (12% yield) as a colorless viscous product.

The results of 1H-NMR analysis of the thus obtained product are as shown below.

$^1$H-NMR spectrum (300 MHz, CDCl$_3$, TMS) δ: 0.80-0.90 (m, 12H), 1.00-1.70 (m, 22H), 1.90-2.05 (m, 2H), 2.25-2.45 (m, 4H), 3.65 (brs, 1H), 3.70-3.90 (m, 3H), 4.02 (hrs, 1H), 4.24 (d, J=5.9 Hz, 2H), 5.08 (brs, 1H).

Example 21

Synthesis of mono-O-(5,9,13,17-tetramethyloctadec-4-enoyl)mannitol

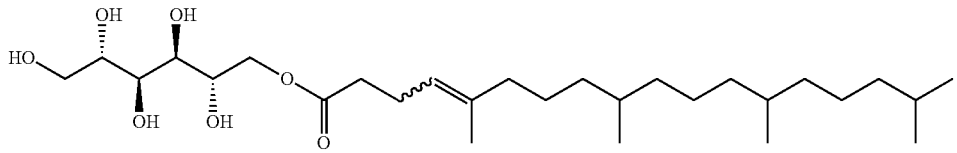 [SMILES: CC(=CCCC(=O)OC[C@H](O)[C@H](O)[C@@H](O)[C@@H](O)CO)CCCC(C)CCCC(C)CCCC(C)C]

The title compound was synthesized using the same procedure as employed in Example 20, but with 1.0 g (5.7 mmol) of mannitol instead of xylitol. The compound was obtained as a white semi-solid (21% yield) having the following properties:

$^1$H-NMR spectrum (300 MHz, CDCl$_3$+3% CD$_3$OD, TMS) δ: 0.80-0.95 (m, 12H), 1.00-1.58 (m, 19H), 1.60 and 1.67 (s, 3H, 5-CH$_3$), 1.90-2.00 (m, 2H), 2.25-2.45 (m, 4H), 3.65-3.95 (m, 6H), 4.26 (dd, J=5.9, 11.3 Hz, 1H), 4.38 (d, J=12.0 Hz, 1H), 5.08 (brs, 1H).

Example 22

Synthesis of mono-O-(5,9,13,17-tetramethyloctadec-4-enoyl)dipentaerythritol

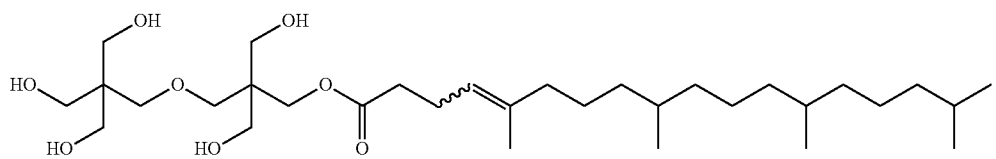 [SMILES: CC(=CCCC(=O)OCC(CO)(CO)COCC(CO)(CO)CO)CCCC(C)CCCC(C)CCCC(C)C]

The title compound was synthesized using the same procedure as employed in Example 20, but with 1.44 g (5.67 mmol) of dipentaerythritol instead of xylitol. The compound was obtained as a white powder (13% yield) having the following properties:

$^1$H-NMR spectrum (300 MHz, CDCl$_3$+3% CD$_3$OD, TMS) δ: 0.80-0.90 (m, 12H), 1.00-1.70 (m, 22H), 1.85-2.00 (m, 2H), 2.25-2.40 (m, 4H), 3.36 (s, 4H), 3.53 (brs, 10H), 4.04 (s, 2H), 5.05 (brs, 1H).

Example 23

Synthesis of mono-O-(5,9,13,17-tetramethyloctadec-4-enoyl)ascorbic acid

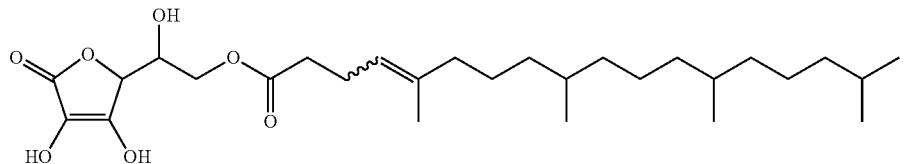 [SMILES: CC(=CCCC(=O)OCC(O)C1OC(=O)C(O)=C1O)CCCC(C)CCCC(C)CCCC(C)C]

0.50 g (2.8 mmol) of ascorbic acid was dissolved in concentrated sulfuric acid (14 mL). After addition of 1.0 g (2.8 mmol) of methyl 5,9,13,17-tetramethyloctadec-4-enoate, the mixture was stirred for 24 hours at room temperature. The reaction mixture was poured into iced water, and extracted with ethyl acetate. The extract was washed with water, 1M hydrochloric acid, saturated sodium bicarbonate aqueous solution, and saturated brine, successively, and dried over sodium sulfate. After filtration, the filtrate was concentrated, and the resulting residue was purified by silica gel column chromatography (methanol/methylene chloride mixture) to obtain the title compound.

Example 24

Synthesis of 1-O-(5,9,13,17-tetramethyloctadec-4-enyl)-D-glucoside

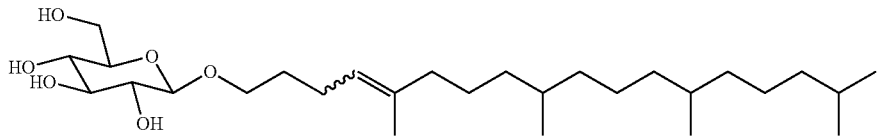 [SMILES: CC(=CCCCOC1OC(CO)C(O)C(O)C1O)CCCC(C)CCCC(C)CCCC(C)C]

3.0 g (7.7 mmol) of β-D-Glucose pentaacetate and 3.24 g (9.99 mmol) of 5,9,13,17-tetramethyloctadec-4-en-1-ol were dissolved in dry acetonitrile (8 mL). 1.95 mL (15.4 mmol) of boron trifluoride diethyl etherate complex was added to the solution with cooling on ice. The reaction mixture was allowed to warm up slowly to room temperature while being stirred overnight before addition of 3.2 mL (23 mmol) of triethylamine at 0° C. The resulting solution was diluted with ethyl acetate, and washed with water, 1M hydrochloric acid, saturated sodium bicarbonate aqueous solution, and saturated brine, successively, and dried over sodium sulfate. After filtration, the filtrate was concentrated to obtain 1-O-(5,9,13,17-tetramethyloctadec-4-enyl)-D-glucopyranoside tetraacetate as a crude product.

The above crude product of 1-O-(5,9,13,17-tetramethyloctadec-4-enyl)-D-glucopyranoside tetraacetate was dissolved in methanol/tetrahydrofuran (1:1, 50 mL), and 0.77 mL (0.77 mmol) of 1M sodium methylate in methanol was added thereto at room temperature. After being stirred for 24 hours, 55 μL (0.77 mmol) of acetyl chloride was added to the reaction mixture and then the mixture was confirmed to be neutralized. After addition of water, the solution was extracted with ethyl acetate. The extract was washed with saturated brine, and dried over anhydrous sodium sulfate. After filtration, the filtrate was concentrated, and the resulting residue was purified by silica gel column chromatography (methanol/methylene chloride mixture) to obtain 0.28 g of the title compound (7% yield in 2 steps) as a yellow viscous product. The results of NMR analysis of the thus obtained compound are as shown below.

$^1$H-NMR spectrum (300 MHz, CDCl$_3$, TMS) δ: 0.80-0.90 (m, 12H), 1.00-1.80 (m, 24H), 1.90-2.10 (m, 4H), 3.30-3.45 (m, 2H), 3.50-3.70 (m, 3H), 3.80-4.00 (m, 3H), 4.31 (d, J=7.7 Hz, 1H), 5.10 (brs, 1H).

Example 25

Synthesis of 1-O-(5,9,13,17-tetramethyloctadec-4-enyl)-D-galactoside

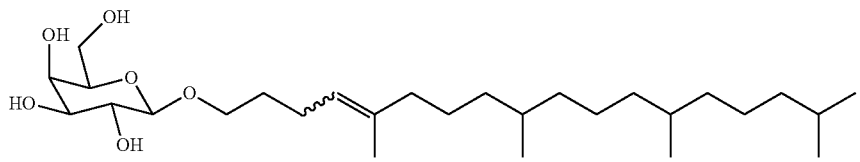 [SMILES: CC(=CCCCOC1OC(CO)C(O)C(O)C1O)CCCC(C)CCCC(C)CCCC(C)C]

The title compound was synthesized using the same procedure as employed in Example 24, but with 3.0 g (7.7 mmol) of D-galactose pentaacetate instead of (3-D-glucose pentaacetate, having the following properties:

$^1$H-NMR spectrum (300 MHz, CDCl$_3$, TMS) δ: 0.80-0.90 (m, 12H), 1.00-1.70 (m, 24H), 1.90-2.10 (m, 4H), 3.50-3.95 (m, 7H), 4.05 (brs, 1H), 4.25 (d, J=6.3 Hz, 1H), 5.10 (brs, 1H).

Example 26

Synthesis of 1-O-(5,9,13,17-tetramethyloctadec-4-enyl)-D-mannoside

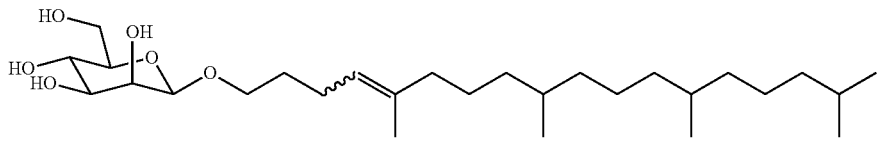 [SMILES: CC(=CCCCOC1OC(CO)C(O)C(O)C1O)CCCC(C)CCCC(C)CCCC(C)C]

The title compound was synthesized using the same procedure as employed in Example 24, but with 3.0 g (7.7 mmol) of D-mannose pentaacetate instead of 13-D-glucose pentaacetate, having the following properties:

$^1$H-NMR spectrum (300 MHz, CDCl$_3$, TMS) δ: 0.80-0.90 (m, 12H), 1.00-1.70 (m, 24H), 1.90-2.10 (m, 4H), 3.30-3.45 (m, 1H), 3.51 (d, J=9.1 Hz, 1H), 3.55-4.00 (m, 6H), 4.81 (s, 1H), 5.10 (brs, 1H).

Example 27

Synthesis of 1-O-(5,9,13,17-tetramethyloctadec-4-enyl)-D-maltoside

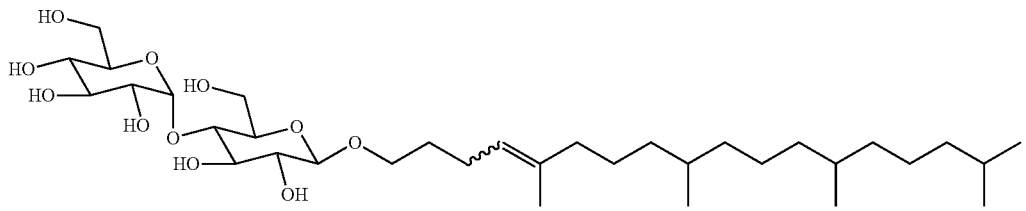 [SMILES: CC(=CCCCOC1OC(CO)C(OC2OC(CO)C(O)C(O)C2O)C(O)C1O)CCCC(C)CCCC(C)CCCC(C)C]

2.7 g (4.0 mmol) of D-maltose octaacetate and 1.0 g (3.1 mmol) of 5,9,13,17-tetramethyloctadec-4-en-1-ol were dissolved in dry acetonitrile (3 mL). 0.78 mL (6.2 mmol) of boron trifluoride diethyl etherate complex was added to the solution with cooling on ice. The reaction mixture was allowed to warm up slowly to room temperature while being stirred overnight before addition of 1.3 mL (9.2 mmol) of triethylamine at 0° C. The resulting solution was diluted with ethyl acetate, and washed with water, 1M hydrochloric acid, saturated sodium bicarbonate aqueous solution, and saturated brine, successively, and dried over sodium sulfate. After filtration, the filtrate was concentrated to obtain 1-O-(5,9,13,17-tetramethyloctadec-4-enyl)-D-maltoside heptaacetate as a crude product.

The above crude product of 1-O-(5,9,13,17-tetramethyloctadec-4-enyl)-D-maltoside heptaacetate was dissolved in methanol/tetrahydrofuran (1:1, 6 mL), and 0.31 mL (0.31 mmol) of 1M sodium methylate in methanol was added at room temperature. After being stirred for 24 hours, 22 µL (0.31 mmol) of acetyl chloride was added to the reaction mixture and then the mixture was conformed to be neutralized. The solution was concentrated, and the resulting residue was purified by silica gel column chromatography (methanol/methylene chloride mixture) to obtain the title compound. The results of NMR analysis of the thus obtained compound are as shown below.

$^1$H-NMR spectrum (300 MHz, CD$_3$OD, TMS) δ: 0.80-0.90 (m, 12H), 1.00-1.70 (m, 24H), 1.90-2.15 (m, 4H), 3.10-3.95 (m, 14H), 4.26 (d, J=7.7 Hz, 1H), 4.61 (s, 1H), 5.14 (brs, 1H).

Example 28

Synthesis of mono-O-(5,9,13,17-tetramethyloctadec-4-enyl)dipentaerythritol 1.28 mL (9.23 mmol) of triethylamine, 1.06 g (5.56 mmol) of p-toluenesulfonyl chloride, 43 mg (0.45 mmol) of trimethylamine hydrochloride were added to a solution of 1.50 g (4.63 mmol) of 5,9,13,17-tetramethyloctadec-4-en-1-ol in dry methylene chloride (9 mL) was added, at 0° C., sequentially. After being stirred for 3 hours at room temperature, 0.14 mL (1.1 mmol) of N,N-dimethyl-1,3-propanediamine was added to the reaction mixture at 0° C. After being stirred for 3 hours, the mixture was diluted with ethyl acetate. The resulting solution was washed with water, 1M hydrochloric acid, saturated sodium bicarbonate aqueous solution, and saturated brine, successively, and dried over anhydrous sodium sulfate. After filtration, the filtrate was concentrated to obtain (5,9,13,17-tetramethyloctadec-4-enyl)tosylate as a crude product.

0.37 g (60%, 9.2 mmol) of sodium hydride was added to a solution of 2.35 g (9.24 mmol) of dipentaerythritol in dry N,N-dimethylformamide (6 mL) with cooling on ice. After the mixture was stirred for 1 hour at 50° C., the above (5,9,13,17-tetramethyloctadec-4-enyl)tosylate was added dropwise thereto, with additional stirring for 20 hours at 60° C. After addition of water at 0° C., the reaction mixture was extracted with ethyl acetate. The extract was washed with water, 1M hydrochloric acid, saturated sodium bicarbonate aqueous solution, and saturated brine, successively, and dried over anhydrous sodium sulfate. After filtration, the filtrate was concentrated, and the resulting residue was purified by silica gel column chromatography (methanol/methylene chloride mixture) to obtain 494 mg of the title compound (19% yield in 2 steps) as a white solid. The results of NMR analysis of the thus obtained compound are as shown below.

$^1$H-NMR spectrum (300 MHz, CDCl$_3$+3% CD$_3$OD, TMS) δ: 0.80-0.90 (m, 12H), 1.00-1.70 (m, 24H), 1.90-2.10 (m, 4H), 3.35-3.70 (m, 18H), 5.09 (t, J=6.6 Hz, 1H).

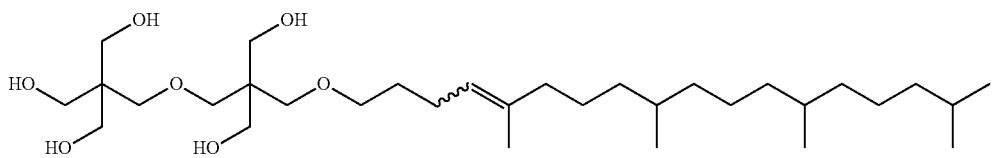 [SMILES: CC(=CCCCOCC(CO)(CO)COCC(CO)(CO)CO)CCCC(C)CCCC(C)CCCC(C)C]

Example 29

Synthesis of mono-O-(5,9,13,17-tetramethyloctadec-4-enyl)sorbitol

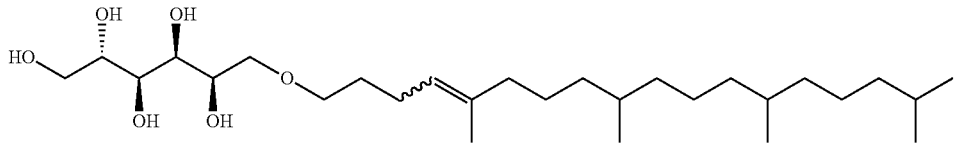 [SMILES: CC(=CCCCOC[C@@H](O)[C@H](O)[C@@H](O)[C@@H](O)CO)CCCC(C)CCCC(C)CCCC(C)C]

The title compound was synthesized using the same procedure as employed in Example 28, but with 1.68 g (9.24 mmol) of sorbitol instead of dipentaerythritol. The compound was obtained as a colorless transparent viscous product (679 mg; 30% yield in 2 steps) having the following properties:

$^1$H-NMR spectrum (300 MHz, CDCl$_3$, TMS) δ: 0.80-0.90 (m, 12H), 1.00-1.70 (m, 24H), 1.97-2.10 (m, 4H), 3.40-4.00 (m, 10H), 5.09 (brs, 1H).

Example 30

Synthesis of mono-O-(5,9,13,17-tetramethyloctadec-4-enyl)mannitol

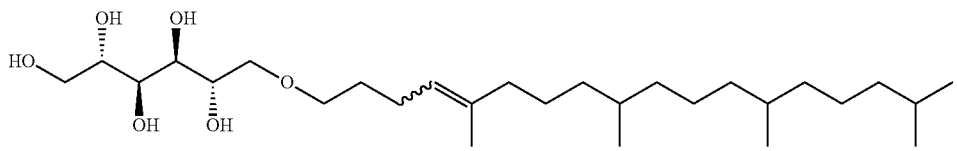 [SMILES: CC(=CCCCOC[C@H](O)[C@H](O)[C@@H](O)[C@@H](O)CO)CCCC(C)CCCC(C)CCCC(C)C]

The title compound was synthesized using the same procedure as employed in Example 28, but with 1.68 g (9.24 mmol) of mannitol instead of dipentaerythritol. The compound was obtained as a yellow viscous product (544 mg; 24% in 2 steps) having the following properties:

$^1$H-NMR spectrum (300 MHz, CDCl$_3$, TMS) δ: 0.80-0.90 (m, 12H), 1.00-1.70 (m, 24H), 1.90-2.10 (m, 4H), 3.20-3.95 (m, 10H), 5.08 (brs, 1H).

Example 31

Synthesis of mono-O-(5,9,13,17-tetramethyloctadec-4-enyl)glycerol

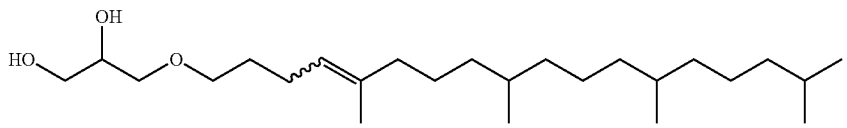 [SMILES: CC(=CCCCOCC(O)CO)CCCC(C)CCCC(C)CCCC(C)C]

The title compound was synthesized using the same procedure as employed in Example 28, but with 0.851 g (9.24 mmol) of glycerol instead of dipentaerythritol, having the following properties:

$^1$H-NMR spectrum (300 MHz, CDCl$_3$, TMS) δ: 0.80-0.90 (m, 12H), 1.00-1.70 (m, 24H), 1.90-2.10 (m, 4H), 2.19 (dd, J=4.8, 7.2 Hz, 1H, OH), 2.63 (d, J=5.1 Hz, 1H, OH), 3.40-3.90 (m, 7H), 5.10 (t, J=7.2 Hz, 1H).

Example 32

Synthesis of mono-O-(5,9,13,17-tetramethyloctadec-4-enyl)diglycerol

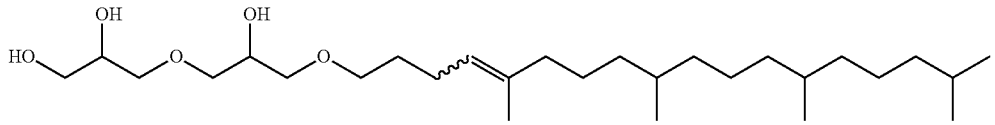 [SMILES: CC(=CCCCOCC(O)COCC(O)CO)CCCC(C)CCCC(C)CCCC(C)C]

The title compound was synthesized using the same procedure as employed in Example 28, but with 1.54 g (9.24 mmol) of diglycerol instead of dipentaerythritol, having the following properties:

$^1$H-NMR spectrum (300 MHz, CDCl$_3$, TMS) δ: 0.80-0.90 (m, 12H), 1.00-1.70 (m, 24H), 1.90-2.10 (m, 4H), 3.40-4.00 (m, 12H), 5.10 (t, J=7.1 Hz, 1H).

Example 33

Synthesis of mono-O-(5,9,13,17-tetramethyloctadec-4-enyl)triglycerol

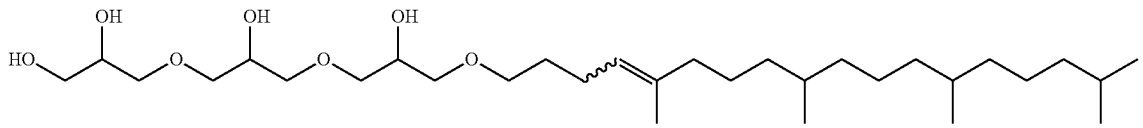 [SMILES: CC(=CCCCOCC(O)COCC(O)COCC(O)CO)CCCC(C)CCCC(C)CCCC(C)C]

The title compound was synthesized using the same procedure as employed in Example 28, but with 2.22 g (9.24 mmol) of triglycerol instead of dipentaerythritol, having the following properties:

$^1$H-NMR spectrum (300 MHz, CDCl$_3$, TMS) δ: 0.80-0.90 (m, 12H), 1.00-1.70 (m, 24H), 1.90-2.10 (m, 4H), 3.40-4.20 (m, 17H), 5.10 (brs, 1H).

Example 34

Synthesis of mono-O-(5,9,13,17-tetramethyloctadec-4-enyl)xylitol

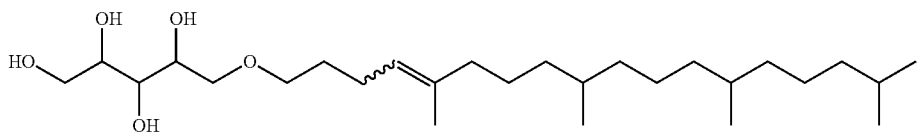 [SMILES: CC(=CCCCOCC(O)C(O)C(O)CO)CCCC(C)CCCC(C)CCCC(C)C]

The title compound was synthesized using the same procedure as employed in Example 28, but with 1.41 g (9.24 mmol) of xylitol instead of dipentaerythritol, having the following properties:

$^1$H-NMR spectrum (300 MHz, CDCl$_3$, TMS) δ: 0.80-0.90 (m, 12H), 1.00-1.70 (m, 24H), 1.90-2.10 (m, 4H), 3.49 (td, J=2.7, 6.6 Hz, 2H), 3.60 (d, J=4.4 Hz, 2H), 3.65-3.90 (m, 4H), 3.93 (m, 1H), 5.09 (t, J=7.5 Hz, 1H).

Example 35

Synthesis of mono-O-(5,9,13,17-tetramethyloctadec-4-enyl)ascorbic acid

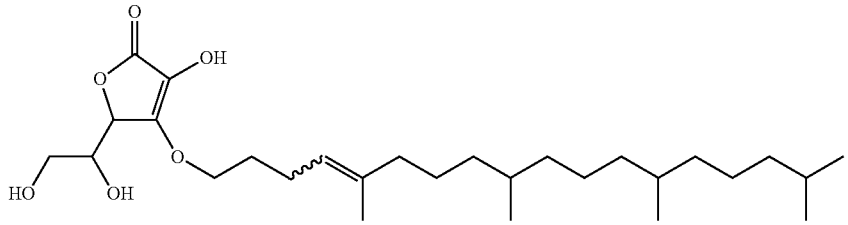 [SMILES: CC(=CCCCOC1=C(O)C(=O)OC1C(O)CO)CCCC(C)CCCC(C)CCCC(C)C]

1.28 mL (9.23 mmol) of triethylamine, 1.06 g (5.56 mmol) of p-toluenesulfonyl chloride, 43 mg (0.45 mmol) of trimethylamine hydrochloride were added to a solution of 1.50 g (4.63 mmol) of 5,9,13,17-tetramethyloctadec-4-en-1-ol in dry methylene chloride (9 mL) at 0° C., sequentially. After being stirred for 3 hours at room temperature, 0.14 mL (1.1 mmol) of N,N-dimethyl-1,3-propanediamine was added to the reaction mixture at 0° C. After being stirred for 3 hours, the mixture was diluted with ethyl acetate. The resulting solution was washed with water, 1M hydrochloric acid, saturated sodium bicarbonate aqueous solution, and saturated brine, successively, and dried over anhydrous sodium sulfate. After filtration, the filtrate was concentrated to obtain (5,9,13,17-tetramethyloctadec-4-enyl)tosylate as a crude product.

0.71 mL (5.1 mmol) of triethylamine was added and dissolved in a suspension of 0.82 g (4.63 mmol) of ascorbic acid in acetonitrile (9 mL). The above crude product of (5,9,13,17-tetramethyloctadec-4-enyl)tosylate was added at room temperature, and the reaction mixture was heated for 2 hours at 90° C. The reaction mixture was concentrated, and the resulting residue was purified by silica gel column chromatography (methanol/methylene chloride mixture) to obtain the title compound.

Example 36

Synthesis of 3,7,11,15-tetramethylhexadec-2-ene-1-nitrile

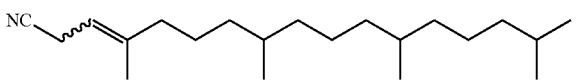 [SMILES: CC(=CCC#N)CCCC(C)CCCC(C)CCCC(C)C]

90.1 g (0.674 mol) of N-Chlorosuccinimide was suspended in methylene chloride (840 mL). After addition of 52.4 mL (0.708 mol) of dimethylsulfide at 0° C., the solution was stirred for 20 min. After addition of 100 g (0.337 mol) of phytol, the mixture was stirred for 1 hour at 0° C., with additional stirring for 6 hours at room temperature. The reaction mixture was diluted with saturated sodium bicarbonate aqueous solution, and extracted with methylene chloride. The extract was washed with saturated brine, and dried over anhydrous sodium sulfate. After filtration, the filtrate was concentrated to obtain 3,7,11,15-tetramethylhexadec-2-ene-1-chloride as a crude product.

19.8 g (0.405 mol) of sodium cyanide was added to a solution of the thus obtained crude product in N,N-dimethylformamide (560 mL). The solution was stirred for 10 hours at room temperature. After addition of water at 0° C., the reaction mixture was extracted with a mixed solvent of ether/hexane. The extract was washed with saturated sodium bicarbonate aqueous solution and saturated brine, successively, and dried over sodium sulfate. After filtration, the filtrate was concentrated, and the resulting residue was purified by silica gel column chromatography (ethyl acetate/hexane mixture) to obtain 88.9 g of the title compound (86% in 2 steps) as a yellow liquid. The results of NMR analysis of the obtained compound are as shown below.

$^1$H-NMR spectrum (300 MHz, CDCl$_3$, TMS) δ: 0.80-0.90 (m, 12H), 1.00-1.55 (m, 19H), 1.66 and 1.74 (s, 3H, 3-CH$_3$), 2.00 (t, J=7.7 Hz, 2H), 3.04 (d, J=7.0 Hz, 2H), 5.16 (t, J=7.0 Hz, 1H).

Example 37

Synthesis of methyl 4,8,12,16-tetramethylheptadec-3-enoate

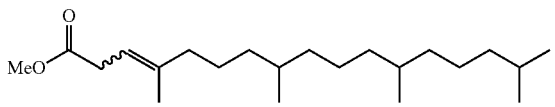 [SMILES: COC(=O)CC=C(C)CCCC(C)CCCC(C)CCCC(C)C]

Water (115 mL) and 35.5 g (0.63 mol) of potassium hydroxide were added to a solution of 77 g (0.25 mol) of 3,7,11,15-tetramethylhexadec-2-ene-1-nitrile in ethanol (345 mL). The solution was stirred for 18 hours at 80° C. The reaction mixture was concentrated, and neutralized with 3M hydrochloric acid, and then extracted with ethyl acetate. The extract was washed with saturated brine, and dried over sodium sulfate. After filtration, the filtrate was concentrated to obtain 88 g of 4,8,12,16-tetramethylheptadec-3-enoic acid as a crude product.

The thus obtained crude product of 4,8,12,16-tetramethylheptadec-3-enoic acid was dissolved in methanol (400 mL), and concentrated sulfuric acid (8 mL) was added at room temperature. After being stirred for 12 hours, sodium bicarbonate was added slowly to the reaction mixture and the mixture was confirmed to be neutralized. After filtration, the filtrate was concentrated, and the residue was diluted with ethyl acetate. The solution was washed with water and saturated brine, successively, and dried over anhydrous sodium sulfate. After filtration, the filtrate was concentrated, and the resulting residue was purified by silica gel column chromatography (ethyl acetate/hexane mixture) to obtain 65.2 g of the title compound (77% in 2 steps) as a slightly yellow liquid. The results of NMR analysis of the obtained compound are as shown below.

$^1$H-NMR spectrum (300 MHz, CDCl$_3$, TMS) δ: 0.80-0.90 (m, 12H), 1.00-1.60 (m, 19H), 1.62 and 1.73 (s, 3H, 4-CH$_3$), 2.00 (t, J=7.5 Hz, 2H), 3.05 (d, J=6.5 Hz, 2H), 3.68 (s, 3H), 5.31 (t, J=6.5 Hz, 1H).

Example 38

Synthesis of 4,8,12,16-tetramethylheptadec-3-en-1-ol

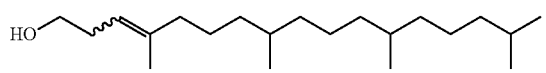 [SMILES: CC(=CCCO)CCCC(C)CCCC(C)CCCC(C)C]

Under a nitrogen atmosphere, 9.8 g (0.26 mol) of lithium aluminum hydride was added little by little at 0° C. to a solution of 35 g (0.10 mol) of methyl 4,8,12,16-tetramethyl-heptadec-3-enoate in dry tetrahydrofuran (250 mL). After being stirred at 50° C. for 3 hours, the reaction mixture was cooled on ice, followed by careful addition of saturated sodium sulfate aqueous solution until the resulting gray suspension turned white. Sodium sulfate was added to the solution at room temperature for drying. After filtration, the filtrate was concentrated to obtain 28.7 g of the title compound (92% yield) as a colorless transparent liquid. The results of NMR analysis of the obtained compound are as shown below.

$^1$H-NMR spectrum (300 MHz, CDCl$_3$, TMS) δ: 0.80-0.90 (m, 12H), 1.00-1.60 (m, 19H), 1.64 and 1.72 (s, 3H, 4-CH$_3$), 1.95-2.05 (m, 2H), 2.29 (td, J=6.5, 7.3 Hz, 2H), 3.63 (t, J=6.5 Hz, 2H), 5.12 (t, J=7.3 Hz, 1H).

Example 39

Synthesis of mono-O-(4,8,12,16-tetramethylheptadec-3-enoyl)glycerol

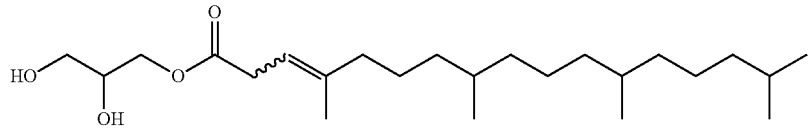 [SMILES: CC(=CCC(=O)OCC(O)CO)CCCC(C)CCCC(C)CCCC(C)C]

1.0 g (3.0 mmol) of methyl 4,8,12,16-tetramethylheptadec-3-enoate was slowly added dropwise to a solution of 0.68 g (7.4 mmol) of glycerol and 0.61 g (4.4 mmol) of potassium carbonate in dry N,N-dimethylformamide (3.5 mL) at 100° C. After the reaction mixture was stirred at 100° C. for 18 hours, 1M hydrochloric acid was added. The reaction solution was extracted with ether, and the extract was washed with saturated sodium bicarbonate aqueous solution and saturated brine, successively, and dried over anhydrous sodium sulfate. After filtration, the filtrate was concentrated, and the resulting residue was purified by silica gel column chromatography (ethyl acetate/hexane mixture) to obtain 347 mg of the title compound (29% yield) as a yellow viscous product.

The results of 1H-NMR analysis of the obtained compound are as shown below.

$^1$H-NMR spectrum (300 MHz, CDCl$_3$, TMS) δ: 0.80-0.90 (m, 12H), 1.00-1.60 (m, 19H), 1.63 and 1.74 (s, 3H, 4-CH$_3$), 2.00 (t, J=7.4 Hz, 2H), 3.10 (d, J=7.2 Hz, 2H), 3.55-4.00 (m, 3H), 4.10-4.30 (m, 2H), 5.30 (t, J=7.2 Hz, 1H).

Example 40

Synthesis of mono-O-(4,8,12,16-tetramethylheptadec-3-enoyl)erythritol

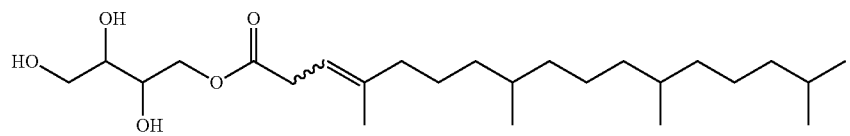 [SMILES: CC(=CCC(=O)OCC(O)C(O)CO)CCCC(C)CCCC(C)CCCC(C)C]

The title compound was synthesized using the same procedure as employed in Example 39, but with 0.90 g (7.4 mmol) of erythritol instead of glycerol. The compound was obtained (270 mg, 21% yield) having the following properties:

$^1$H-NMR spectrum (300 MHz, CDCl$_3$, TMS) δ: 0.80-0.90 (m, 12H), 1.00-1.60 (m, 19H), 1.63 and 1.74 (s, 3H, 4-CH$_3$), 2.00 (t, 77.8 Hz, 2H), 2.13 (brs, 1H, OH), 2.67 (d, J=5.3 Hz, 1H, OH), 2.80 (d, J=5.8 Hz, 1H, OH), 3.12 (d, J=7.2 Hz, 2H), 3.65-3.95 (m, 4H), 4.30-4.40 (m, 2H), 5.31 (t, J=7.2 Hz, 1H).

Example 41

Synthesis of mono-O-(4,8,12,16-tetramethylheptadec-3-enoyl)pentaerythritol

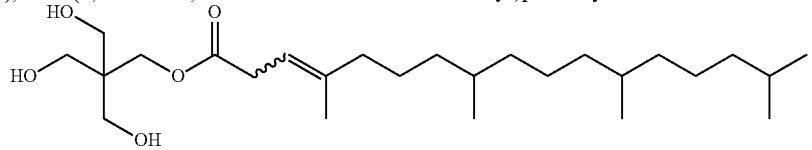

The title compound was synthesized using the same procedure as employed in Example 39, but with 1.0 g (7.4 mmol) of pentaerythritol instead of glycerol. The compound was obtained (408 mg, 32% yield) having the following properties:

$^1$H-NMR spectrum (300 MHz, CDCl$_3$, TMS) δ: 0.80-0.90 (m, 12H), 1.00-1.60 (m, 19H), 1.64 and 1.74 (s, 3H, 4-CH$_3$), 2.00 (1, J=7.4 Hz, 2H), 2.56 (brs, 3H, OH), 3.10 (d, J=7.2 Hz, 2H), 3.64 (brs, 6H), 4.23 (s, 2H), 5.29 (t, J=7.2 Hz, 1H).

Example 42

Synthesis of mono-O-(4,8,12,16-tetramethylheptadec-3-enoyl)diglycerol

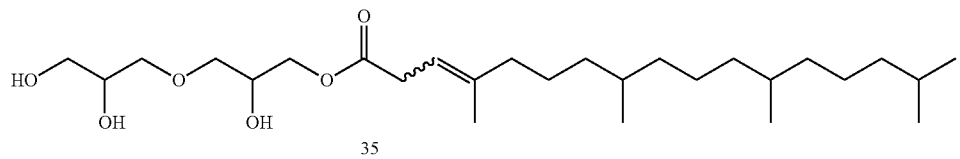

1.0 g (3.0 mmol) of methyl 4,8,12,16-tetramethylheptadec-3-enoate was slowly added dropwise to a solution of 1.23 g (4.38 mmol) of diglycerol and 0.61 g (4.4 mmol) of potassium carbonate in dry N,N-dimethylformamide (3.5 mL) at 100° C. After the reaction mixture was stirred at 100° C. for 18 hours, 1M hydrochloric acid was added. The reaction solution was extracted with ethyl acetate, and the extract was washed with saturated sodium bicarbonate aqueous solution and saturated brine, successively, and dried over anhydrous sodium sulfate. After filtration, the filtrate was concentrated, and the resulting residue was purified by silica gel column chromatography (methanol/methylene chloride mixture) to obtain 153 mg of the title compound (11% yield).

The results of 1H-NMR analysis of the obtained compound are as shown below.

$^1$H-NMR spectrum (300 MHz, CDCl$_3$, TMS) δ: 0.80-0.90 (m, 12H), 1.00-1.60 (m, 19H), 1.62 and 1.73 (s, 3H, 4-CH$_3$), 2.02 (t, J=7.8 Hz, 2H), 3.09 (d, J=7.0 Hz, 2H), 3.50-4.30 (m, 10H), 5.31 (t, J=7.0 Hz, 1H).

Example 43

Synthesis of mono-O-(4,8,12,16-tetramethylheptadec-3-enoyl)triglycerol

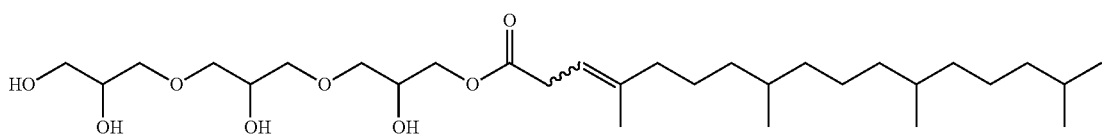 [SMILES: CC(=CCC(=O)OCC(O)COCC(O)COCC(O)CO)CCCC(C)CCCC(C)CCCC(C)C]

The title compound was synthesized using the same procedure as employed in Example 42, but with 1.77 g (7.38 mmol) of triglycerol instead of diglycerol. The compound was obtained (138 mg, 8% yield) having the following properties:

$^1$H-NMR spectrum (300 MHz, CDCl$_3$, TMS) δ: 0.80-0.90 (m, 12H), 1.00-1.60 (m, 19H), 1.62 and 1.73 (s, 3H, 4-CH$_3$), 1.99 (t, J=7.1 Hz, 2H), 3.09 (d, J=6.9 Hz, 2H), 3.50-4.25 (m, 15H), 5.31 (t, J=6.9 Hz, 1H).

Example 44

Synthesis of mono-O-(4,8,12,16-tetramethylheptadec-3-enoyl)xylitol

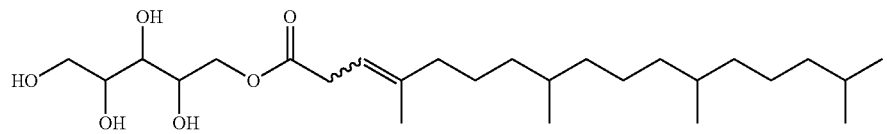 [SMILES: CC(=CCC(=O)OCC(O)C(O)C(O)CO)CCCC(C)CCCC(C)CCCC(C)C]

The title compound was synthesized using the same procedure as employed in Example 42, but with 1.12 g (7.38 mmol) of xylitol instead of diglycerol. The compound was obtained (215 mg, 16% yield) having the following properties:

$^1$H-NMR spectrum (300 MHz, CDCl$_3$, TMS) δ: 0.80-0.90 (m, 12H), 1.00-1.60 (m, 19H), 1.62 and 1.74 (s, 3H, 4-CH$_3$), 2.00 (t, J=7.6 Hz, 2H), 3.10 (d, J=7.1 Hz, 2H), 3.60-4.10 (m, 5H), 4.24 (d, J=5.7 Hz, 2H), 5.29 (t, J=7.1 Hz, 1H).

Example 45

Synthesis of mono-O-(4,8,12,16-tetramethylheptadec-3-enoyl)mannitol

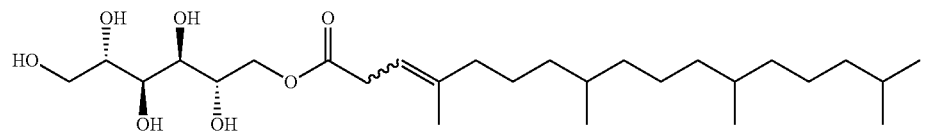 [SMILES: CC(=CCC(=O)OC[C@H](O)[C@H](O)[C@@H](O)[C@@H](O)CO)CCCC(C)CCCC(C)CCCC(C)C]

The title compound was synthesized using the same procedure as employed in Example 42, but with 1.35 g (7.38 mmol) of mannitol instead of diglycerol. The compound was obtained (375 mg, 26% yield) having the following properties:

$^1$H-NMR spectrum (300 MHz, CDCl$_3$, TMS) δ: 0.80-0.90 (m, 12H), 1.00-1.55 (m, 19H), 1.60 and 1.72 (s, 3H, 4-CH$_3$), 1.97 (brt, 2H), 3.11 (d, J=5.7 Hz, 2H), 3.60-4.50 (m, 8H), 5.29 (t, J=5.7 Hz, 1H).

Example 46

Synthesis of mono-O-(4,8,12,16-tetramethylheptadec-3-enoyl)sorbitol

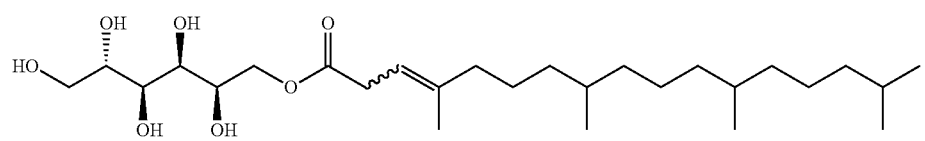 [SMILES: CC(=CCC(=O)OC[C@@H](O)[C@H](O)[C@@H](O)[C@@H](O)CO)CCCC(C)CCCC(C)CCCC(C)C]

The title compound was synthesized using the same procedure as employed in Example 42, but with 1.35 g (7.38 mmol) of sorbitol instead of diglycerol. The compound was obtained (310 mg, 21% yield) having the following properties:

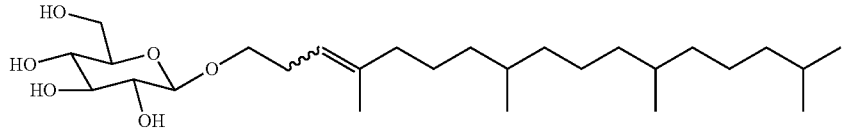

$^1$H-NMR spectrum (300 MHz, CDCl$_3$, TMS) δ: 0.80-0.90 (m, 12H), 1.00-1.60 (m, 19H), 1.61 and 1.72 (s, 3H, 4-CH$_3$), 1.98 (brt, 2H), 3.10 (brs, 2H), 3.60-4.50 (m, 8H), 5.29 (brs, 1H).

Example 47

Synthesis of mono-O-(4,8,12,16-tetramethylheptadec-3-enoyl)dipentaerythritol

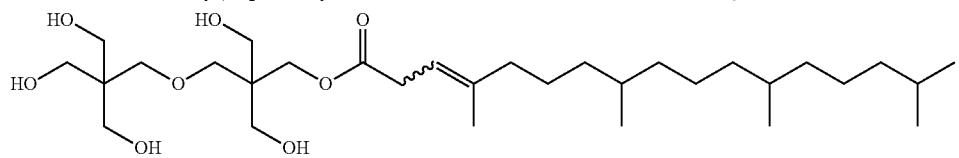

The title compound was synthesized using the same procedure as employed in Example 42, but with 1.88 g (7.38 mmol) of dipentaerythritol instead of diglycerol. The compound was obtained (144 mg, 9% yield) having the following properties:

$^1$H-NMR spectrum (300 MHz, CDCl$_3$, TMS) δ: 0.80-0.90 (m, 12H), 1.00-1.60 (m, 19H), 1.63 and 1.74 (s, 3H, 4-CH$_3$), 2.00 (t, J=7.8 Hz, 2H), 3.08 (d, J=7.0 Hz, 2H), 3.38 (d, J=8.3 Hz, 4H), 3.50-3.60 (m, 10H), 4.07 (s, 2H), 5.28 (t, J=7.0 Hz, 1H).

Example 48

Synthesis of mono-O-(4,8,12,16-tetramethylheptadec-3-enoyl)ascorbic acid

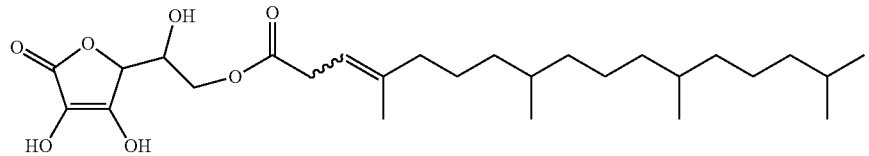 [SMILES: CC(=CCC(=O)OCC(O)C1OC(=O)C(O)=C1O)CCCC(C)CCCC(C)CCCC(C)C]

0.53 g (3.0 mmol) of ascorbic acid was dissolved in concentrated sulfuric acid (14 mL). After addition of 1.0 g (3.0 mmol) of methyl 4,8,12,16-tetramethylheptadec-3-enoate, the mixture was stirred for 24 hours at room temperature. The reaction mixture was poured into iced water, and extracted with ethyl acetate. The extract was washed with water, 1M hydrochloric acid, saturated sodium bicarbonate aqueous solution, and saturated brine, successively, and dried over anhydrous sodium sulfate. After filtration, the filtrate was concentrated, and the resulting residue was purified by silica gel column chromatography (methanol/methylene chloride mixture) to obtain the title compound.

Example 49

Synthesis of 1-O-(4,8,12,16-tetramethylheptadec-3-enyl)-D-glucoside 1.63 g (4.19 mmol) of 13-D-Glucose pentaacetate and 1.0 g (3.2 mmol) of 4,8,12,16-tetramethylheptadec-3-en-1-ol were dissolved in dry acetonitrile (3 mL). 0.82 mL (6.4 mmol) of boron trifluoride diethyl etherate complex was added to the solution with cooling on ice. The reaction mixture was allowed to warm up slowly to room temperature while being stirred for 18 hours before addition of 1.3 mL (9.7 mmol) of triethylamine at 0° C. The resulting solution was diluted with ethyl acetate, and washed with water, 1M hydrochloric acid, saturated sodium bicarbonate aqueous solution, and saturated brine, successively, and dried over sodium sulfate. After filtration, the filtrate was concentrated to obtain 1-O-(4,8,12,16-tetramethylheptadec-3-enyl)-D-glucopyranoside tetraacetate as a crude product.

The above obtained crude product of 1-O-(4,8,12,16-tetramethylheptadec-3-enyl)-D-glucopyranoside tetraacetate was dissolved in methanol/tetrahydrofuran (1:1, 6 mL), and 0.32 mL (0.32 mmol) of 1M sodium methylate in methanol was added at room temperature. After being stirred for 24 hours, 25 μl, (0.35 mmol) of acetyl chloride was added to the reaction mixture and the mixture was confirmed to be neutralized. After addition of water, the solution was extracted with ethyl acetate. The extract was washed with saturated brine, and dried over anhydrous sodium sulfate. After filtration, the filtrate was concentrated, and the resulting residue was purified by silica gel column chromatography (methanol/methylene chloride mixture) to obtain the title compound. The results of NMR analysis of the obtained compound are as shown below.

$^1$H-NMR spectrum (300 MHz, CDCl$_3$, TMS) δ: 0.80-0.90 (m, 12H), 1.00-1.80 (m, 22H), 1.90-2.15 (m, 4H), 3.30-3.90 (m, 8H), 4.31 (brs, 1H), 5.13 (brs, 1H).

Example 50

Synthesis of 1-O-(4,8,12,16-tetramethylheptadec-3-enyl)-D-xylopyranoside

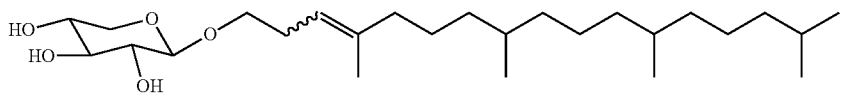 [SMILES: CC(=CCCOC1OCC(O)C(O)C1O)CCCC(C)CCCC(C)CCCC(C)C]

The title compound was synthesized using the same procedure as employed in Example 49, but with 1.33 g (4.19 mmol) of D-xylose tetraacetate instead of 13-D-glucose pentaacetate, having the following properties:

¹H-NMR spectrum (300 MHz, CDCl₃, TMS) δ: 0.80-0.90 (m, 12H), 1.00-1.80 (m, 22H), 1.85-2.15 (m, 4H), 3.30-4.10 (m, 7H), 4.38 (d, J=5.1 Hz, 0.5H), 4.89 (d, d=3.9 Hz, 0.5H), 5.11 (t, J=6.0 Hz, 1H).

Example 51

Synthesis of 1-O-(4,8,12,16-tetramethylheptadec-3-enyl)-D-galactoside

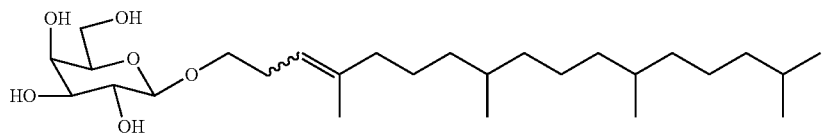 [SMILES: CC(=CCCOC1OC(CO)C(O)C(O)C1O)CCCC(C)CCCC(C)CCCC(C)C]

The title compound was synthesized using the same procedure as employed in Example 49, but with 1.63 g (4.19 mmol) of D-galactose pentaacetate instead of (3-D-glucose pentaacetate, having the following properties:

¹H-NMR spectrum (300 MHz, CDCl₃, TMS) δ: 0.80-0.90 (m, 12H), 1.00-1.80 (m, 22H), 1.85-2.10 (m, 4H), 3.40-4.10 (m, 9H), 4.26 (brs, 1H), 5.00-5.10 (m, 1H).

Example 52

Synthesis of 1-O-(4,8,12,16-tetramethylheptadec-3-enyl)-D-mannoside

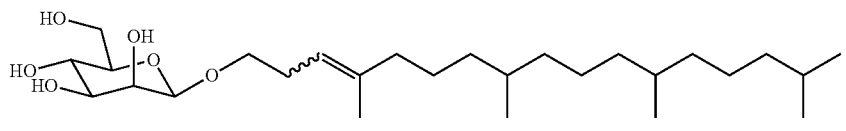 [SMILES: CC(=CCCOC1OC(CO)C(O)C(O)C1O)CCCC(C)CCCC(C)CCCC(C)C]

The title compound was synthesized using the same procedure as employed in Example 49, but with 1.63 g (4.19 mmol) of D-mannose pentaacetate instead of 13-D-glucose pentaacetate, having the following properties:

¹H-NMR spectrum (300 MHz, CDCl₃, TMS) δ: 0.80-0.90 (m, 12H), 1.00-1.85 (m, 22H), 1.85-2.05 (m, 4H), 3.30-4.20 (m, 8H), 4.79 (d, J=7.2 Hz, 1H), 5.07 (brs, 1H).

Example 53

Synthesis of 1-O-(4,8,12,16-tetramethylheptadec-3-enyl)-D-maltoside

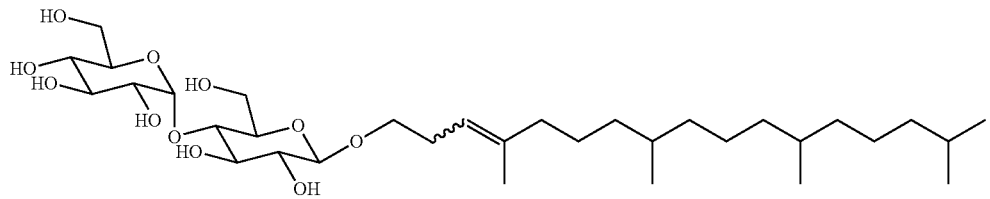 [SMILES: CC(=CCCOC1OC(CO)C(OC2OC(CO)C(O)C(O)C2O)C(O)C1O)CCCC(C)CCCC(C)CCCC(C)C]

2.84 g (4.19 mmol) of D-maltose octaacetate and 1.0 g (3.2 mmol) of 4,8,12,16-tetramethylheptadec-3-en-1-ol was dissolved in dry acetonitrile (3 mL). 0.82 mL (6.4 mmol) of boron trifluoride diethyl etherate complex was added to the solution with cooling on ice. The reaction mixture was allowed to warm up slowly to room temperature while being stirred 18 hours before addition of 1.34 mL (9.66 mmol) of triethylamine at 0° C., The resulting solution was diluted with ethyl acetate, and washed with water, 1M hydrochloric acid, saturated sodium bicarbonate aqueous solution, and saturated brine, successively, and dried over sodium sulfate. After filtration, the filtrate was concentrated to obtain 1-O-(4,8,12,16-tetramethylheptadec-3-enyl)-D-maltoside heptaacetate as a crude product.

The above obtained crude product of 1-O-(4,8,12,16-tetramethylheptadec-3-enyl)-D-maltoside heptaacetate was dissolved in methanol/tetrahydrofuran (1:1, 4 mL), and 0.42 mL (0.42 mmol) of 1M sodium methylate in methanol was added at room temperature. After being stirred for 24 hours, 55 μL (0.77 mmol) of acetyl chloride was added to the reaction mixture and the mixture was confirmed to be neutralized. The solution was concentrated, and the resulting residue was purified by silica gel column chromatography (methanol/methylene chloride mixture) to obtain the title compound. The results of NMR analysis of the obtained compound are as shown below.

$^1$H-NMR spectrum (300 MHz, CD$_3$OD, TMS) δ: 0.80-0.90 (m, 12H), 1.00-1.70 (m, 22H), 1.90-2.10 (m, 4H), 3.15-3.90 (m, 14H), 4.20-4.30 (m, 1H), 4.60 (brs, 1H), 5.13 (brs, 2H).

Example 54

Synthesis of mono-O-(4,8,12,16-tetramethylheptadec-3-enyl)glycerol

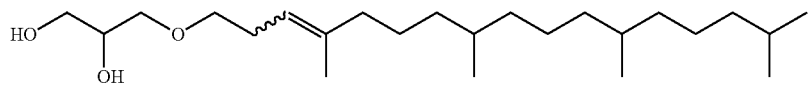 [SMILES: CC(=CCCOCC(O)CO)CCCC(C)CCCC(C)CCCC(C)C]

Under a nitrogen atmosphere, 0.49 mL (3.5 mmol) of triethylamine, 0.68 g (3.54 mmol) of p-toluenesulfonyl chloride, and 15 mg (0.16 mmol) of trimethylamine hydrochloride were added to a solution of 1.0 g (3.2 mmol) of 4,8,12,16-tetramethylheptadec-3-en-1-ol in dry methylene chloride (3.2 mL) at 0° C., sequentially. After being stirred for 2 hours at room temperature, 0.080 mL (0.64 mmol) of N,N-dimethyl-1,3-propanediamine was added to the reaction mixture at 0° C. After being stirred for 15 min, water was added, and the mixture was extracted with methylene chloride. The extract was washed with 1M hydrochloric acid, saturated sodium bicarbonate aqueous solution, and saturated brine, successively, and dried over anhydrous sodium sulfate. After filtration, the filtrate was concentrated to obtain (4,8,12,16-tetramethylheptadec-3-enyl)tosylate as a crude product.

0.21 g (55%, 4.8 mmol) of sodium hydride was added to a solution of 0.44 g (4.8 mmol) of glycerol in dry N,N-dimethylformamide (5 mL) with cooling on ice. After the mixture was stirred for 30 min at 50° C., the above (4,8,12,16-tetramethylheptadec-3-enyl)tosylate was added dropwise with additional stirring for 12 hours at the same temperature. After addition of water at 0° C., the reaction mixture was extracted with ethyl acetate. The extract was washed with water, 1M hydrochloric acid, saturated sodium bicarbonate aqueous solution, and saturated brine, successively, and dried over anhydrous sodium sulfate. After filtration, the filtrate was concentrated, and the residue was purified by silica gel column chromatography (ethyl acetate/hexane mixture) to obtain 44 mg of the title compound (4% yield in 2 steps) as a colorless transparent viscous product. The results of NMR analysis of the obtained compound are as shown below.

$^1$H-NMR spectrum (300 MHz, CDCl$_3$, TMS) δ: 0.80-0.90 (m, 12H), 1.00-1.60 (m, 19H), 1.61 and 1.69 (s, 3H, 4-CH$_3$), 1.96 (t, J=7.6 Hz, 2H), 2.30 (m, 2H), 3.40-3.90 (m, 7H), 5.12 (m, 1H).

Example 55

Synthesis of mono-O-(4,8,12,16-tetramethylheptadec-3-enyl)erythritol

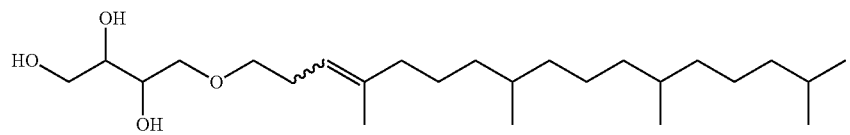 [SMILES: CC(=CCCOCC(O)C(O)CO)CCCC(C)CCCC(C)CCCC(C)C]

The title compound was synthesized using the same procedure as employed in Example 54, but with 0.59 g (4.8 mmol) of erythritol instead of glycerol, having the following properties:

$^1$H-NMR spectrum (300 MHz, CDCl$_3$, TMS) δ: 0.80-0.90 (m, 12H), 1.00-1.60 (m, 19H), 1.61 and 1.69 (s, 3H, 4-CH$_3$), 1.90-2.05 (m, 2H), 2.29 (td, J=6.5 Hz, 2H), 2.64 (brs, 1H, OH), 2.74 (brs, 1H, OH), 3.45-3.51 (m, 2H), 3.55-3.68 (m, 2H), 3.70-3.85 (m, 4H), 5.10 (t, J=6.5 Hz, 1H).

Example 56

Synthesis of mono-O-(4,8,12,16-tetramethylheptadec-3-enyl)pentaerythritol

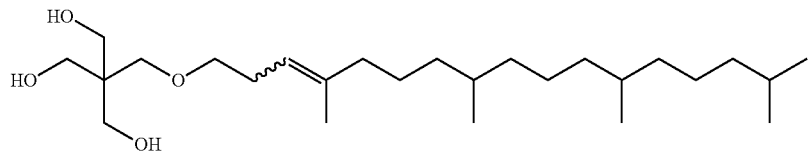 [SMILES: CC(=CCCOCC(CO)(CO)CO)CCCC(C)CCCC(C)CCCC(C)C]

The title compound was synthesized using the same procedure as employed in Example 54, but with 0.66 g (4.8 mmol) of pentaerythritol instead of glycerol. The compound was obtained (193 mg, 17% yield in 2 steps) having the following properties:

$^1$H-NMR spectrum (300 MHz, CDCl$_3$, TMS) δ: 0.80-0.90 (m, 12H), 1.00-1.60 (m, 19H), 1.61 and 1.69 (s, 3H, 4-CH$_3$), 1.96 (t, J=8.0 Hz, 2H), 2.28 (td, J=6.9 Hz, 2H), 2.49 (t, J=5.1 Hz, 3H, OH), 3.35-3.50 (m, 4H), 3.71 (d, J=5.1 Hz, 6H), 5.09 (t, J=6.9 Hz, 1H).

Example 57

Synthesis of mono-O-(4,8,12,16-tetramethylheptadec-3-enyl)diglycerol

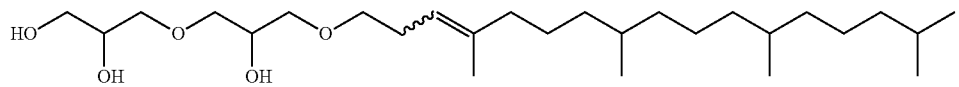 [SMILES: CC(=CCCOCC(O)COCC(O)CO)CCCC(C)CCCC(C)CCCC(C)C]

0.49 mL (3.5 mmol) of triethylamine, 0.68 g (3.54 mmol) of p-toluenesulfonyl chloride, 15 mg (0.16 mmol) of trimethylamine hydrochloride were added to a solution of 1.0 g (3.2 mmol) of 4,8,12,16-tetramethylheptadec-3-en-1-ol in dry methylene chloride (3.2 mL) at 0° C., sequentially. After being stirred for 2 hours at room temperature, 0.080 mL (0.64 mmol) of N,N-dimethyl-1,3-propanediamine was added to the reaction mixture at 0° C. After being stirred for 15 min, water was added, and the mixture was extracted with methylene chloride. The extract was washed with 1M hydrochloric acid, saturated sodium bicarbonate aqueous solution, and saturated brine, successively, and dried over anhydrous sodium sulfate. After filtration, the filtrate was concentrated to obtain (4,8,12,16-tetramethylheptadec-3-enyl)tosylate as a crude product.

0.21 g (55%, 4.8 mmol) of sodium hydride was added to a solution of 0.80 g (4.8 mmol) of diglycerol in dry N,N-dimethylformamide (5 mL) with cooling on ice. After the mixture was stirred for 30 min at 50° C., the above (4,8,12,16-tetramethylheptadec-3-enyl)tosylate was added dropwise with additional stirring for 12 hours at the same temperature. After addition of water at 0° C., the reaction mixture was extracted with ethyl acetate. The extract was washed with water, 1M hydrochloric acid, saturated sodium bicarbonate aqueous solution, and saturated brine, successively, and dried over anhydrous sodium sulfate. After filtration, the filtrate was concentrated, and the resulting residue was purified by silica gel column chromatography (methanol/methylene chloride mixture) to obtain 312 mg of the title compound (25% yield in 2 steps). The results of NMR analysis of the obtained compound are as shown below.

$^1$H-NMR spectrum (300 MHz, CDCl$_3$, TMS) δ: 0.80-0.90 (m, 12H), 1.00-1.60 (m, 19H), 1.61 and 1.69 (s, 3H, 4-CH$_3$), 1.90-2.05 (m, 2H), 2.25-2.35 (m, 2H), 3.40-4.00 (m, 12H), 5.10 (brs, 1H).

Example 58

Synthesis of mono-O-(4,8,12,16-tetramethylheptadec-3-enyl)triglycerol

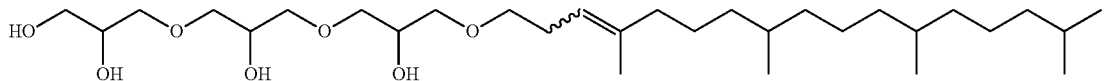 [SMILES: CC(=CCCOCC(O)COCC(O)COCC(O)CO)CCCC(C)CCCC(C)CCCC(C)C]

The title compound was synthesized using the same procedure as employed in Example 57, but with 1.16 g (4.83 mmol) of triglycerol instead of diglycerol. The compound was obtained (310 mg, 21% yield in 2 steps) having the following properties:

$^1$H-NMR spectrum (300 MHz, CDCl$_3$, TMS) a: 0.80-0.90 (m, 12H), 1.00-1.60 (m, 19H), 1.61 and 1.69 (s, 3H, 4-CH$_3$), 1.95 (m, 2H), 2.29 (m, 2H), 3.40-4.05 (m, 17H), 5.10 (brs, 1H).

Example 59

Synthesis of mono-O-(4,8,12,16-tetramethylheptadec-3-enyl)xylitol

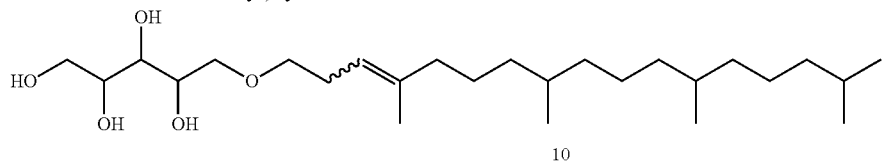

The title compound was synthesized using the same procedure as employed in Example 57, but with 0.73 g (4.8 mmol) of xylitol instead of diglycerol, having the following properties:

$^1$H-NMR spectrum (300 MHz, CDCl$_3$, TMS) δ: 0.80-0.90 (m, 12H), 1.00-1.70 (m, 22H), 1.94 (m, 2H), 2.20 (m, 2H), 3.00-3.80 (m, 9H), 5.01 (brs, 1H).

Example 60

Synthesis of mono-O-(4,8,12,16-tetramethylheptadec-3-enyl)mannitol

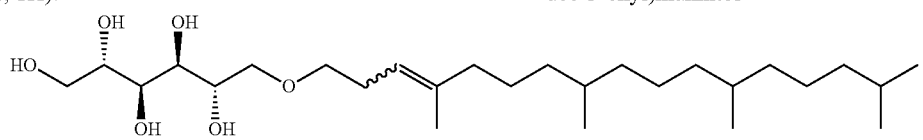

The title compound was synthesized using the same procedure as employed in Example 57, but with 0.88 g (4.8 mmol) of mannitol instead of diglycerol. The compound was obtained (97 mg, 8% yield in 2 steps) having the following properties:

$^1$H-NMR spectrum (300 MHz, CDCl$_3$, TMS) δ: 0.80-0.90 (m, 12H), 1.00-1.60 (m, 19H), 1.61 and 1.69 (s, 3H, 4-CH$_3$), 1.94 (m, 2H), 2.31 (m, 2H), 3.45-3.95 (m, 10H), 5.08 (brs, 1H).

Example 61

Synthesis of mono-O-(4,8,12,16-tetramethylheptadec-3-enyl)sorbitol

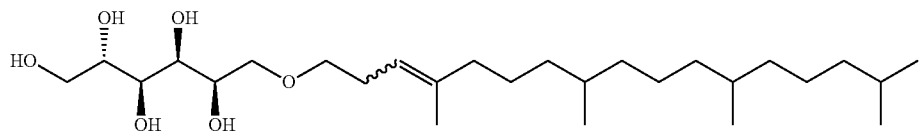 [SMILES: CC(=CCCOC[C@@H](O)[C@H](O)[C@@H](O)[C@@H](O)CO)CCCC(C)CCCC(C)CCCC(C)C]

The title compound was synthesized using the same procedure as employed in Example 57, but with 0.88 g (4.8 mmol) of sorbitol instead of diglycerol. The compound was obtained (126 mg, 10% yield in 2 steps) having the following properties:

$^1$H-NMR spectrum (300 MHz, CDCl$_3$, TMS) δ: 0.80-0.90 (m, 12H), 1.00-1.70 (m, 22H), 1.94 (m, 2H), 2.27 (m, 2H), 3.20-4.00 (m, 10H), 5.08 (brs, 1H).

Example 62

Synthesis of mono-O-(4,8,12,16-tetramethylheptadec-3-enyl)dipentaerythritol

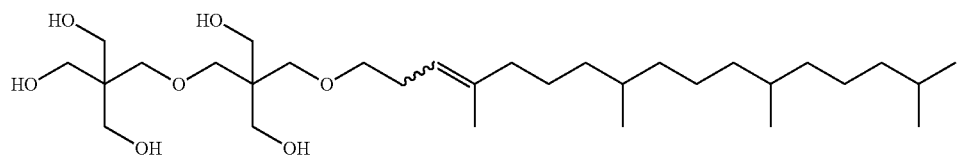 [SMILES: CC(=CCCOCC(CO)(CO)COCC(CO)(CO)CO)CCCC(C)CCCC(C)CCCC(C)C]

The title compound was synthesized using the same procedure as employed in Example 57, but with 1.23 g (4.83 mmol) of dipentaerythritol instead of diglycerol. The compound was obtained (133 mg, 6% yield in 2 steps) having the following properties:

$^1$H-NMR spectrum (300 MHz, CDCl$_3$, TMS) δ: 0.80-0.90 (m, 12H), 1.00-1.58 (m, 19H), 1.60 and 1.69 (s, 3H, 4-CH$_3$), 1.95 (t, J=7.7 Hz, 2H), 2.26 (td, J=6.3 Hz, 2H), 3.35-3.48 (m, 8H), 3.50-3.65 (m, 10H), 5.08 (t, J=6.3 Hz, 1H).

Example 63

Synthesis of mono-O-(4,8,12,16-tetramethylheptadec-3-enyl)ascorbic acid

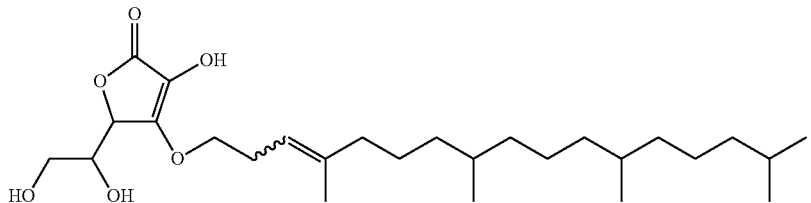 [SMILES: CC(=CCCOC1=C(O)C(=O)OC1C(O)CO)CCCC(C)CCCC(C)CCCC(C)C]

0.49 mL (3.5 mmol) of triethylamin, 0.68 g (3.54 mmol) of p-toluenesulfonyl chloride, 15 mg (0.16 mmol) of trimethylamine hydrochloride were added to a solution of 1.0 g (3.2 mmol) of 4,8,12,16-tetramethylheptadec-3-en-1-ol in dry methylene chloride (3.2 mL) at 0° C., sequentially. After being stirred for 2 hours at room temperature, 0.080 mL (0.64 mmol) of N,N-dimethyl-1,3-propanediamine was added to the reaction mixture at 0° C. After being stirred for 15 min, water was added, and the mixture was extracted with methylene chloride. The extract was washed with 1M hydrochloric acid, saturated sodium bicarbonate aqueous solution, and saturated brine, successively, and dried over anhydrous sodium sulfate. After filtration, the filtrate was concentrated to obtain (4,8,12,16-tetramethylheptadec-3-enyl)tosylate as a crude product.

0.49 mL (3.5 mmol) of triethylamine was added and dissolved in a suspension of 0.56 g (3.2 mmol) of ascorbic acid in acetonitrile (7 mL). After the above crude product of (4,8,12,16-tetramethylheptadec-3-enyl)tosylate was added at room temperature, the reaction mixture was heated for 2 hours at 90° C. The reaction mixture was concentrated, and the resulting residue was purified by silica gel column chromatography (methanol/methylene chloride mixture) to obtain the title compound.

Example 64

Synthesis of methyl 3,7,11,15-tetramethylhexadec-2-enoate

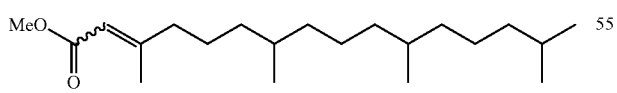

Under a nitrogen atmosphere, 17.4 mL (202 mmol) of oxalyl chloride was dissolved in methylene chloride (300 mL). 36 mL (0.51 mol) of dimethyl sulfoxide was slowly added dropwise to the mixture at −78° C. After the mixture was stirred for 15 min, 50 g (0.17 mol) of phytol was added, followed by stirring for 1 hour at the same temperature. After addition of 94 mL (0.68 mol) of triethylamine, the reaction mixture was allowed to warm up to room temperature. The mixture was concentrated with methylene chloride, and the residue was diluted with diethylether, and the solution was washed saturated brine, and dried over anhydrous sodium sulfate. After filtration, the filtrate was concentrated to obtain 3,7,11,15-tetramethylhexadec-2-en-1-al as a crude product.

The above obtained crude product of 3,7,11,15-tetramethylhexadec-2-en-1-al was dissolved in t-butanol (150 mL) and water (150 mL). 52.7 g (0.338 mmol) of sodium dihydrogen phosphate, 21 g (0.22 mmol) of amidosulfuric acid, and 19.6 g (0.216 mmol) of sodium chlorite were added to the solution. After being stirred for 18 hours at room temperature, the reaction mixture was diluted with ether. The solution was washed with water and saturated brine, successively, and dried over anhydrous sodium sulfate. After filtration, the filtrate was concentrated to obtain 3,7,11,15-tetramethylhexadec-2-enoic acid as a crude product.

The above obtained crude product of 3,7,11,15-tetramethylhexadec-2-enoic acid was dissolved in methanol (300 mL), and concentrated sulfuric acid (3 mL) was added and stirred for 18 hours at 55° C. Sodium bicarbonate was slowly added to the reaction solution and confirmed to be neutralized. After filtration, the filtrate was concentrated, and diluted with ethyl acetate. The solution was washed with water and saturated brine, successively, and dried over anhydrous sodium sulfate. After filtration, the filtrate was concentrated, and the resulting residue was purified by silica gel column chromatography (ethyl acetate/hexane mixture) to obtain 32.2 g of the title compound (59% in 3 steps) as a slightly yellow liquid. The results of NMR analysis of the obtained compound are as shown below.

$^1$H-NMR spectrum (300 MHz, CDCl$_3$, TMS) δ: 0.80-0.90 (m, 12H), 1.00-1.60 (m, 19H), 2.00-2.20 (m, 5H), 3.69 (s, 3H), 5.67 (s, 1H).

Example 65

Synthesis of mono-O-(3,7,11,15-tetramethylhexadec-2-enoyl)glycerol

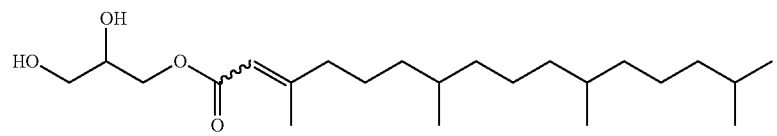 [SMILES: CC(=CC(=O)OCC(O)CO)CCCC(C)CCCC(C)CCCC(C)C]

1.0 g (3.1 mmol) of methyl 3,7,11,15-tetramethylhexadec-2-enoate was added dropwise to a solution of 0.57 g (6.2 mmol) of glycerol and 0.85 g (6.2 mmol) of potassium carbonate in dry N,N-dimethylformamide (3 mL) at 80° C. After the reaction mixture was stirred at 100° C. for 12 hours, 1M hydrochloric acid was added. The resulting solution was extracted with ether, and the extract was washed with saturated sodium bicarbonate aqueous solution and saturated brine, successively, and dried over anhydrous sodium sulfate. After filtration, the filtrate was concentrated, and the resulting residue was purified by silica gel column chromatography (ethyl acetate/hexane mixture) to obtain 459 mg of the title compound (35% yield) as a colorless viscous product.

The results of 1H-NMR analysis of the obtained compound are as shown below.

$^1$H-NMR spectrum (300 MHz, CDCl$_3$, TMS) δ: 0.80-0.95 (m, 12H), 1.00-1.80 (m, 19H), 1.90-2.20 (m, 5H), 3.50-4.00 (m, 3H), 4.10-4.30 (m, 2H), 5.71 (brs, 1H).

Example 66

Synthesis of mono-O-(3,7,11,15-tetramethylhexadec-2-enoyl)erythritol

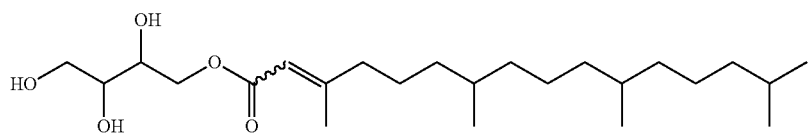 [SMILES: CC(=CC(=O)OCC(O)C(O)CO)CCCC(C)CCCC(C)CCCC(C)C]

The title compound was synthesized using the same procedure as employed in Example 65, but with 0.76 g (6.2 mmol) of erythritol instead of glycerol. The compound was obtained (378 mg, 27% yield) having the following properties:

$^1$H-NMR spectrum (300 MHz, CDCl$_3$, TMS) δ: 0.80-0.95 (m, 12H), 1.00-1.80 (m, 19H), 1.90-2.20 (m, 5H), 3.55-4.00 (m, 4H), 4.25-4.45 (m, 2H), 5.72 (brs, 1H).

Example 67

Synthesis of mono-O-(3,7,11,15-tetramethylhexadec-2-enoyl)pentaerythritol

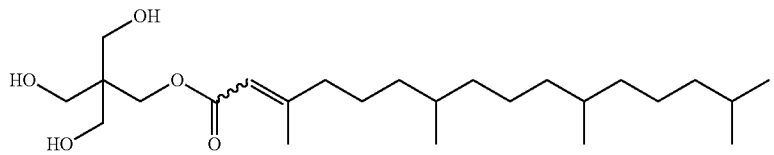 [SMILES: CC(=CC(=O)OCC(CO)(CO)CO)CCCC(C)CCCC(C)CCCC(C)C]

The title compound was synthesized using the same procedure as employed in Example 65, but with 0.84 g (6.2 mmol) of pentaerythritol instead of glycerol. The compound was obtained (537 mg, 37% yield) having the following properties:

$^1$H-NMR spectrum (300 MHz, CDCl$_3$, TMS) δ: 0.80-0.95 (m, 12H), 1.00-1.60 (m, 19H), 1.90-2.20 (m, 5H), 2.71 (brs, 30H), 3.65 (s, 6H), 4.25 (brs, 2H), 5.70 (brs, 1H).

Example 68

Synthesis of mono-O-(3,7,11,15-tetramethylhexadec-2-enoyl)diglycerol

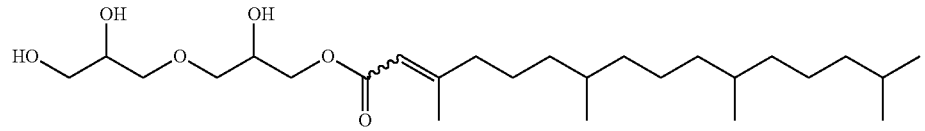 [SMILES: CC(=CC(=O)OCC(O)COCC(O)CO)CCCC(C)CCCC(C)CCCC(C)C]

The title compound was synthesized using the same procedure as employed in Example 65, but with 1.03 g (6.2 mmol) of diglycerol instead of glycerol. The compound was obtained (388 mg, 25% yield) having the following properties:

$^1$H-NMR spectrum (300 MHz, CDCl$_3$, TMS) δ: 0.80-0.90 (m, 12H), 1.00-1.80 (m, 19H), 1.91 and 2.16 (s, 3H, 3-CH$_3$), 2.10-2.20 (m, 2H), 3.50-3.95 (m, 7H), 4.00-4.30 (m, 3H), 5.71 (brs, 1H).

Example 69

Synthesis of mono-O-(3,7,11,15-tetramethylhexadec-2-enoyl)xylitol

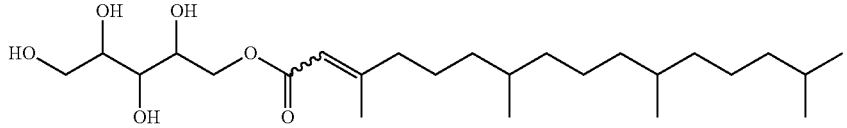 [SMILES: CC(=CC(=O)OCC(O)C(O)C(O)CO)CCCC(C)CCCC(C)CCCC(C)C]

The title compound was synthesized using the same procedure as employed in Example 65, but with 0.94 g (6.2 mmol) of xylitol instead of glycerol. The compound was obtained (219 mg, 15% yield) having the following properties:

$^1$H-NMR spectrum (300 MHz, CDCl$_3$, TMS) δ: 0.80-0.90 (m, 12H), 1.00-1.80 (m, 19H), 1.90 and 2.16 (s, 3H, 3-CH$_3$), 2.10-2.20 (m, 2H), 3.60-4.10 (m, 5H), 4.20-4.30 (m, 2H), 5.70 (brs, 1H).

Example 70

Synthesis of mono-O-(3,7,11,15-tetramethylhexadec-2-enoyl)triglycerol

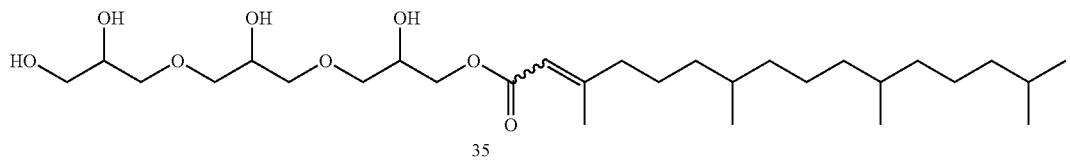

1.0 g (3.1 mmol) of methyl 3,7,11,15-tetramethylhexadec-2-enoate was added slowly dropwise to a solution of 1.49 g (6.2 mmol) of triglycerol and 0.85 g (6.2 mmol) of potassium carbonate in dry N,N-dimethylformamide (3 mL) at 100° C. After the reaction mixture was stirred at 100° C. for 15 hours, 1M hydrochloric acid was added. The reaction solution was extracted with ethyl acetate, and the extract was washed with saturated sodium bicarbonate aqueous solution and saturated brine, successively, and dried over anhydrous sodium sulfate. After filtration, the filtrate was concentrated, and the resulting residue was purified by silica gel column chromatography (methanol/methylene chloride mixture) to obtain 369 mg of the title compound (20% yield).

The results of 1H-NMR analysis of the obtained compound are as shown below.

$^1$H-NMR spectrum (300 MHz, CDCl$_3$, TMS) δ: 0.80-0.95 (m, 12H), 1.00-1.80 (m, 19H), 1.85-2.20 (m, 5H), 3.40-4.20 (m, 15H), 5.70 (brs, 1H).

Example 71

Synthesis of mono-O-(3,7,11,15-tetramethylhexadec-2-enoyl)mannitol

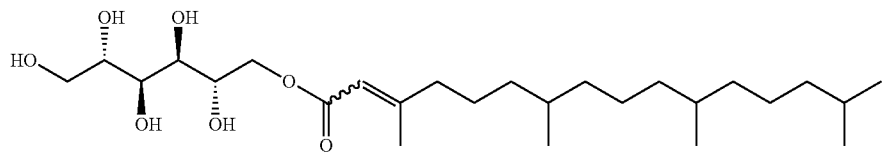 [SMILES: CC(=CC(=O)OC[C@H](O)[C@H](O)[C@@H](O)[C@@H](O)CO)CCCC(C)CCCC(C)CCCC(C)C]

The title compound was synthesized using the same procedure as employed in Example 70, but with 1.13 g (6.2 mmol) of mannitol instead of triglycerol. The compound was obtained (177 mg, 11% yield) having the following properties:

$^1$H-NMR spectrum (300 MHz, CDCl$_3$, TMS) δ: 0.80-0.90 (m, 12H), 1.00-1.90 (m, 22H), 2.10-2.20 (m, 2H), 3.70-4.25 (m, 8H), 5.72 (s, 1H).

Example 72

Synthesis of mono-O-(3,7,11,15-tetramethylhexadec-2-enoyl)sorbitol

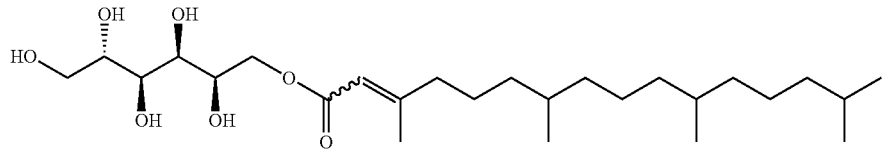 [SMILES: CC(=CC(=O)OC[C@@H](O)[C@H](O)[C@@H](O)[C@@H](O)CO)CCCC(C)CCCC(C)CCCC(C)C]

The title compound was synthesized using the same procedure as employed in Example 70, but with 1.13 g (6.2 mmol) of sorbitol instead of triglycerol. The compound was obtained (215 mg, 13% yield) having the following properties:

$^1$H-NMR spectrum (300 MHz, CDCl$_3$, TMS) δ: 0.80-0.90 (m, 12H), 1.00-1.80 (m, 19H), 1.80-2.30 (m, 5H), 3.60-4.50 (m, 8H), 5.70 (brs, 1H).

Example 73

Synthesis of mono-O-(3,7,11,15-tetramethylhexadec-2-enoyl)dipentaerythritol

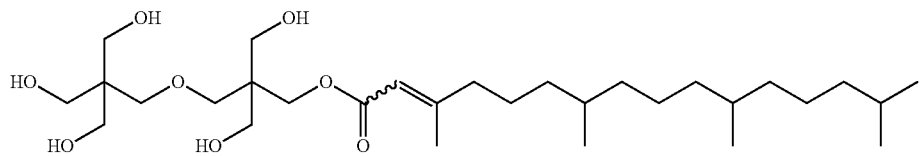 [SMILES: CC(=CC(=O)OCC(CO)(CO)COCC(CO)(CO)CO)CCCC(C)CCCC(C)CCCC(C)C]

The title compound was synthesized using the same procedure as employed in Example 70, but with 1.58 g (6.2 mmol) of dipentaerythritol instead of triglycerol. The compound was obtained (106 mg, 6% yield) having the following properties:

$^1$H-NMR spectrum (300 MHz, CDCl$_3$, TMS) δ: 0.80-0.90 (m, 12H), 1.00-1.80 (m, 19H), 1.91 and 2.16 (s, 3H, 3-CH$_3$), 2.10-2.20 (m, 2H), 3.30-3.80 (m, 14H), 4.15 (s, 2H), 5.68 (brs, 1H).

Example 74

Synthesis of mono-O-(3,7,11,15-tetramethylhexadec-2-enoyl)ascorbic acid

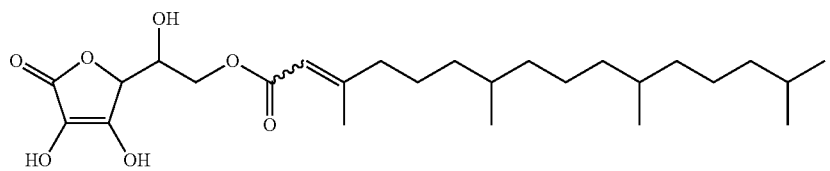 [SMILES: CC(=CC(=O)OCC(O)C1OC(=O)C(O)=C1O)CCCC(C)CCCC(C)CCCC(C)C]

0.55 g (3.1 mmol) of ascorbic acid was dissolved in concentrated sulfuric acid (14 mL). After addition of 1.0 g (3.1 mmol) of methyl 3,7,11,15-tetramethylhexadec-2-enoate, the mixture was stirred for 24 hours at room temperature. The reaction mixture was poured into iced water, and extracted with ethyl acetate. The extract was washed with water, 1M hydrochloric acid, saturated sodium bicarbonate aqueous solution, and saturated brine, successively, and dried over anhydrous sodium sulfate. After filtration, the filtrate was concentrated, and the resulting residue was purified by silica gel column chromatography (methanol/methylene chloride mixture) to obtain the title compound.

Example 75

Synthesis of 1-O-(3,7,11,15-tetramethylhexadec-2-enyl)-D-glucoside

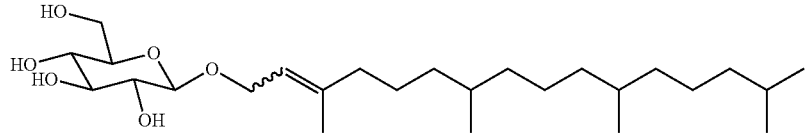 [SMILES: CC(=CCOC1OC(CO)C(O)C(O)C1O)CCCC(C)CCCC(C)CCCC(C)C]

3.4 g (8.7 mmol) of 13-D-Glucose pentaacetate and 2.0 g (6.7 mmol) of phytol were dissolved in dry acetonitrile (7 mL). 1.70 mL (13.4 mmol) of boron trifluoride diethyl etherate complex was added to the solution with cooling on ice. The reaction mixture was allowed to warm up slowly to room temperature while being stirred for 18 hours before addition of 2.8 mL (20 mmol) of triethylamine at 0° C. The resulting solution was diluted with ethyl acetate, and washed with water, 1M hydrochloric acid, saturated sodium bicarbonate aqueous solution, and saturated brine, successively, and dried over sodium sulfate. After filtration, the filtrate was concentrated to obtain a crude product of 1-O-(3,7,11,15-tetramethylhexadec-2-enyl)-D-glucopyranoside tetraacetate.

The above obtained crude product of 1-O-(3,7,11,15-tetramethylhexadec-2-enyl)-D-glucopyranoside tetraacetate was dissolved in methanol/tetrahydrofuran (1:1, 6 mL), and 0.67 mL (0.67 mmol) of 1M sodium methylate in methanol was added at room temperature. After being stirred for 24 hours, 48 μL (0.67 mmol) of acetyl chloride was added to the reaction mixture and the mixture was confirmed to be neutralized. After addition of water, the solution was extracted with ethyl acetate. The extract was washed with saturated brine, and dried over anhydrous sodium sulfate. After filtration, the filtrate was concentrated, and the resulting residue was purified by silica gel column chromatography (methanol/methylene chloride mixture) to obtain the title compound.

Example 76

Synthesis of 1-O-(3,7,11,15-tetramethylhexadec-2-enyl)-D-xylopyranoside

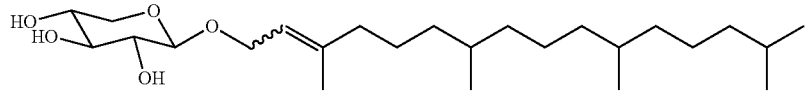 [SMILES: CC(=CCOC1OCC(O)C(O)C1O)CCCC(C)CCCC(C)CCCC(C)C]

The title compound was synthesized using the same procedure as employed in Example 75, but with 2.8 g (8.7 mmol) of D-xylose tetraacetate instead of 13-D-glucose pentaacetate.

Example 77

Synthesis of 1-O-(3,7,11,15-tetramethylhexadec-2-enyl)-D-galactoside

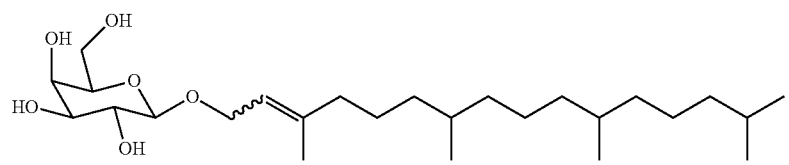 [SMILES: CC(=CCOC1OC(CO)C(O)C(O)C1O)CCCC(C)CCCC(C)CCCC(C)C]

The title compound was synthesized using the same procedure as employed in Example 75, but with 3.4 g (8.7 mmol) of D-galactose pentaacetate instead of β-D-glucose pentaacetate.

Example 78

Synthesis of 1-O-(3,7,11,15-tetramethylhexadec-2-enyl)-D-mannoside

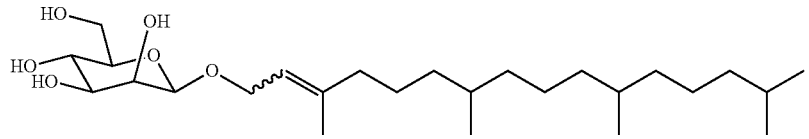 [SMILES: CC(=CCOC1OC(CO)C(O)C(O)C1O)CCCC(C)CCCC(C)CCCC(C)C]

The title compound was synthesized using the same procedure as employed in Example 75, but with 3.4 g (8.7 mmol) of D-mannose pentaacetate instead of β-D-glucose pentaacetate.

Example 79

Synthesis of 1-O-(3,7,11,15-tetramethylhexadec-2-enyl)-D-maltoside

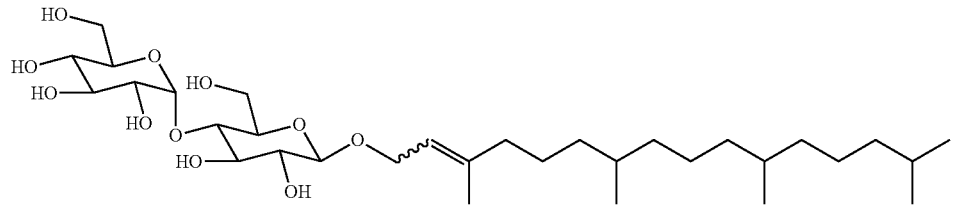 [SMILES: CC(=CCOC1OC(CO)C(OC2OC(CO)C(O)C(O)C2O)C(O)C1O)CCCC(C)CCCC(C)CCCC(C)C]

5.9 g (8.7 mmol) of D-Maltose octaacetate and 2.0 g (6.7 mmol) of phytol were dissolved in dry acetonitrile (7 mL). 1.70 mL (13.4 mmol) of boron trifluoride diethyl etherate complex was added with cooling on ice. The reaction mixture was allowed to warm up slowly to room temperature while being stirred for 18 hours before addition of 2.8 mL (20 mmol) of triethylamine at 0° C. The resulting solution was diluted with ethyl acetate, and washed with water, 1M hydrochloric acid, saturated sodium bicarbonate aqueous solution, and saturated brine, successively, and dried over sodium sulfate. After filtration, the filtrate was concentrated to obtain 1-O-(3,7,11,15-tetramethylhexadec-2-enyl)-D-maltoside heptaacetate as a crude product.

The above obtained crude product of 1-O-(3,7,11,15-tetramethylhexadec-2-enyl)-D-maltoside heptaacetate was dissolved in methanol/tetrahydrofuran (1:1, 6 mL), and 0.67 mL (0.67 mmol) of 1M sodium methylate in methanol was added at room temperature, and stirred for 24 hours. 48 μL (0.67 mmol) of acetyl chloride was added to the reaction mixture and the mixture was confirmed to be neutralized. The resulting mixture was concentrated, and the resulting residue was purified by silica gel column chromatography (methanol/methylene chloride mixture) to obtain the title compound.

Example 80

Synthesis of mono-O-(3,7,11,15-tetramethylhexadec-2-enyl)glycerol

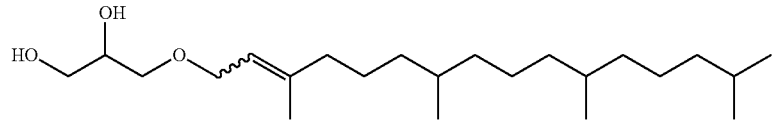 [SMILES: CC(=CCOCC(O)CO)CCCC(C)CCCC(C)CCCC(C)C]

0.90 g (6.7 mmol) of N-Chlorosuccinimide was suspended in methylene chloride (8 mL). After addition of 0.52 mL (7.1 mmol) of dimethylsulfide at 0° C., the solution was stirred for 20 min. After addition of 1.0 g (3.4 mmol) of phytol, the mixture was stirred for 1 hour at 0° C., with additional stirring for 6 hours at room temperature. After addition of sodium bicarbonate aqueous solution, the reaction mixture was extracted with methylene chloride. The extract was washed with saturated brine, and dried over anhydrous sodium sulfate. After filtration, the filtrate was concentrated to obtain 3,7,11,15-tetramethylhexadec-2-ene-1-chloride as a crude product.

0.20 g (60%, 5.1 mmol) of sodium hydride was added to a solution of 0.47 g (5.1 mmol) of glycerol in dry N,N-dimethylformamide/tetrahydrofuran (1:1, 4 mL) will coiling on ice. After the mixture was stirred for 30 min at 50° C., the above 3,7,11,15-tetramethylhexadec-2-ene-1-chloride was added dropwise with additional stirring for 20 hours at the same temperature. After addition of water at 0° C., the reaction mixture was extracted with ether. The extract was washed with water, 1M hydrochloric acid, saturated sodium bicarbonate aqueous solution, and saturated brine, successively, and dried over anhydrous sodium sulfate. After filtration, the filtrate was concentrated, and the resulting residue was purified by silica gel column chromatography (ethyl acetate/hexane mixture) to obtain the title compound. The results of NMR analysis of the obtained compound are as shown below.

$^1$H-NMR spectrum (300 MHz, CDCl$_3$, TMS) δ: 0.80-0.90 (m, 12H), 1.00-1.80 (m, 22H), 2.00 (t, J=8.2 Hz, 2H), 2.16 (brs, 1H, OH), 2.61 (brs, 1H, OH), 3.45-3.80 (m, 4H), 3.82-4.05 (m, 3H), 5.33 (t, J=6.2 Hz, 1H).

Example 81

Synthesis of mono-O-(3,7,11,15-tetramethylhexadec-2-enyl)erythritol

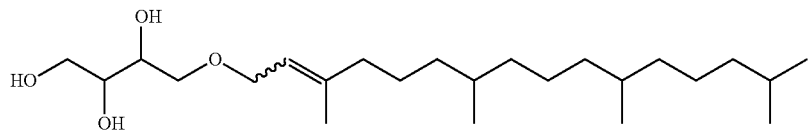 [SMILES: CC(=CCOCC(O)C(O)CO)CCCC(C)CCCC(C)CCCC(C)C]

The title compound was synthesized using the same procedure as employed in Example 80, but with 0.62 g (5.1 mmol) of erythritol instead of glycerol. The compound was obtained having the following properties:

$^1$H-NMR spectrum (300 MHz, CDCl$_3$, TMS) δ: 0.80-0.90 (m, 12H), 1.00-1.80 (m, 22H), 2.00 (t, J=8.6 Hz, 2H), 2.34 (brs, 1H, OH), 2.68 (brd, 1H, OH), 2.78 (brd, 1H, OH), 3.50-3.90 (m, 6H), 4.00-4.20 (m, 2H), 5.32 (brs, 1H).

Example 82

Synthesis of mono-O-(3,7,11,15-tetramethylhexadec-2-enyl)pentaerythritol

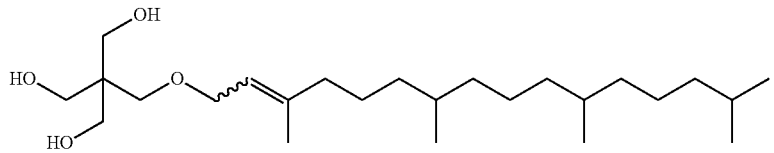 [SMILES: CC(=CCOCC(CO)(CO)CO)CCCC(C)CCCC(C)CCCC(C)C]

The title compound was synthesized using the same procedure as employed in Example 80, but with 0.69 g (5.1 mmol) of pentaerythritol instead of glycerol. The compound was obtained having the following properties:

$^1$H-NMR spectrum (300 MHz, CDCl$_3$, TMS) δ: 0.80-0.90 (m, 12H), 1.00-1.75 (m, 22H), 1.90-2.05 (m, 2H), 2.60 (brs, 3H, OH), 3.46 (s, 2H), 3.72 (s, 6H), 3.98 (d, J=6.7 Hz, 2H), 5.29 (t, J=6.7 Hz, 1H).

Example 83

Synthesis of mono-O-(3,7,11,15-tetramethylhexadec-2-enyl)diglycerol

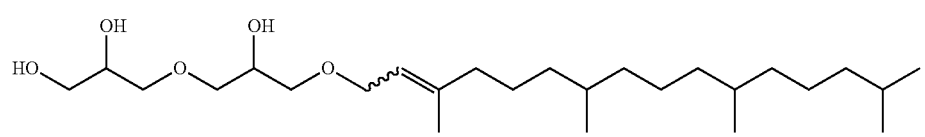 [SMILES: CC(=CCOCC(O)COCC(O)CO)CCCC(C)CCCC(C)CCCC(C)C]

The title compound was synthesized using the same procedure as employed in Example 80, but with 0.85 g (5.1 mmol) of diglycerol instead of glycerol.

Example 84

Synthesis of mono-O-(3,7,11,15-tetramethylhexadec-2-enyl)triglycerol

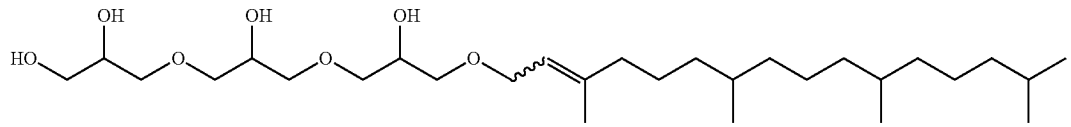 [SMILES: CC(=CCOCC(O)COCC(O)COCC(O)CO)CCCC(C)CCCC(C)CCCC(C)C]

0.90 g (6.7 mmol) of N-Chlorosuccinimide was suspended in methylene chloride (8 mL). After addition of 0.52 mL (7.1 mmol) of dimethylsulfide at 0° C., the solution was stirred for 20 min. After addition of 1.0 g (3.4 mmol) of phytol, the mixture was stirred for 1 hour at 0° C., with additional stirring for 6 hours at room temperature. After addition of saturated sodium bicarbonate aqueous solution, the reaction mixture was extracted with methylene chloride. The extract was washed with saturated brine, and dried over anhydrous sodium sulfate. After filtration, the filtrate was concentrated to obtain 3,7,11,15-tetramethylhexadec-2-ene-1-chloride as a crude product.

0.20 g (60%, 5.1 mmol) of sodium hydride was added to a solution of 0.47 g (5.1 mmol) of triglycerol in dry N,N-dimethylformamide/tetrahydrofuran (1:1, 4 mL) will cooling on ice. After the mixture was stirred for 30 min at 50° C., the above 3,7,11,15-tetramethylhexadec-2-ene-1-chloride was added dropwise, with additional stirring for 20 hours at the same temperature. After addition of water at 0° C., the reaction mixture was extracted with ethyl acetate. The extract was washed with water, 1M hydrochloric acid, saturated sodium bicarbonate aqueous solution, and saturated brine, successively, and dried over anhydrous sodium sulfate. After filtration, the filtrate was concentrated, and the resulting residue was purified by silica gel column chromatography (methanol/methylene chloride mixture) to obtain the title compound.

Example 85

Synthesis of mono-O-(3,7,11,15-tetramethylhexadec-2-enyl)xylitol

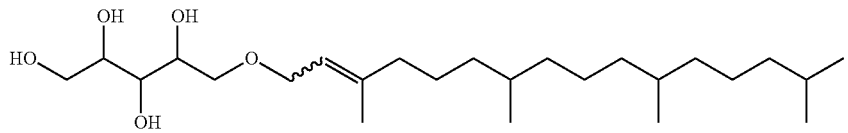 [SMILES: CC(=CCOCC(O)C(O)C(O)CO)CCCC(C)CCCC(C)CCCC(C)C]

The title compound was synthesized using the same procedure as employed in Example 84, but with 0.78 g (5.1 mmol) of xylitol instead of triglycerol. The compound was obtained having the following properties:

$^1$H-NMR spectrum (300 MHz, CDCl$_3$, TMS) δ: 0.80-0.90 (m, 12H), 1.00-1.70 (m, 22H), 2.00 (t, J=7.7 Hz, 2H), 3.50-4.25 (m, 9H), 5.32 (brs, 1H).

Example 86

Synthesis of mono-O-(3,7,11,15-tetramethylhexadec-2-enyl)mannitol

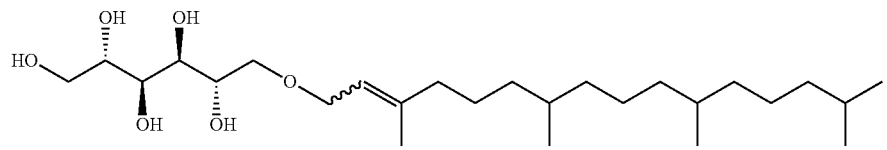 [SMILES: CC(=CCOC[C@H](O)[C@H](O)[C@@H](O)[C@@H](O)CO)CCCC(C)CCCC(C)CCCC(C)C]

The title compound was synthesized using the same procedure as employed in Example 84, but with 0.93 g (5.1 mmol) of mannitol instead of triglycerol.

Example 87

Synthesis of mono-O-(3,7,11,15-tetramethylhexadec-2-enyl)sorbitol

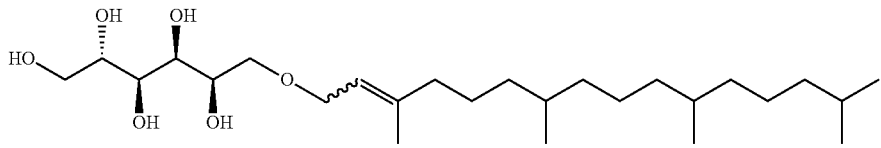 [SMILES: CC(=CCOC[C@@H](O)[C@H](O)[C@@H](O)[C@@H](O)CO)CCCC(C)CCCC(C)CCCC(C)C]

The title compound was synthesized using the same procedure as employed in Example 84, but with 0.93 g (5.1 mmol) of sorbitol instead of triglycerol.

Example 88

Synthesis of mono-O-(3,7,11,15-tetramethylhexadec-2-enyl)dipentaerythritol

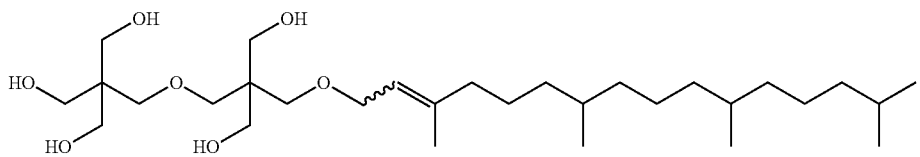 [SMILES: CC(=CCOCC(CO)(CO)COCC(CO)(CO)CO)CCCC(C)CCCC(C)CCCC(C)C]

The title compound was synthesized using the same procedure as employed in Example 84, but with 1.3 g (5.1 mmol) of dipentaerythritol instead of triglycerol.

Example 89

Synthesis of mono-O-(3,7,11,15-tetramethylhexadec-2-enyl)ascorbic acid

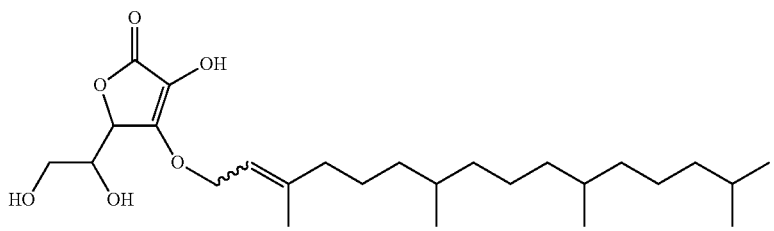 [SMILES: CC(=CCOC1=C(O)C(=O)OC1C(O)CO)CCCC(C)CCCC(C)CCCC(C)C]

0.90 g (6.7 mmol) of N-Chlorosuccinimide was suspended in methylene chloride (8 mL). After addition of 0.52 mL (7.1 mmol) of dimethylsulfide at 0° C., the solution was stirred for 20 min. After addition of 1.0 g (3.4 mmol) of phytol, the mixture was stirred for 1 hour at 0° C., with additional stirring for 6 hours at room temperature. After addition of saturated sodium bicarbonate aqueous solution, the reaction mixture was extracted with methylene chloride. The extract was washed with saturated brine, and dried over anhydrous sodium sulfate. After filtration, the filtrate was concentrated to obtain 3,7,11,15-tetramethylhexadec-2-ene-1-chloride as a crude product.

0.52 mL (3.7 mmol) of triethylamine was added and dissolved in a suspension of 0.60 g (3.4 mmol) of ascorbic acid in acetonitrile (7 mL). After the above crude product of 3,7,11,15-tetramethylhexadec-2-ene-1-chloride was added at room temperature, the reaction mixture was heated for 2 hours at 90° C. The reaction solution was concentrated, and the resulting residue was purified by silica gel column chromatography (methanol/methylene chloride mixture) to obtain the title compound.

Example 90

Synthesis of methyl 5,9,13-trimethyltetradec-4-enoate

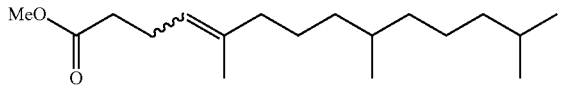 [SMILES: COC(=O)CCC=C(C)CCCC(C)CCCC(C)C]

A mixture of 0.29 mL (3.9 mmol) of propionic acid and trimethyl orthoacetate 1.0 mL (7.8 mmol) was slowly added dropwise to a solution of 8.7 g (39 mmol) of tetrahydronerolidol and 11 mL (86 mmol) of trimethyl orthoacetate at 140° C. After the reaction mixture was stirred for 18 hours at the same temperature, a mixture of 0.10 mL (1.3 mmol) of propionic acid and 0.3 mL (2.3 mmol) of trimethyl orthoacetate was added with additional stirring for 2 hours. The reaction mixture was subjected to simple distillation (external temperature 140° C., vacuum degree: 15 kPa) to release components with low boiling point, and the resulting residue was purified by silica gel column chromatography (ethyl acetate/hexane mixture) to obtain 7.0 g of the title compound (65% yield) as a colorless transparent liquid. The results of NMR analysis of the obtained compound are as shown below.

$^{1}$H-NMR spectrum (300 MHz, CDCl$_3$, TMS) δ: 0.80-0.90 (m, 9H), 1.00-1.70 (m, 15H), 1.96 (td, J=7.1, 18.2 Hz, 2H), 2.25-2.35 (m, 4H), 3.67 (s, 3H), 5.08 (brs, 1H).

Example 91

Synthesis of 5,9,13-trimethyltetradec-4-en-1-ol

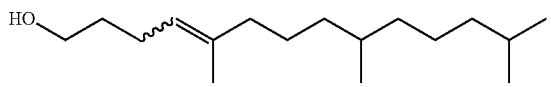 [SMILES: CC(=CCCCO)CCCC(C)CCCC(C)C]

Under a nitrogen atmosphere, 16.8 g (443 mmol) of lithium aluminum hydride was added little by little at 0° C. to a solution of 50.0 g (177 mmol) of methyl 5,9,13-trimethyltetradec-4-enoate in dry tetrahydrofuran (440 mL). After being stirred at 50° C. for 4 hours, the reaction mixture was cooled on ice, followed by careful addition of saturated sodium sulfate aqueous solution until the resulting gray suspension turned white. Sodium sulfate was added to the solution at room temperature for drying. After filtration, the filtrate was concentrated to obtain 45 g of the title compound (100% yield) as a slightly yellow transparent liquid. The results of NMR analysis of the obtained compound are as shown below.

$^{1}$H-NMR spectrum (400 MHz, CDCl$_3$, TMS) δ: 0.80-0.90 (m, 9H), 1.00-1.70 (m, 17H), 1.90-2.20 (m, 4H), 3.60-3.70 (m, 2H), 5.14 (t, J=7.1 Hz, 1H).

Example 92

Synthesis of mono-O-(5,9,13-trimethyltetradec-4-enoyl)glycerol

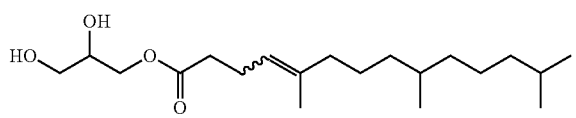 [SMILES: CC(=CCCC(=O)OCC(O)CO)CCCC(C)CCCC(C)C]

1.0 g (3.5 mmol) of methyl 5,9,13-trimethyltetradec-4-enoate was slowly added dropwise to a solution of 0.65 g (7.1 mmol) of glycerol and 0.59 g (4.3 mmol) of potassium carbonate in dry N,N-dimethylformamide (3.5 mL) at 80° C. After the reaction mixture was stirred at 100° C. for 18 hours, 1M hydrochloric acid was added. The resulting solution was extracted with ether, and the extract was washed with saturated sodium bicarbonate aqueous solution and saturated brine, successively, and dried over anhydrous sodium sulfate. After filtration, the filtrate was concentrated, and the resulting residue was purified by silica gel column chromatography (ethyl acetate/hexane mixture) to obtain the title compound.

The results of 1H-NMR analysis of the obtained compound are as shown below.

$^{1}$H-NMR spectrum (300 MHz, CDCl$_3$, TMS) δ: 0.80-0.90 (m, 9H), 1.00-1.70 (m, 15H), 1.97 (td, J=7.8, 17.0 Hz, 2H), 2.13 (t, J=6.1 Hz, 1H, OH), 2.25-2.45 (m, 4H), 2.55 (d, J=5.2 Hz, 1H, OH), 3.50-4.00 (m, 3H), 4.10-4.25 (m, 2H), 5.08 (t, J=6.7 Hz, 1H).

Example 93

Synthesis of mono-O-(5,9,13-trimethyltetradec-4-enoyl)erythritol

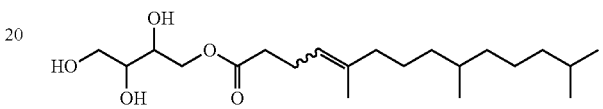

1.0 g (3.5 mmol) of methyl 5,9,13-trimethyltetradec-4-enoate was slowly added dropwise to a solution of erythritol 0.86 g (7.1 mmol) and 0.59 g (4.3 mmol) of potassium carbonate in dry N,N-dimethylformamide (3.5 mL) at 80° C. After the reaction mixture was stirred at 100° C. for 18 hours, 1M hydrochloric acid was added. The resulting solution was extracted with ether, and the extract was washed with saturated sodium bicarbonate aqueous solution and saturated brine, successively, and dried over anhydrous sodium sulfate. After filtration, the filtrate was concentrated, and the resulting residue was purified by silica gel column chromatography (ethyl acetate/hexane mixture) to obtain 275 mg of the title compound (21% yield).

The results of 1H-NMR analysis of the obtained compound are as shown below.

$^{1}$H-NMR spectrum (300 MHz, CDCl$_3$, TMS) δ: 0.80-0.95 (m, 9H), 1.00-1.60 (m, 12H), 1.61 and 1.68 (s, 3H, 5-CH$_3$), 1.97 (m, 2H), 2.18 (brs, 1H, OH), 2.30-2.45 (m, 4H), 2.69 (brs, 1H, OH), 2.84 (brs, 1H, OH), 3.63 (m, 1H), 3.80-3.95 (m, 3H), 4.25-4.40 (m, 2H), 5.08 (t, J=6.6 Hz, 1H).

Example 94

Synthesis of mono-O-(5,9,13-trimethyltetradec-4-enoyl)pentaerythritol

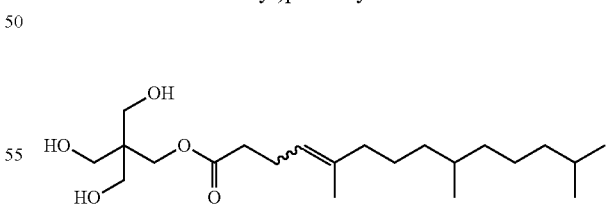

The title compound was synthesized using the same procedure as employed in Example 92, but with 0.96 g (7.1 mmol) of pentaerythritol instead of erythritol. The compound was obtained (469 mg, 35% yield) having the following properties:

$^{1}$H-NMR spectrum (300 MHz, CDCl$_3$, TMS) δ: 0.80-0.95 (m, 9H), 1.00-1.60 (m, 12H), 1.61 and 1.67 (s, 3H, 5-CH$_3$), 1.97 (m, 2H), 2.30-2.45 (m, 4H), 2.54 (brs, 31-1, OH), 3.64 (s, 6H), 4.23 (s, 2H), 5.07 (t, J=6.8 Hz, 1H).

Example 95

Synthesis of mono-O-(5,9,13-trimethyltetradec-4-enoyl)diglycerol

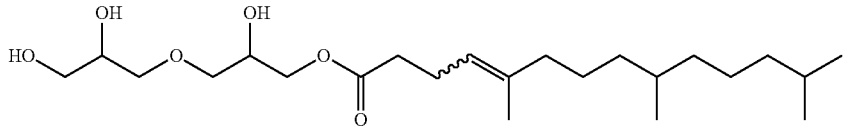 [SMILES: CC(=CCCC(=O)OCC(O)COCC(O)CO)CCCC(C)CCCC(C)C]

1.0 g (3.5 mmol) of methyl 5,9,13-trimethyltetradec-4-enoate was slowly added dropwise to a solution of 1.18 g (7.1 mmol) of diglycerol and 0.59 g (4.3 mmol) of potassium carbonate in dry N,N-dimethylformamide (3.5 mL) at 80° C. After the reaction mixture was stirred at 100° C. for 18 hours, 1M hydrochloric acid was added. The resulting solution was extracted with ethyl acetate, and the extract was washed with saturated sodium bicarbonate aqueous solution and saturated brine, successively, and dried over anhydrous sodium sulfate. After filtration, the filtrate was concentrated, and the resulting residue was purified by silica gel column chromatography (methanol/methylene chloride mixture) to obtain 249 mg of the title compound (17% yield).

The results of 1H-NMR analysis of the obtained compound are as shown below.

$^1$H-NMR spectrum (300 MHz, CDCl$_3$, TMS) δ: 0.80-0.95 (m, 9H), 1.00-1.60 (m, 12H), 1.61 and 1.68 (s, 3H, 5-CH$_3$), 1.97 (m, 2H), 2.25-2.43 (m, 4H), 3.50-4.20 (m, 10H), 5.08 (t, J=6.8 Hz, 1H).

Example 96

Synthesis of mono-O-(5,9,13-trimethyltetradec-4-enoyl)triglycerol

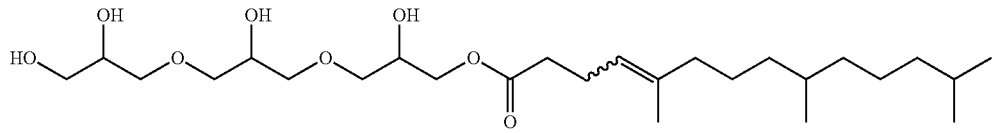 [SMILES: CC(=CCCC(=O)OCC(O)COCC(O)COCC(O)CO)CCCC(C)CCCC(C)C]

The title compound was synthesized using the same procedure as employed in Example 95, but with 1.7 g (7.1 mmol) of triglycerol instead of diglycerol, having the following properties:

$^1$H-NMR spectrum (300 MHz, CDCl$_3$, TMS) δ: 0.80-0.95 (m, 9H), 1.00-1.58 (m, 12H), 1.60 and 1.67 (s, 3H, 5-CH$_3$), 1.96 (m, 2H), 2.25-2.40 (m, 4H), 3.50-3.80 (m, 11H), 3.89 (m, 1H), 4.00 (m, 1H), 4.10-4.20 (m, 2H), 5.08 (t, J=6.6 Hz, 1H).

Example 97

Synthesis of mono-O-(5,9,13-trimethyltetradec-4-enoyl)xylitol

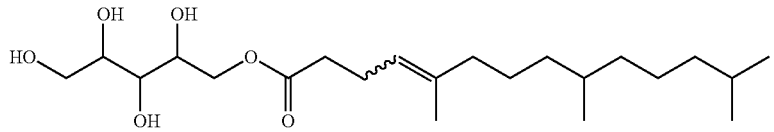 [SMILES: CC(=CCCC(=O)OCC(O)C(O)C(O)CO)CCCC(C)CCCC(C)C]

The title compound was synthesized using the same procedure as employed in Example 95, but with 1.08 g (7.08 mmol) of xylitol instead of diglycerol. The compound was obtained (306 mg, 22% yield) having the following properties:

$^1$H-NMR spectrum (300 MHz, CDCl$_3$, TMS) δ: 0.80-0.95 (m, 9H), 1.00-1.60 (m, 12H), 1.61 and 1.68 (s, 3H, 5-CH$_3$), 1.97 (m, 2H), 2.25-2.45 (m, 4H), 3.66 (brs, 1H), 3.75-3.90 (m, 3H), 4.02 (m, 1H), 4.24 (d, J=5.8 Hz, 2H), 5.08 (t, J=6.4 Hz, 1H).

Example 98

Synthesis of mono-O-(5,9,13-trimethyltetradec-4-enoyl)mannitol

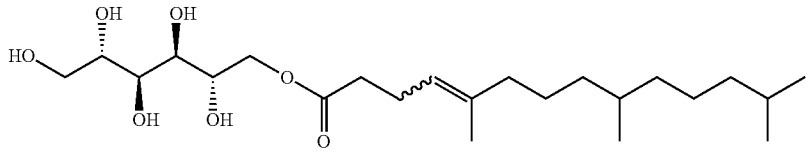 [SMILES: CC(=CCCC(=O)OC[C@H](O)[C@H](O)[C@@H](O)[C@@H](O)CO)CCCC(C)CCCC(C)C]

The title compound was synthesized using the same procedure as employed in Example 95, but with 1.29 g (7.08 mmol) of mannitol instead of diglycerol. The compound was obtained (367 mg, 24% yield) having the following properties:

$^1$H-NMR spectrum (300 MHz, CDCl$_3$+3% CD$_3$OD, TMS) δ: 0.80-0.95 (m, 9H), 1.00-1.58 (m, 12H), 1.60 and 1.67 (s, 3H, 5-CH$_3$), 1.96 (m, 2H), 2.25-2.45 (m, 4H), 3.65-3.95 (m, 6H), 4.24 (dd, J=6.2, 11.5 Hz, 1H), 4.39 (dd, 11.5 Hz, 1H), 5.08 (brs, 1H).

Example 99

Synthesis of mono-O-(5,9,13-trimethyltetradec-4-enoyl)sorbitol

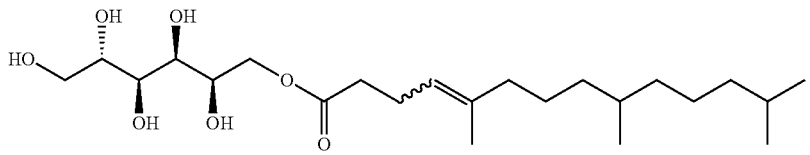 [SMILES: CC(=CCCC(=O)OC[C@@H](O)[C@H](O)[C@@H](O)[C@@H](O)CO)CCCC(C)CCCC(C)C]

The title compound was synthesized using the same procedure as employed in Example 95, but with 1.29 g (7.08 mmol) of sorbitol instead of diglycerol. The compound was obtained (439 mg, 29% yield) having the following properties:

$^1$H-NMR spectrum (300 MHz, CDCl$_3$, TMS) δ: 0.80-0.95 (m, 9H), 1.00-1.58 (m, 12H), 1.59 and 1.66 (s, 3H, 5-CH$_3$), 1.96 (m, 2H), 2.20-2.45 (m, 4H), 3.55-4.60 (m, 8H), 5.07 (brs, 1H).

Example 100

Synthesis of mono-O-(5,9,13-trimethyltetradec-4-enoyl)dipentaerythritol

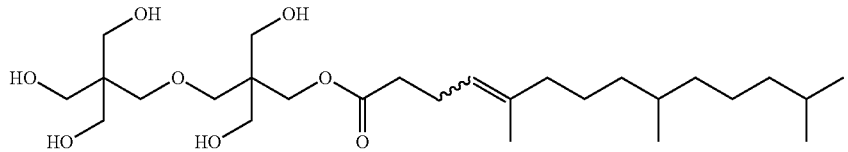 [SMILES: CC(=CCCC(=O)OCC(CO)(CO)COCC(CO)(CO)CO)CCCC(C)CCCC(C)C]

The title compound was synthesized using the same procedure as employed in Example 95, but with 1.80 g (7.08 mmol) of dipentaerythritol instead of diglycerol. The compound was obtained (224 mg, 13% yield) having the following properties:

$^1$H-NMR spectrum (300 MHz, CDCl$_3$+3% CD$_3$OD, TMS) δ: 0.80-0.90 (m, 9H), 1.00-1.60 (m, 12H), 1.61 and 1.68 (s, 3H, 5-CH$_3$), 1.99 (m, 2H), 2.25-2.45 (m, 4H), 3.35-3.60 (m, 14H), 4.07 (s, 2H), 5.07 (t, J=6.8 Hz, 1H).

Example 101

Synthesis of mono-O-(5,9,13-trimethyltetradec-4-enoyl)ascorbic acid

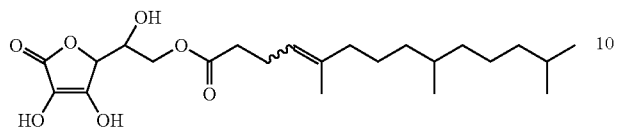

0.62 g (3.5 mmol) of ascorbic acid was dissolved in concentrated sulfuric acid (16 mL). After addition of 1.0 g (3.5 mmol) of methyl 5,9,13-trimethyltetradec-4-enoate, the mixture was stirred for 24 hours at room temperature. The reaction mixture was poured into iced water, and extracted with ethyl acetate. The extract was washed with water, 1M hydrochloric acid, saturated sodium bicarbonate aqueous solution, and saturated brine, successively, and dried over anhydrous sodium sulfate. After filtration, the filtrate was concentrated, and the resulting residue was purified by silica gel column chromatography (methanol/methylene chloride mixture) to obtain the title compound.

Example 102

Synthesis of 1-O-(5,9,13-trimethyltetradec-4-enyl)-D-glucoside

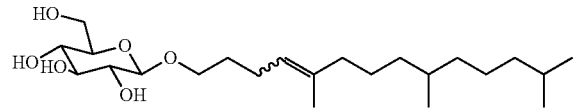 [SMILES: CC(=CCCCOC1OC(CO)C(O)C(O)C1O)CCCC(C)CCCC(C)C]

4.0 g (10 mmol) of β-D-glucose pentaacetate and 2.0 g (7.9 mmol) of 5,9,13-trimethyltetradec-4-en-1-ol were dissolved in dry acetonitrile (8 mL). 2.0 mL (16 mmol) of boron trifluoride diethyl etherate complex was added to the solution with cooling on ice. The reaction mixture was allowed to warm up slowly to room temperature while being stirred for 24 hours before addition of 3.3 mL (24 mmol) of triethylamine at 0° C. The resulting solution was diluted with ethyl acetate, and washed with water, 1M hydrochloric acid, saturated sodium bicarbonate aqueous solution, and saturated brine, successively, and dried over sodium sulfate. After filtration, the filtrate was concentrated to obtain 1-O-(5,9,13-trimethyltetradec-4-enyl)-D-glucopyranoside tetraacetate as a crude product.

The above obtained crude product of 1-O-(5,9,13-trimethyltetradec-4-enyl)-D-glucopyranoside tetraacetate was dissolved in methanol/tetrahydrofuran (1:1, 8 mL), and 0.79 mL (0.79 mmol) of 1M sodium methylate in methanol was added at room temperature. After being stirred for 24 hours, 62 μL (0.86 mmol) of acetyl chloride was added to the reaction mixture and the mixture was confirmed to be weakly acidic. After addition of water, the solution was extracted with ethyl acetate. The extract was washed with saturated brine, and dried over anhydrous sodium sulfate. After filtration, the filtrate was concentrated, and the resulting residue was purified by silica gel column chromatography (methanol/methylene chloride mixture) to obtain 284 mg of the title compound (9% yield in 2 steps). The results of NMR analysis of the obtained compound are as shown below.

$^1$H-NMR spectrum (300 MHz, CDCl$_3$, TMS) δ: 0.80-0.90 (m, 9H), 1.00-1.80 (m, 17H), 1.90-2.15 (m, 4H), 3.30 (d, J=8.8 Hz, 1H), 3.39 (t, J=8.0 Hz, 1H), 3.45-3.70 (m, 3H), 3.80-3.93 (m, 3H), 4.30 (d, J=7.6 Hz, 1H), 5.09 (brs, 1H).

Example 103

Synthesis of 1-O-(5,9,13-trimethyltetradec-4-enyl)-D-xylopyranoside

The title compound was synthesized using the same procedure as employed in Example 102, but with 3.25 g (10.2 mmol) of D-xylose tetraacetate instead of β-D-glucose pentaacetate. The compound was obtained (420 mg, 13% yield in 2 steps) having the following properties:

$^1$H-NMR spectrum (300 MHz, CDCl$_3$, TMS) δ: 0.80-0.90 (m, 9H), 1.00-1.75 (m, 17H), 1.90-2.10 (m, 4H), 3.30-4.07 (m, 7H), 4.38 (d, J=6.0 Hz, 0.6H), 4.80 (d, J=3.7 Hz, 0.4H), 5.11 (brs, 1H).

Example 104

Synthesis of 1-O-(5,9,13-trimethyltetradec-4-enyl)-D-galactoside

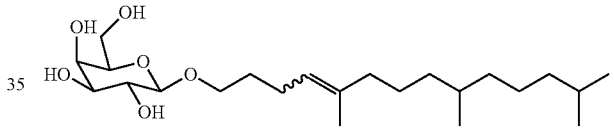

The title compound was synthesized using the same procedure as employed in Example 102, but with 4.0 g (10 mmol) of D-galactose pentaacetate instead of β-D-glucose pentaacetate. The compound was obtained (383 mg, 12% yield in 2 steps) having the following properties:

$^1$H-NMR spectrum (300 MHz, CDCl$_3$, TMS) δ: 0.80-0.90 (m, 9H), 1.00-1.70 (m, 17H), 1.90-2.05 (m, 4H), 3.40-4.12 (m, 8H), 4.24 (d, J=6.7 Hz, 1H), 5.10 (brs, 1H).

Example 105

Synthesis of 1-O-(5,9,13-trimethyltetradec-4-enyl)-D-mannoside

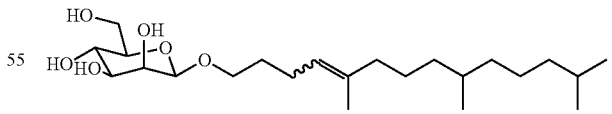

The title compound was synthesized using the same procedure as employed in Example 102, but with 4.0 g (10 mmol) of D-mannose pentaacetate instead of β-D-glucose pentaacetate. The compound was obtained (222 mg, 7% yield in 2 steps) having the following properties:

$^1$H-NMR spectrum (300 MHz, CDCl$_3$, TMS) δ: 0.80-0.90 (m, 9H), 1.00-1.70 (m, 17H), 1.85-2.10 (m, 4H), 3.32-4.07 (m, 7H), 3.38 (m, 1H), 3.51 (d, J=9.8 Hz, 1H), 3.63 (m, 1H), 3.70-4.05 (m, 5H), 4.81 (s, 1H), 5.05 (brs, 1H).

Example 106

Synthesis of
1-O-(5,9,13-trimethyltetradec-4-enyl)-D-maltoside

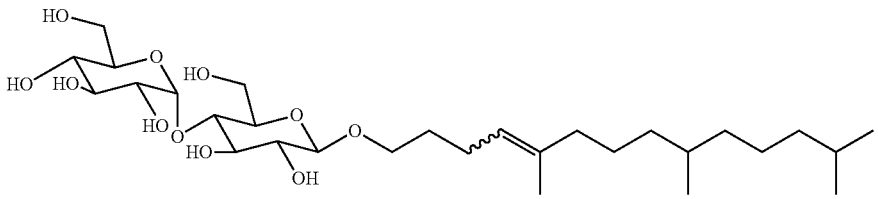 [SMILES: CC(=CCCCOC1OC(CO)C(OC2OC(CO)C(O)C(O)C2O)C(O)C1O)CCCC(C)CCCC(C)C]

6.93 g (10.2 mmol) of D-Maltose octaacetate and 2.0 g (7.9 mmol) of 5,9,13-trimethyltetradec-4-en-1-ol were dissolved in dry acetonitrile (8 mL). 2.0 mL (16 mmol) of boron trifluoride diethyl etherate complex was added to the solution with cooling on ice. The reaction mixture was allowed to warm up slowly to room temperature while being stirred for 24 hours before addition of 3.3 mL (24 mmol) of triethylamine at 0° C. The resulting solution was diluted with ethyl acetate, and washed with water, 1M hydrochloric acid, saturated sodium bicarbonate aqueous solution, and saturated brine, successively, and dried over sodium sulfate. After filtration, the filtrate was concentrated to obtain 1-O-(5,9,13-trimethyltetradec-4-enyl)-D-maltoside heptaacetate as a crude product.

The above obtained crude product of 1-O-(5,9,13-trimethyltetradec-4-enyl)-D-maltoside heptaacetate was dissolved in methanol/tetrahydrofuran (1:1, 8 mL), and 0.79 mL (0.79 mmol) of 1M sodium methylate in methanol was added at room temperature. After being stirred for 24 hours, 62 µL (0.86 mmol) of acetyl chloride was added to the reaction mixture and the mixture was confirmed to be weakly acidic. The mixture was concentrated, and the resulting residue was purified by silica gel column chromatography (methanol/methylene chloride mixture) to obtain 338 mg of the title compound (7% yield in 2 steps). The results of NMR analysis of the obtained compound are as shown below.

$^1$H-NMR spectrum (300 MHz, CD$_3$OD, TMS) δ: 0.80-0.90 (m, 9H), 1.00-1.70 (m, 17H), 1.90-2.10 (m, 4H), 3.10-3.95 (m, 14H), 4.24 (d, J=7.7 Hz, 1H), 4.60 (s, 2H), 5.13 (brs, 1H).

Example 107

Synthesis of
mono-O-(5,9,13-trimethyltetradec-4-enyl)glycerol

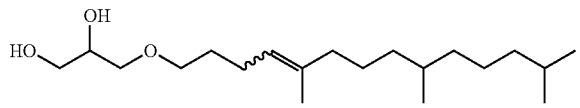 [SMILES: CC(=CCCCOCC(O)CO)CCCC(C)CCCC(C)C]

0.82 mL (5.9 mmol) of triethylamine, 0.90 g (4.7 mmol) of p-toluenesulfonyl chloride and 38 mg (0.39 mmol) of trimethylamine hydrochloride were added to a solution of 1.0 g (3.9 mmol) of 5,9,13-trimethyltetradec-4-en-1-ol in dry methylene chloride (3 mL) at 0° C., sequentially. After being stirred for 1 hour at room temperature, 0.12 mL (1.0 mmol) of N,N-dimethyl-1,3-propanediamine was added to the reaction mixture. After being stirred for 30 min, the mixture was diluted with ethyl acetate. The solution was washed with water, 1M hydrochloric acid, saturated sodium bicarbonate aqueous solution, and saturated brine, successively, and dried over anhydrous sodium sulfate. After filtration, the filtrate was concentrated to obtain (5,9,13-trimethyltetradec-4-enyl) tosylate as a crude product.

0.26 g (55%, 5.9 mmol) of sodium hydride was added to a solution of 0.54 g (5.9 mmol) of glycerol in dry N,N-dimethylformamide (6 mL) with cooling on ice. After the mixture was stirred for 30 min at 50° C., the above (5,9,13-trimethyltetradec-4-enyl)tosylate was added dropwise, with additional stirring for 18 hours at the same temperature. After addition of water at 0° C., the reaction mixture was extracted with ethyl acetate. The extract was washed with water, 1M hydrochloric acid, saturated sodium bicarbonate aqueous solution, and saturated brine, successively, and dried over anhydrous sodium sulfate. After filtration, the filtrate was concentrated, and the resulting residue was purified by silica gel column chromatography (ethyl acetate/hexane mixture) to obtain 73 mg of the title compound (6% yield in 2 steps). The results of NMR analysis of the obtained compound are as shown below.

$^1$H-NMR spectrum (300 MHz, CDCl$_3$, TMS) δ: 0.8-0.9 (m, 9H), 1.00-1.70 (m, 17H), 1.90-2.10 (m, 4H), 3.40-3.60 (m, 4H), 3.61-3.90 (m, 3H), 5.10 (brt, J=6.0 Hz, 1H).

Example 108

Synthesis of
mono-O-(5,9,13-trimethyltetradec-4-enyl)erythritol

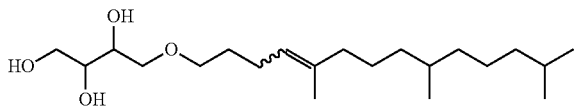 [SMILES: CC(=CCCCOCC(O)C(O)CO)CCCC(C)CCCC(C)C]

The title compound was synthesized using the same procedure as employed in Example 107, but with 0.72 g (5.9 mmol) of erythritol instead of glycerol. The compound was obtained (64 mg, 5% yield im 2 steps) having the following properties:

$^1$H-NMR spectrum (300 MHz, CDCl$_3$, TMS) δ: 0.8-0.9 (m, 9H), 1.00-1.70 (m, 17H), 1.90-2.10 (m, 4H), 2.29 (brs, OH), 2.64 (brs, OH), 2.75 (brs, OH), 3.49 (t, J=6.4 Hz, 2H), 3.59 (t, J=5.5 Hz, 2H), 3.65-3.90 (m, 4H), 5.09 (t, J=6.9 Hz, 1H).

Example 109

Synthesis of mono-O-(5,9,13-trimethyltetradec-4-enyl)pentaerythritol

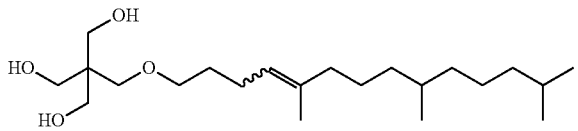 [SMILES: CC(=CCCCOCC(CO)(CO)CO)CCCC(C)CCCC(C)C]

The title compound was synthesized using the same procedure as employed in Example 107, but with 0.80 g (5.9 mmol) of pentaerythritol instead of glycerol. The compound was obtained (375 mg, 26% yield in 2 steps) having the following properties:

$^1$H-NMR spectrum (300 MHz, CDCl$_3$, TMS) δ: 0.8-0.9 (m, 9H), 1.00-1.70 (m, 17H), 1.90-2.10 (m, 4H), 2.59 (brs, 30H), 3.42 (t, J=6.4 Hz, 2H), 3.47 (s, 2H), 3.73 (d, 6H), 5.09 (t, J=7.0 Hz, 1H).

Example 110

Synthesis of mono-O-(5,9,13-trimethyltetradec-4-enyl)diglycerol

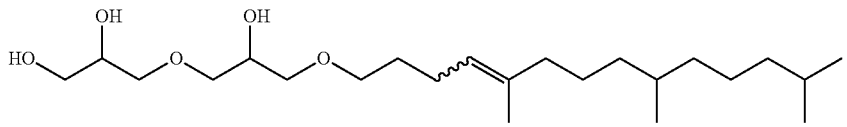 [SMILES: CC(=CCCCOCC(O)COCC(O)CO)CCCC(C)CCCC(C)C]

0.82 mL (5.9 mmol) of triethylamine, 0.90 g (4.7 mmol) of p-toluenesulfonyl chloride, and 38 mg (0.39 mmol) of trimethylamine hydrochloride were added to a solution of 5,9,13-trimethyltetradec-4-en-1-ol 1.0 g (3.9 mmol) in dry methylene chloride (3 mL) at 0° C., sequentially. After being stirred for 1 hour at room temperature, 0.12 mL (1.0 mmol) of N,N-dimethyl-1,3-propanediamine was added to the reaction mixture at 0° C. After being stirred for 30 min, the mixture was diluted with ethyl acetate. The solution was washed with water, 1M hydrochloric acid, saturated sodium bicarbonate aqueous solution, and saturated brine, successively, and dried over anhydrous sodium sulfate. After filtration, the filtrate was concentrated to obtain (5,9,13-trimethyltetradec-4-enyl) tosylate as a crude product.

0.26 g (55%, 5.9 mmol) of sodium hydride was added to a solution of 0.98 g (5.9 mmol) of diglycerol in dry N,N-dimethylformamide (6 mL) with cooling on ice. After the mixture was stirred for 30 min at 50° C., the above (5,9,13-trimethyltetradec-4-enyl)tosylate was added dropwise, with additional stirring for 18 hours at the same temperature. After addition of water at 0° C., the reaction mixture was extracted with ethyl acetate. The extract was washed with water, 1M hydrochloric acid, saturated sodium bicarbonate aqueous solution, and saturated brine, successively, and dried over anhydrous sodium sulfate. After filtration, the filtrate was concentrated, and the resulting residue was purified by silica gel column chromatography (methanol/methylene chloride mixture) to obtain 535 mg of the title compound (34% yield in 2 steps). The results of NMR analysis of the obtained compound are as shown below.

$^1$H-NMR spectrum (300 MHz, CDCl$_3$, TMS) δ: 0.8-0.9 (m, 9H), 1.00-1.70 (m, 17H), 1.90-2.10 (m, 4H), 3.40-4.00 (m, 12H), 5.10 (t, J=7.1 Hz, 1H).

Example 111

Synthesis of mono-O-(5,9,13-trimethyltetradec-4-enyl)triglycerol

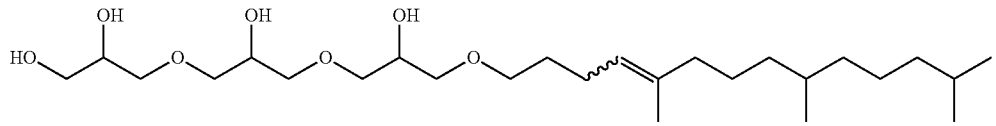 [SMILES: CC(=CCCCOCC(O)COCC(O)COCC(O)CO)CCCC(C)CCCC(C)C]

The title compound was synthesized using the same procedure as employed in Example 110, but with 1.42 g (5.9 mmol) of triglycerol instead of diglycerol. The compound was obtained (549 mg, 29% yield in 2 steps) having the following properties:

$^1$H-NMR spectrum (300 MHz, CDCl$_3$, TMS) δ: 0.8-0.9 (m, 9H), 1.00-1.68 (m, 14H), 1.58 and 1.67 (s, 3H, 5-CH$_3$), 1.90-2.10 (m, 4H), 3.40-4.00 (m, 17H), 5.09 (t, J=6.8 Hz, 1H).

Example 112

Synthesis of mono-O-(5,9,13-trimethyltetradec-4-enyl)xylitol

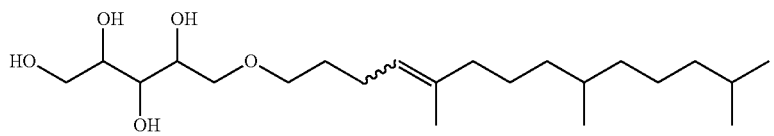 [SMILES: CC(=CCCCOCC(O)C(O)C(O)CO)CCCC(C)CCCC(C)C]

The title compound was synthesized using the same procedure as employed in Example 110, but with 0.90 g (5.9 mmol) of xylitol instead of diglycerol, having the following properties:

¹H-NMR spectrum (300 MHz, CDCl₃, TMS) δ: 0.8-0.9 (m, 9H), 1.00-1.70 (m, 17H), 1.90-2.10 (m, 4H), 3.40-4.00 (m, 9H), 5.10 (t, J=6.4 Hz, 1H).

Example 113

Synthesis of mono-O-(5,9,13-trimethyltetradec-4-enyl)mannitol

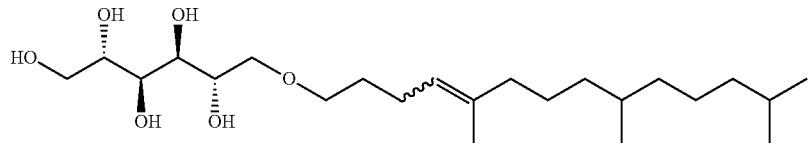 [SMILES: CC(=CCCCOC[C@H](O)[C@H](O)[C@@H](O)[C@@H](O)CO)CCCC(C)CCCC(C)C]

The title compound was synthesized using the same procedure as employed in Example 110, but with of mannitol instead of diglycerol. The compound was obtained (241 mg, 15% yield in 2 steps) having the following properties:

¹H-NMR spectrum (300 MHz, CDCl₃, TMS) δ: 0.8-0.9 (m, 9H), 1.00-1.70 (m, 14H), 1.57 and 1.66 (s, 3H, 5-CH₃), 1.85-2.10 (m, 4H), 3.40-3.95 (m, 10H), 5.07 (brs, 1H).

Example 114

Synthesis of mono-O-(5,9,13-trimethyltetradec-4-enyl)sorbitol

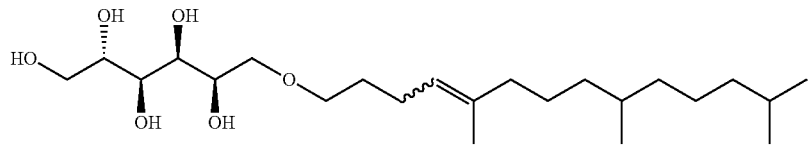 [SMILES: CC(=CCCCOC[C@@H](O)[C@H](O)[C@@H](O)[C@@H](O)CO)CCCC(C)CCCC(C)C]

The title compound was synthesized using the same procedure as employed in Example 110, but with 1.07 g (5.9 mmol) of sorbitol instead of diglycerol. The compound was obtained (216 mg, 13% yield in 2 steps) having the following properties:

¹H-NMR spectrum (300 MHz, CDCl₃, TMS) δ: 0.8-0.9 (m, 9H), 1.00-1.70 (m, 14H), 1.58 and 1.67 (s, 3H, 5-CH₃), 1.85-2.10 (m, 4H), 3.40-4.00 (m, 10H), 5.09 (brs, 1H).

Example 115

Synthesis of mono-O-(5,9,13-trimethyltetradec-4-enyl)dipentaerythritol

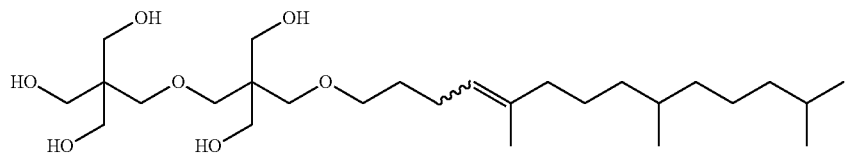 [SMILES: CC(=CCCCOCC(CO)(CO)COCC(CO)(CO)CO)CCCC(C)CCCC(C)C]

The title compound was synthesized using the same procedure as employed in Example 110, but with 1.5 g (5.9 mmol) of dipentaerythritol instead of diglycerol. The compound was obtained (245 mg, 13% yield in 2 steps) having the following properties:

¹H-NMR spectrum (300 MHz, CDCl₃+3% CD₃OD, TMS) δ: 0.8-0.9 (m, 9H), 1.00-1.65 (m, 14H), 1.58 and 1.67 (s, 3H, 5-CH₃), 1.90-2.05 (m, 4H), 3.35-3.49 (m, 8H), 3.52-3.65 (m, 10H), 5.09 (t, J=7.2 Hz, 1H).

Example 116

Synthesis of mono-O-(5,9,13-trimethyltetradec-4-enyl)ascorbic acid

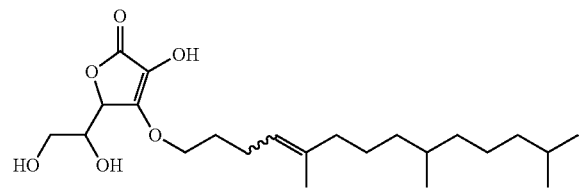 [SMILES: CC(=CCCCOC1=C(O)C(=O)OC1C(O)CO)CCCC(C)CCCC(C)C]

0.82 mL (5.9 mmol) of triethylamine, 0.90 g (4.7 mmol) of p-toluenesulfonyl chloride, 38 mg (0.39 mmol) of trimethylamine hydrochloride was added to a solution of 1.0 g (3.9 mmol) of 5,9,13-trimethyltetradec-4-en-1-ol in dry methylene chloride (3 mL) at 0° C., sequentially. After being stirred for 1 hour at room temperature, 0.12 mL (1.0 mmol) of N,N-dimethyl-1,3-propanediamine was added to the reaction mixture at 0° C. After being stirred for 30 min, the mixture was diluted with ethyl acetate. The resulting solution was washed with water, 1M hydrochloric acid, saturated sodium bicarbonate aqueous solution, and saturated brine, successively, and dried over anhydrous sodium sulfate. After filtration, the filtrate was concentrated to obtain (5,9,13-trimethyltetradec-4-enyl)tosylate as a crude product.

0.60 mL (4.3 mmol) of triethylamine was added and dissolved in a suspension of 0.69 g (3.9 mmol) of ascorbic acid in acetonitrile (8 mL). The above crude product of (5,9,13-trimethyltetradec-4-enyl)tosylate was added thereto at room temperature, and the reaction mixture was heated for 2 hours at 90° C. The reaction mixture was concentrated, and the resulting residue was purified by silica gel column chromatography (methanol/methylene chloride mixture) to obtain the title compound.

Example 117

Synthesis of 3,7,11-trimethyldodec-2-ene-1-nitrile

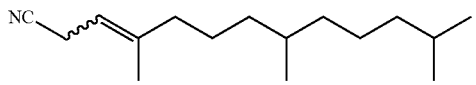 [SMILES: CC(=CCC#N)CCCC(C)CCCC(C)C]

82.3 g (617 mmol) of N-Chlorosuccinimide was suspended in methylene chloride (750 mL). After addition of 48 mL (0.65 mol) of dimethylsulfide at 0° C., the solution was stirred for 20 min. After addition of 69.8 g (0.308 mol) of tetrahydrofarnesol, the mixture was stirred for 1 hour at 0° C., with additional stirring for 1 hour at room temperature. After addition of saturated sodium bicarbonate aqueous solution, the reaction mixture was extracted with methylene chloride. The extract was washed with saturated brine, and dried over anhydrous sodium sulfate. After filtration, the filtrate was concentrated to obtain 3,7,11-trimethyldodec-2-ene-1-chloride as a crude product.

18.1 g (0.370 mol) of sodium cyanide was added to a solution of the above crude product of 3,7,11-trimethyl-dodec-2-ene-1-chloride in N,N-dimethylformamide (500 mL). The solution was stirred for 10 hours at room temperature. After addition of water at 0° C., the reaction mixture was extracted with ether. The extract was washed with saturated sodium bicarbonate aqueous solution and saturated brine, successively, and dried over sodium sulfate. After filtration, the filtrate was concentrated, and the resulting residue was purified by silica gel column chromatography (ethyl acetate/hexane mixture) to obtain 67.2 g of the title compound (93% yield in 2 steps) as a yellow liquid. The results of NMR analysis of the obtained compound are as shown below.

$^1$H-NMR spectrum (300 MHz, CDCl$_3$, TMS) δ: 0.80-0.90 (m, 9H), 1.00-1.75 (m, 12H), 1.66 and 1.74 (s, 3H, 3-CH$_3$), 2.00 (t, J=7.7 Hz, 2H), 3.04 (d, J=7.0 Hz, 2H), 5.16 (t, J=7.0 Hz, 1H).

Example 118

Synthesis of methyl 4,8,12-trimethyltridec-3-enoate

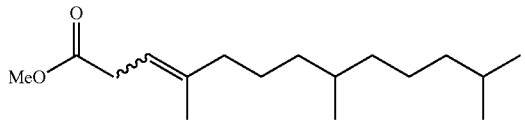 [SMILES: COC(=O)CC=C(C)CCCC(C)CCCC(C)C]

Water (130 mL) and 40 g (0.71 mol) of potassium hydroxide was added to a solution of 67.2 g (285 mmol) of 3,7,11-trimethyldodec-2-ene-1-nitrile in ethanol (470 mL). The solution was stirred for 18 hours at 80° C. After the reaction mixture was concentrated, and then neutralized with concentrated hydrochloric acid, and extracted with ethyl acetate. The extract was washed with saturated sodium bicarbonate aqueous solution and saturated brine, successively, and dried over sodium sulfate. After filtration, the filtrate was concentrated to obtain 4,8,12-trimethyltridec-3-enoic acid as a crude product.

The above obtained crude product of 4,8,12-trimethyl-tridec-3-enoic acid was dissolved in methanol (350 mL). Concentrated sulfuric acid (7 mL) was added thereto and stirred for 18 hours at room temperature. Sodium bicarbonate was slowly added to the reaction mixture and the mixture was confirmed to be neutralized. After filtration, the filtrate was concentrated, and diluted with ethyl acetate. The solution was washed with water and saturated brine, successively, and dried over anhydrous magnesium sulfate. After filtration, the filtrate was concentrated, and the resulting residue was purified by silica gel column chromatography (ethyl acetate/hexane mixture) to obtain 58.8 g of the title compound (77% yield in 2 steps) as a slightly yellow liquid. The results of NMR analysis of the obtained compound are as shown below.

$^1$H-NMR spectrum (300 MHz, CDCl$_3$, TMS) δ: 0.80-0.90 (m, 9H), 1.00-1.58 (m, 12H), 1.62 and 1.73 (s, 3H, 4-CH$_3$), 1.99 (t, J=7.7 Hz, 2H), 3.05 (d, J=7.1 Hz, 2H), 3.68 (s, 3H), 5.31 (t, J=7.1 Hz, 1H).

Example 119

Synthesis of 4,8,12-trimethyltridec-3-en-1-ol

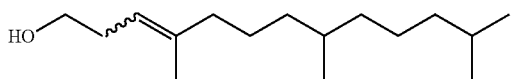 [SMILES: CC(=CCCO)CCCC(C)CCCC(C)C]

Under a nitrogen atmosphere, 12.4 g (0.326 mol) of lithium aluminum hydride was added little by little to a solution of 35 g (0.13 mol) of methyl 4,8,12-trimethyltridec-3-enoate in dry tetrahydrofuran (320 mL) at 0° C. After being stirred at 50° C. for 2 hours, the reaction mixture was cooled on ice, followed by careful addition of saturated sodium sulfate aqueous solution until the resulting gray suspension turned white. Sodium sulfate was added to the solution at room temperature for drying. After filtration, the filtrate was concentrated to obtain 31 g of the title compound (99% yield) as a colorless transparent liquid. The results of NMR analysis of the obtained compound are as shown below.

$^1$H-NMR spectrum (300 MHz, CDCl$_3$, TMS) δ: 0.80-0.90 (m, 9H), 1.00-1.60 (m, 12H), 1.63 and 1.72 (s, 3H, 4-CH$_3$), 1.94-2.07 (m, 2H), 2.29 (m, 2H), 3.63 (m, 2H), 5.12 (t, J=7.1 Hz, 1H).

Example 120

Synthesis of mono-O-(4,8,12-trimethyltridec-3-enoyl)glycerol

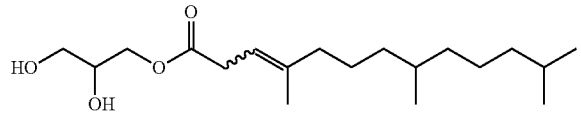 [SMILES: CC(=CCC(=O)OCC(O)CO)CCCC(C)CCCC(C)C]

1.0 g (3.7 mmol) of methyl 4,8,12-trimethyltridec-3-enoate was slowly added dropwise to a solution of 0.86 g (9.3 mmol) of glycerol and 0.62 g (4.4 mmol) of potassium carbonate in dry N,N-dimethylformamide (4 mL) at 100° C. After the reaction mixture was stirred at 100° C. for 18 hours, 1M hydrochloric acid was added. The resulting solution was extracted with ether, and the extract was washed with saturated sodium bicarbonate aqueous solution and saturated brine, successively, and dried over anhydrous sodium sulfate. After filtration, the filtrate was concentrated, and the resulting residue was purified by silica gel column chromatography (ethyl acetate/hexane mixture) to obtain 287 mg of the title compound (24% yield) as a colorless viscous liquid.

The results of 1H-NMR analysis of the obtained compound are as shown below.

$^1$H-NMR spectrum (300 MHz, CDCl$_3$, TMS) δ: 0.80-0.90 (m, 9H), 1.00-1.60 (m, 12H), 1.63 and 1.74 (s, 3H, 4-CH$_3$), 2.00 (t, J=7.2 Hz, 2H), 3.10 (d, J=7.1 Hz, 2H), 3.55-4.00 (m, 3H), 4.10-4.30 (m, 2H), 5.30 (t, J=7.1 Hz, 1H).

Example 121

Synthesis of mono-O-(4,8,12-trimethyltridec-3-enoyl)erythritol

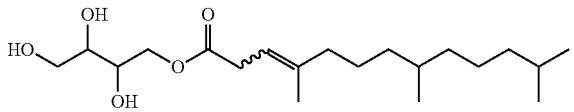 [SMILES: CC(=CCC(=O)OCC(O)C(O)CO)CCCC(C)CCCC(C)C]

The title compound was synthesized using the same procedure as employed in Example 120, but with 1.14 g (9.31 mmol) of erythritol instead of glycerol. The compound was obtained (246 mg, 19% yield) having the following properties:

$^1$H-NMR spectrum (300 MHz, CDCl$_3$, TMS) δ: 0.80-0.90 (m, 9H), 1.00-1.60 (m, 12H), 1.63 and 1.74 (s, 3H, 4-CH$_3$), 2.00 (t, J=7.2 Hz, 2H), 3.11 (d, J=7.1 Hz, 2H), 3.60-3.95 (m, 4H), 4.25-4.40 (m, 2H), 5.30 (t, J=7.1 Hz, 1H).

Example 122

Synthesis of mono-O-(4,8,12-trimethyltridec-3-enoyl)pentaerythritol

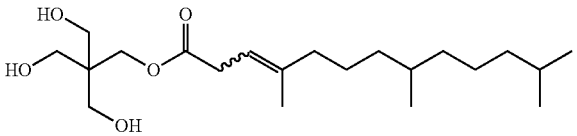 [SMILES: CC(=CCC(=O)OCC(CO)(CO)CO)CCCC(C)CCCC(C)C]

The title compound was synthesized using the same procedure as employed in Example 120, but with 1.27 g (9.31 mmol) of pentaerythritol instead of glycerol. The compound was obtained (196 mg, 15% yield) having the following properties:

$^1$H-NMR spectrum (300 MHz, CDCl$_3$, TMS) δ: 0.80-0.90 (m, 9H), 1.00-1.60 (m, 12H), 1.64 and 1.74 (s, 3H, 4-CH$_3$), 2.00 (t, J=7.6 Hz, 2H), 2.52 (brt, J=5.4 Hz, 3H, OH), 3.10 (d, J=7.2 Hz, 2H), 3.65 (d, J=5.4 Hz, 6H), 4.23 (s, 2H), 5.29 (t, J=7.2 Hz, 1H).

Example 123

Synthesis of mono-O-(4,8,12-trimethyltridec-3-enoyl)diglycerol

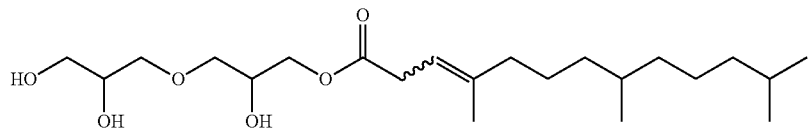 [SMILES: CC(=CCC(=O)OCC(O)COCC(O)CO)CCCC(C)CCCC(C)C]

1.0 g (3.7 mmol) of methyl 4,8,12-trimethyltridec-3-enoate was slowly added dropwise to a solution of 1.55 g (9.31 mmol) of diglycerol and 0.62 g (4.5 mmol) of potassium carbonate in dry N,N-dimethylformamide (4 mL) at 80° C. After the reaction mixture was stirred at 100° C. for 18 hours, 1M hydrochloric acid was added. The resulting extract was extracted with ethyl acetate, and the extract was washed with saturated sodium bicarbonate aqueous solution and saturated brine, successively, and dried over anhydrous sodium sulfate. After filtration, the filtrate was concentrated, and the resulting residue was purified by silica gel column chromatography (methanol/methylene chloride mixture) to obtain 163 mg of the title compound (11% yield).

The results of 1H-NMR analysis of the obtained compound are as shown below.

$^1$H-NMR spectrum (300 MHz, CDCl$_3$, TMS) δ: 0.80-0.90 (m, 9H), 1.00-1.60 (m, 12H), 1.62 and 1.73 (s, 3H, 4-CH$_3$), 1.99 (t, J=7.7 Hz, 2H), 3.09 (d, J=6.8 Hz, 2H), 3.50-4.30 (m, 10H), 5.30 (t, J=6.8 Hz, 1H).

Example 124

Synthesis of mono-O-(4,8,12-trimethyltridec-3-enoyl)triglycerol

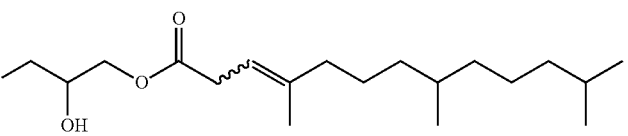

The title compound was synthesized using the same procedure as employed in Example 123, but with 2.24 g (9.31 mmol) of triglycerol instead of diglycerol. The compound was obtained (148 mg, 8% yield) having the following properties:

$^1$H-NMR spectrum (300 MHz, CDCl$_3$, TMS) δ: 0.80-0.90 (m, 9H), 1.00-1.60 (m, 12H), 1.62 and 1.73 (s, 3H, 4-CH$_3$), 1.99 (t, J=7.1 Hz, 2H), 3.09 (d, J=7.1 Hz, 2H), 3.50-4.25 (m, 15H), 5.30 (t, J=7.1 Hz, 1H).

Example 125

Synthesis of mono-O-(4,8,12-trimethyltridec-3-enoyl)xylitol

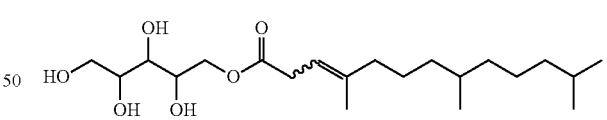

The title compound was synthesized using the same procedure as employed in Example 123, but with 1.42 g (9.31 mmol) of xylitol instead of diglycerol. The compound was obtained (284 mg, 20% yield) having the following properties:

¹H-NMR spectrum (300 MHz, CDCl₃, TMS) δ: 0.80-0.90 (m, 9H), 1.00-1.75 (m, 15H), 1.99 (t, J=6.6 Hz, 2H), 3.09 (d, J=7.1 Hz, 2H), 3.60-4.20 (m, 5H), 4.25 (d, J=5.7 Hz, 2H), 5.29 (t, J=7.1 Hz, 1H).

Example 126

Synthesis of mono-O-(4,8,12-trimethyltridec-3-enoyl)mannitol

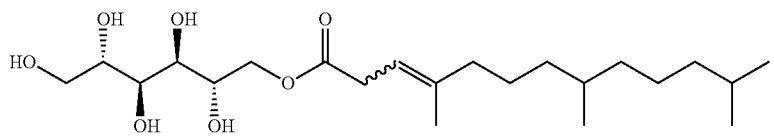 [SMILES: CC(=CCC(=O)OC[C@H](O)[C@H](O)[C@@H](O)[C@@H](O)CO)CCCC(C)CCCC(C)C]

The title compound was synthesized using the same procedure as employed in Example 123, but with 1.7 g (9.3 mmol) of mannitol instead of diglycerol. The compound was obtained (318 mg, 21% yield) having the following properties:

¹H-NMR spectrum (300 MHz, CDCl₃, TMS) δ: 0.80-0.90 (m, 9H), 1.00-1.60 (m, 12H), 1.61 and 1.72 (s, 3H, 4-CH₃), 1.98 (t, J=7.1 Hz, 2H), 3.10 (brt, 2H), 3.60-4.40 (m, 8H), 5.29 (brs, 1H).

Example 127

Synthesis of mono-O-(4,8,12-trimethyltridec-3-enoyl)sorbitol

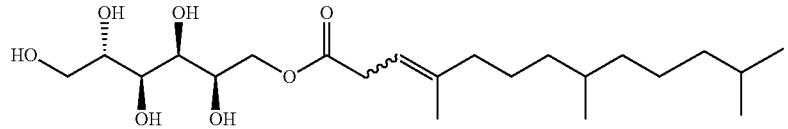 [SMILES: CC(=CCC(=O)OC[C@@H](O)[C@H](O)[C@@H](O)[C@@H](O)CO)CCCC(C)CCCC(C)C]

The title compound was synthesized using the same procedure as employed in Example 123, but with 1.7 g (9.3 mmol) of sorbitol instead of diglycerol. The compound was obtained (403 mg, 26% yield) having the following properties:

¹H-NMR spectrum (300 MHz, CDCl₃, TMS) δ: 0.80-0.90 (m, 9H), 1.00-1.60 (m, 12H), 1.62 and 1.73 (s, 3H, 4-CH₃), 2.00 (t, J=7.5 Hz, 2H), 3.11 (d, J=−6.8 Hz, 2H), 3.65-3.95 (m, 6H), 4.25 (dd, J=6.2, 11.6 Hz, 1H), 4.40 (dd, J=2.9, 11.6 Hz, 1H), 5.31 (t, J=6.8 Hz, 1H).

Example 128

Synthesis of mono-O-(4,8,12-trimethyltridec-3-enoyl)dipentaerythritol

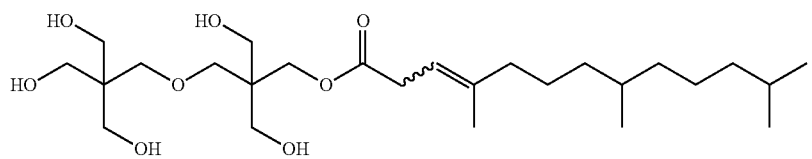 [SMILES: CC(=CCC(=O)OCC(CO)(CO)COCC(CO)(CO)CO)CCCC(C)CCCC(C)C]

The title compound was synthesized using the same procedure as employed in Example 123, but with 2.37 g (9.31 mmol) of dipentaerythritol instead of diglycerol. The compound was obtained (225 mg, 13% yield) having the following properties:

$^1$H-NMR spectrum (300 MHz, CDCl$_3$, TMS) δ: 0.80-0.90 (m, 9H), 1.00-1.70 (m, 15H), 2.00 (t, J=7.7 Hz, 2H), 3.08 (d, J=7.1 Hz, 2H), 3.38 (s, 2H), 3.42 (s, 2H), 3.55 (s, 4H), 3.59 (s, 6H), 4.08 (s, 2H), 5.28 (t, J=7.1 Hz, 1H).

Example 129

Synthesis of mono-O-(4,8,12-trimethyltridec-3-enoyl)ascorbic acid

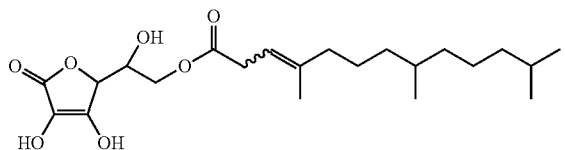 [SMILES: CC(=CCC(=O)OCC(O)C1OC(=O)C(O)=C1O)CCCC(C)CCCC(C)C]

0.65 g (3.7 mmol) of ascorbic acid was dissolved in concentrated sulfuric acid (18 mL). After addition of 1.0 g (3.7 mmol) of methyl 4,8,12-trimethyltridec-3-enoate, the mixture was stirred for 24 hours at room temperature. The reaction mixture was poured into iced water, and extracted with ethyl acetate. The extract was washed with water, 1M hydrochloric acid, saturated sodium bicarbonate aqueous solution, and saturated brine, successively, and dried over anhydrous sodium sulfate. After filtration, the filtrate was concentrated, and the resulting residue was purified by silica gel column chromatography (methanol/methylene chloride mixture) to obtain the title compound.

Example 130

Synthesis of 1-O-(4,8,12-trimethyltridec-3-enyl)-D-glucoside

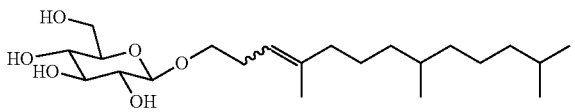 [SMILES: CC(=CCCOC1OC(CO)C(O)C(O)C1O)CCCC(C)CCCC(C)C]

2.11 g (5.41 mmol) of β-D-glucose pentaacetate and 1.0 g (4.2 mmol) of 4,8,12-trimethyltridec-3-en-1-ol were dissolved in dry acetonitrile (4 mL). 1.0 mL (8.3 mmol) of boron trifluoride diethyl etherate complex was added to the solution with cooling on ice. The reaction mixture was allowed to warm up slowly to room temperature while being stirred for 24 hours before addition of 1.7 mL (12 mmol) of triethylamine at 0° C. The resulting solution was diluted with ethyl acetate, and washed with water, 1M hydrochloric acid, saturated sodium bicarbonate aqueous solution, and saturated brine, successively, and dried over sodium sulfate. After filtration, the filtrate was concentrated to obtain 1-O-(4,8,12-trimethyltridec-3-enyl)-D-glucopyranoside tetraacetate as a crude product.

The above obtained crude product of 1-O-(4,8,12-trimethyltridec-3-enyl)-D-glucopyrano side tetraacetate was dissolved in methanol/tetrahydrofuran (1:1, 6 mL), and 0.42 mL (0.42 mmol) of 1M sodium methylate in methanol was added at room temperature. After being stirred for 24 hours, 30 μL (0.42 mmol) of acetyl chloride was added to the reaction mixture and confirmed to be neutralized. After addition of water, the solution was extracted with ethyl acetate. The extract was washed with saturated brine, and dried over anhydrous sodium sulfate. After filtration, the filtrate was concentrated, and the resulting residue was purified by silica gel column chromatography (methanol/methylene chloride mixture) to obtain the title compound. The results of NMR analysis of the obtained compound are as shown below.

$^1$H-NMR spectrum (300 MHz, CDCl$_3$, TMS) δ: 0.80-0.90 (m, 9H), 1.00-1.80 (m, 15H), 1.90-2.10 (m, 4H), 3.25-3.90 (m, 8H), 4.31 (brs, 1H), 5.12 (brs, 1H).

Example 131

Synthesis of 1-O-(4,8,12-trimethyltridec-3-enyl)-D-xylopyranoside

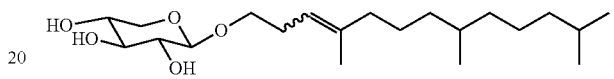

The title compound was synthesized using the same procedure as employed in Example 130, but with 1.72 g (5.41 mmol) of D-xylose tetraacetate instead of (3-D-glucose pentaacetate, having the following properties:

$^1$H-NMR spectrum (300 MHz, CDCl$_3$, TMS) δ: 0.80-0.90 (m, 9H), 1.00-1.80 (m, 15H), 1.90-2.10 (m, 4H), 3.30-4.10 (m, 7H), 4.35 (d, J=5.8 Hz, 0.7H), 4.80 (brs, 0.3H), 5.10 (brs, 1H).

Example 132

Synthesis of 1-O-(4,8,12-trimethyltridec-3-enyl)-D-galactoside

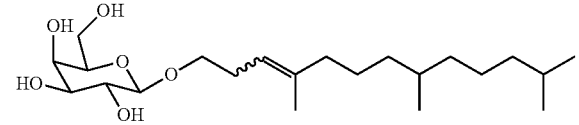 [SMILES: CC(=CCCOC1OC(CO)C(O)C(O)C1O)CCCC(C)CCCC(C)C]

The title compound was synthesized using the same procedure as employed in Example 130, but with 2.11 g (5.41 mmol) of D-galactose pentaacetate instead of β-D-glucose pentaacetate, having the following properties:

$^1$H-NMR spectrum (300 MHz, CDCl$_3$, TMS) δ: 0.80-0.90 (m, 9H), 1.00-1.80 (m, 15H), 1.85-2.10 (m, 4H), 3.40-4.10 (m, 8H), 4.26 (brs, 1H), 5.00-5.10 (m, 1H).

Example 133

Synthesis of 1-O-(4,8,12-trimethyltridec-3-enyl)-D-mannoside

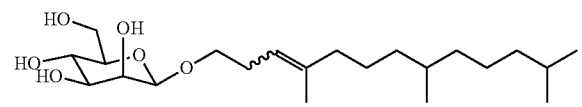 [SMILES: CC(=CCCOC1OC(CO)C(O)C(O)C1O)CCCC(C)CCCC(C)C]

The title compound was synthesized using the same procedure as employed in Example 130, but with 2.11 g (5.41 mmol) of D-mannose pentaacetate instead of β-D-glucose pentaacetate, having the following properties:

$^1$H-NMR spectrum (300 MHz, CDCl$_3$, TMS) δ: 0.80-0.90 (m, 9H), 1.00-1.70 (m, 15H), 1.90-2.10 (m, 4H), 3.30-3.65 (m, 3H), 3.73 (d, J=11.7 Hz, 1H), 3.80-4.10 (m, 3H), 4.81 (d, J=5.3 Hz, 1H), 5.10 (brs, 1H).

Example 134

Synthesis of 1-O-(4,8,12-trimethyltridec-3-enyl)-D-maltoside

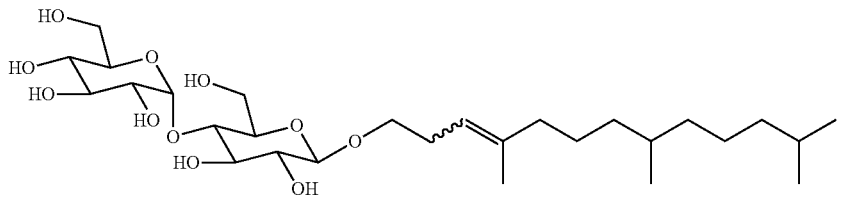 [SMILES: CC(=CCCOC1OC(CO)C(OC2OC(CO)C(O)C(O)C2O)C(O)C1O)CCCC(C)CCCC(C)C]

3.67 g (5.41 mmol) of D-mannose octaacetate and 1.0 g (4.2 mmol) of 4,8,12-trimethyltridec-3-en-1-ol were dissolved in dry acetonitrile (4 mL). 1.0 mL (8.0 mmol) of boron trifluoride diethyl etherate complex was added to the solution with cooling on ice. The reaction mixture was allowed to warm up slowly to room temperature while being stirred for 24 hours before addition of 1.7 mL (12 mmol) of triethylamine at 0° C. The resulting solution was diluted with ethyl acetate, and washed with water, 1M hydrochloric acid, saturated sodium bicarbonate aqueous solution, and saturated brine, successively, and dried over sodium sulfate. After filtration, the filtrate was concentrated to obtain 1-O-(4,8,12-trimethyltridec-3-enyl)-D-maltoside heptaacetate as a crude product.

The above obtained crude product of 1-O-(4,8,12-trimethyltridec-3-enyl)-D-maltoside heptaacetate was dissolved in methanol/tetrahydrofuran (1:1, 6 mL), and 0.42 mL (0.42 mmol) of 1M sodium methylate in methanol was added at room temperature. After being stirred for 24 hours, 30 µL (0.42 mmol) of acetyl chloride was added to the reaction mixture and the mixture was confirmed to be neutralized. The resulting mixture was concentrated, and the resulting residue was purified by silica gel column chromatography (methanol/methylene chloride mixture) to obtain the title compound. The results of NMR analysis of the obtained compound are as shown below.

$^1$H-NMR spectrum (300 MHz, CD$_3$OD, TMS) δ: 0.80-0.90 (m, 9H), 1.00-1.80 (m, 15H), 1.85-2.10 (m, 4H), 3.15-3.90 (m, 14H), 4.20-4.30 (m, 1H), 4.59 (s, 1H), 5.13 (brs, 2H).

Example 135

Synthesis of mono-O-(4,8,12-trimethyltridec-3-enyl)glycerol

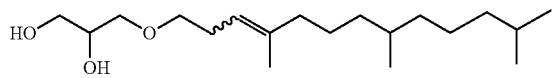 [SMILES: CC(=CCCOCC(O)CO)CCCC(C)CCCC(C)C]

0.63 mL (4.6 mmol) of triethylamine, 0.87 g (4.6 mmol) of p-toluenesulfonyl chloride, and 20 mg (0.21 mmol) of trimethylamine hydrochloride were added to a solution of 1.0 g (4.2 mmol) of 4,8,12-trimethyltridec-3-en-1-ol in dry methylene chloride (3 mL) at 0° C., sequentially. After being stirred for 2 hours at room temperature, 0.10 mL (0.83 mmol) of N,N-dimethyl-1,3-propanediamine was added to the reaction mixture at 0° C. After being stirred for 30 min, the mixture was diluted with ethyl acetate. The resulting solution was washed with water, 1M hydrochloric acid, saturated sodium bicarbonate aqueous solution, and saturated brine, successively, and then dried over anhydrous sodium sulfate. After filtration, the filtrate was concentrated to obtain (4,8,12-trimethyltridec-3-enyl)tosylate as a crude product.

0.27 g (55%, 6.2 mmol) of sodium hydride was added to a solution of glycerol 0.57 g (6.2 mmol) in dry N,N-dimethylformamide (6 mL) with cooling on ice. After the mixture was stirred for 30 min at 50° C., the above (4,8,12-trimethyltridec-3-enyl)tosylate was added dropwise, with additional stirring for 10 hours at the same temperature. After addition of water at 0° C., the reaction mixture was extracted with ethyl acetate. The extract was washed with water, 1M hydrochloric acid, saturated sodium bicarbonate aqueous solution, and saturated brine, successively, and dried over anhydrous sodium sulfate. After filtration, the filtrate was concentrated, and the resulting residue was purified by silica gel column chromatography (ethyl acetate/hexane mixture) to obtain 79 mg of the title compound (6% yield in 2 steps). The results of NMR analysis of the obtained compound are as shown below.

$^1$H-NMR spectrum (300 MHz, CDCl$_3$, TMS) δ: 0.80-0.90 (m, 9H), 1.00-1.70 (m, 15H), 1.90-2.05 (m, 2H), 2.15 (t, J=5.3 Hz, 1H, OH), 2.25-2.35 (m, 2H), 2.61 (d, J=5.2 Hz, 1H, OH), 3.40-3.90 (m, 7H), 5.10 (t, J=7.7 Hz, 1H).

Example 136

Synthesis of mono-O-(4,8,12-trimethyltridec-3-enyl)erythritol

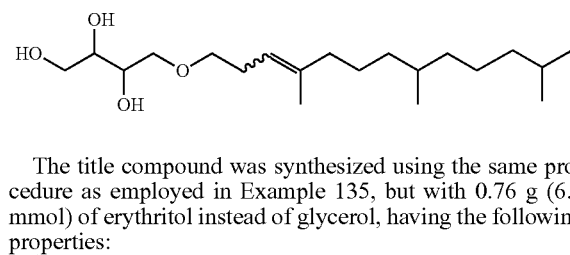

The title compound was synthesized using the same procedure as employed in Example 135, but with 0.76 g (6.2 mmol) of erythritol instead of glycerol, having the following properties:

$^1$H-NMR spectrum (300 MHz, CDCl$_3$, TMS) δ: 0.80-0.90 (m, 9H), 1.00-1.70 (m, 15H), 1.90-2.00 (m, 2H), 2.20-2.35 (m, 2H), 3.40-3.85 (m, 8H), 5.10 (brs, 1H).

Example 137

Synthesis of mono-O-(4,8,12-trimethyltridec-3-enyl)pentaerythritol

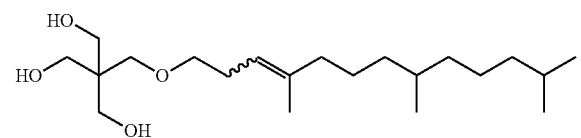 [SMILES: CC(=CCCOCC(CO)(CO)CO)CCCC(C)CCCC(C)C]

The title compound was synthesized using the same procedure as employed in Example 135, but with 0.85 g (6.2 mmol) of pentaerythritol instead of glycerol. The compound was obtained (191 mg, 13% yield in 2 steps) having the following properties:

¹H-NMR spectrum (300 MHz, CDCl₃, TMS) δ: 0.80-0.90 (m, 9H), 1.00-1.70 (m, 15H), 1.90-2.05 (m, 2H), 2.20-2.35 (m, 2H), 2.52 (t, J=5.6 Hz, 3H, OH), 3.38-3.48 (m, 2H), 3.49 (s, 2H), 3.71 (d, J=5.6 Hz, 6H), 5.09 (t, J=6.8 Hz, 1H).

Example 138

Synthesis of mono-O-(4,8,12-trimethyltridec-3-enyl)diglycerol

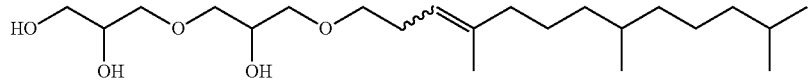 [SMILES: CC(=CCCOCC(O)COCC(O)CO)CCCC(C)CCCC(C)C]

0.63 mL (4.6 mmol) of triethylamine, 0.87 g (4.6 mmol) of p-toluenesulfonyl chloride, 20 mg (0.21 mmol) of trimethylamine hydrochloride were added to a solution of 1.0 g (4.2 mmol) of 4,8,12-trimethyltridec-3-en-1-ol in dry methylene chloride (3 mL) at 0° C., sequentially. After being stirred for 2 hours at room temperature, N,N-dimethyl-1,3-propanediamine was added to the reaction mixture at 0° C. After being stirred for 30 min, the mixture was diluted with ethyl acetate. The resulting solution was washed with water, 1M hydrochloric acid, saturated sodium bicarbonate aqueous solution, and saturated brine, successively, and dried over anhydrous sodium sulfate. After filtration, the filtrate was concentrated to obtain (4,8,12-trimethyltridec-3-enyl)tosylate as a crude product.

0.27 g (55%, 6.2 mmol) of sodium hydride was added to a solution of 1.04 g (6.2 mmol) of diglycerol in dry N,N-dimethylformamide (6 mL) with cooling on ice. After the mixture was stirred for 30 min at 50° C., the above (4,8,12-trimethyltridec-3-enyl)tosylate was added dropwise with additional stirring for 18 hours at the same temperature. After addition of water at 0° C., the reaction mixture was extracted with ethyl acetate. The extract was washed with water, 1M hydrochloric acid, saturated sodium bicarbonate aqueous solution, and saturated brine, successively, and dried over anhydrous sodium sulfate. After filtration, the filtrate was concentrated, and the resulting residue was purified by silica gel column chromatography (methanol/methylene chloride mixture) to obtain 351 mg of the title compound (22% yield in 2 steps). The results of NMR analysis of the obtained compound are as shown below.

¹H-NMR spectrum (300 MHz, CDCl₃, TMS) δ: 0.80-0.90 (m, 9H), 1.00-1.70 (m, 15H), 1.90-2.05 (m, 2H), 2.20-2.35 (m, 2H), 3.40-4.00 (m, 12H), 5.10 (brs, 1H).

Example 139

Synthesis of mono-O-(4,8,12-trimethyltridec-3-enyl)triglycerol

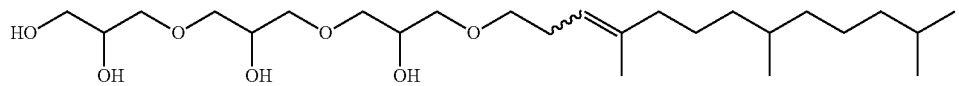 [SMILES: CC(=CCCOCC(O)COCC(O)COCC(O)CO)CCCC(C)CCCC(C)C]

The title compound was synthesized using the same procedure as employed in Example 138, but with 1.5 g (6.2 mmol) of triglycerol instead of diglycerol, having the following properties:

¹H-NMR spectrum (300 MHz, CDCl₃, TMS) δ: 0.80-0.90 (m, 9H), 1.00-1.60 (m, 12H), 1.61 and 1.69 (s, 3H, 4-CH₃), 1.90-2.05 (m, 2H), 2.25-2.35 (m, 2H), 3.40-4.00 (m, 17H), 5.10 (brs,

Example 140

Synthesis of mono-O-(4,8,12-trimethyltridec-3-enyl)xylitol

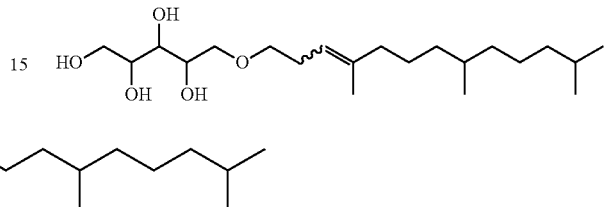

The title compound was synthesized using the same procedure as employed in Example 138, but with 0.95 g (6.2 mmol) of xylitol instead of diglycerol, having the following properties:

¹H-NMR spectrum (300 MHz, CDCl₃, TMS) δ: 0.80-0.90 (m, 9H), 1.00-1.70 (m, 15H), 1.90-2.05 (m, 2H), 2.20-2.35 (m, 2H), 3.40-4.00 (m, 9H), 5.10 (brs, 1H).

Example 141

Synthesis of mono-O-(4,8,12-trimethyltridec-3-enyl)mannitol

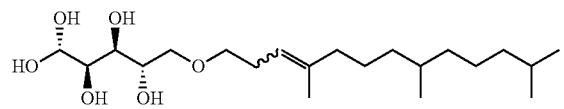

The title compound was synthesized using the same procedure as employed in Example 138, but with 1.14 g (6.24 mmol) of mannitol instead of diglycerol. The compound was obtained (135 mg, 8% yield in 2 steps) having the following prop ¹H-NMR spectrum (300 MHz, CDCl₃, TMS) δ: 0.80-0.90 (m, 9H), 1.00-1.63 (m, 12H), 1.60 and 1.68 (s, 3H, 4-CH₃), 1.85-2.05 (m, 2H), 2.20-2.35 (m, 2H), 3.40-3.95 (m, 10H), 5.07 (brs, 1H). erties:

Example 142

Synthesis of mono-O-(4,8,12-trimethyltridec-3-enyl)sorbitol

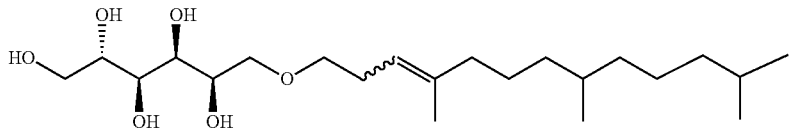 [SMILES: CC(=CCCOC[C@@H](O)[C@H](O)[C@@H](O)[C@@H](O)CO)CCCC(C)CCCC(C)C]

The title compound was synthesized using the same procedure as employed in Example 138, but with 1.14 g (6.24 mmol) of sorbitol instead of diglycerol. The compound was obtained (103 mg, 6% yield in 2 steps) having the following properties:

$^1$H-NMR spectrum (300 MHz, CDCl$_3$, TMS) δ: 0.80-0.90 (m, 9H), 1.00-1.58 (m, 12H), 1.60 and 1.68 (s, 3H, 4-CH$_3$), 1.90-2.03 (m, 2H), 2.20-2.35 (m, 2H), 3.40-4.00 (m, 10H), 5.08 (brs, 1H).

Example 143

Synthesis of mono-O-(4,8,12-trimethyltridec-3-enyl) dipentaerythritol

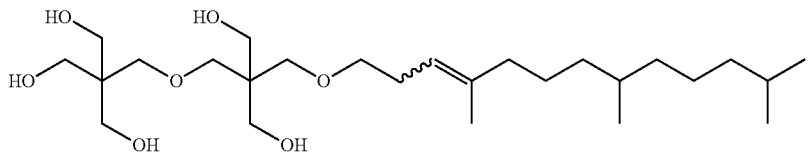 [SMILES: CC(=CCCOCC(CO)(CO)COCC(CO)(CO)CO)CCCC(C)CCCC(C)C]

The title compound was synthesized using the same procedure as employed in Example 138, but with 1.59 g (6.24 mmol) of dipentaerythritol instead of diglycerol, having the following properties:

$^1$H-NMR spectrum (300 MHz, CDCl$_3$, TMS) δ: 0.80-0.90 (m, 9H), 1.00-1.80 (m, 15H), 1.85-2.05 (m, 2H), 2.15-2.30 (m, 2H), 3.30-3.70 (m, 18H), 5.08 (brs, 1H).

Example 144

Synthesis of mono-O-(4,8,12-trimethyltridec-3-enyl)ascorbic acid

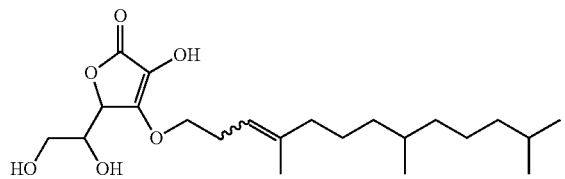 [SMILES: CC(=CCCOC1=C(O)C(=O)OC1C(O)CO)CCCC(C)CCCC(C)C]

0.63 mL (4.6 mmol) of triethylamine, 0.87 g (4.6 mmol) of p-toluenesulfonyl chloride, and 20 mg (0.21 mmol) of trimethylamine hydrochloride were added to a solution of 1.0 g (4.2 mmol) of 4,8,12-trimethyltridec-3-en-1-ol in dry methylene chloride (3 mL) at 0° C., sequentially. After being stirred for 2 hours at room temperature, 0.10 mL (0.83 mmol) of N,N-dimethyl-1,3-propanediamine was added to the reaction mixture at 0° C. After being stirred for 30 min, the mixture was diluted with ethyl acetate. The resulting solution was washed with water, 1M hydrochloric acid, saturated sodium bicarbonate aqueous solution, and saturated brine, successively, and dried over anhydrous sodium sulfate. After filtration, the filtrate was concentrated to obtain (4,8,12-trimethyltridec-3-enyl)tosylate as a crude product.

0.63 mL (4.6 mmol) of triethylamine was added and dissolved in a suspension of 0.73 g (4.2 mmol) of ascorbic acid in acetonitrile (9 mL). After the above crude product of (4,8,12-trimethyltridec-3-enyl)tosylate was added at room temperature, the reaction mixture was heated for 2 hours at 90° C. The reaction mixture was concentrated, and the resulting residue was purified by silica gel column chromatography (methanol/methylene chloride mixture) to obtain the title compound. The results of NMR analysis of the obtained compound are as shown below.

$^1$H-NMR spectrum (300 MHz, CDCl$_3$, TMS) δ: 0.80-0.90 (m, 9H), 1.00-1.60 (m, 12H), 1.63 and 1.69 (s, 3H, 4-CH$_3$), 1.90-2.10 (m, 2H), 2.46 (td, J=6.8, 7.4 Hz, 2H), 3.63 (d, J=6.6 Hz, 2H), 3.82 (t, J=6.6 Hz, 1H), 4.30-4.53 (m, 2H), 4.74 (s, 1H), 5.17 (t, J=6.8 Hz, 1H).

Example 145

Synthesis of methyl 3,7,11-trimethyldodec-2-enoate

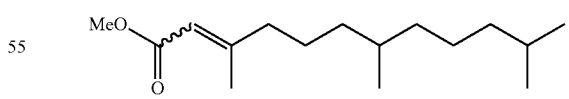

Under a nitrogen atmosphere, 9.0 mL (0.10 mol) of oxalyl chloride was dissolved in methylene chloride (170 mL), and 18 mL (0.25 mol) of dimethyl sulfoxide was slowly added dropwise to the mixture at −78° C. After the mixture was stirred for 15 min, 19.7 g (87.0 mmol) of tetrahydrofarnesol was added, followed by stirring for 1 hour at the same temperature. After addition of 48 mL (0.35 mol) of triethylamine, the reaction mixture was allowed to warm up to room temperature. The methylene chloride was concentrated and diluted with diethylether. The solution was washed with saturated brine, and dried over anhydrous sodium sulfate. After filtration, the filtrate was concentrated to obtain 3,7,11-trimethyldodec-2-en-1-al as a crude product.

The above obtained crude product of 3,7,11-trimethyldodec-2-en-1-al was dissolved in t-butanol (90 mL) and water (90 mL). 20.4 g (0.131 mmol) of sodium dihydrogen phosphate, 10.1 g (0.104 mmol) of amidosulfuric acid, 9.4 g (0.10 mmol) of sodium chlorite were added to the solution. After being stirred for 3 hours at room temperature, the reaction mixture was diluted with ether. The solution was washed with water and saturated brine, successively, and dried over anhydrous sodium sulfate. After filtration, the filtrate was concentrated to obtain 3,7,11-trimethyldodec-2-enoic acid as a crude product.

The above obtained crude product of 3,7,11-trimethyldodec-2-enoic acid was dissolved in methanol (220 mL), and concentrated sulfuric acid (0.5 mL) was added. After being stirred for 13 hours at 60° C., sodium bicarbonate was slowly added to the reaction mixture and the mixture was confirmed to be neutralized. After filtration, the filtrate was concentrated, and then diluted with ethyl acetate. The solution was washed with water and saturated brine, successively, and dried over anhydrous sodium sulfate. After filtration, the filtrate was concentrated, and the resulting residue was purified by silica gel column chromatography (ethyl acetate/hexane mixture) to obtain 10.7 g of the title compound (48% yield in 3 steps) as a slightly yellow liquid. The results of NMR analysis of the obtained compound are as shown below.

$^1$H-NMR spectrum (300 MHz, CDCl$_3$, TMS) δ: 0.80-0.90 (m, 9H), 1.00-1.60 (m, 12H), 1.88 and 2.15 (s, 3H, 3-CH$_3$), 2.11 (t, J=7.2 Hz, 1.1H, 4-CH$_2$), 2.60 (t, J=7.9 Hz, 0.9H, 4-CH$_2$), 3.67 and 3.69 (s, 3H, OMe), 5.66 and 5.67 (s, 1H, 2-CH).

Example 146

Synthesis of mono-O-(3,7,11-trimethyldodec-2-enoyl)glycerol

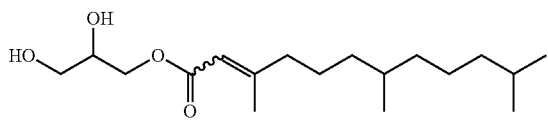 [SMILES: CC(=CC(=O)OCC(O)CO)CCCC(C)CCCC(C)C]

0.90 g (3.5 mmol) of methyl 3,7,11-trimethyldodec-2-enoate was slowly added dropwise to a solution of 0.59 g (6.4 mmol) of glycerol and 0.88 g (6.4 mmol) of potassium carbonate in dry N,N-dimethylformamide (3 mL) at 100° C. After the reaction mixture was stirred at 100° C. for 18 hours, 1M hydrochloric acid was added. The resulting solution was extracted with ether, and the extract was washed with saturated sodium bicarbonate aqueous solution and saturated brine, successively, and dried over anhydrous sodium sulfate. After filtration, the filtrate was concentrated, and the resulting residue was purified by silica gel column chromatography (ethyl acetate/hexane mixture) to obtain 318 mg of the title compound (29% yield) as a colorless viscous product.

The results of 1H-NMR analysis of the obtained compound are as shown below.

$^1$H-NMR spectrum (300 MHz, CDCl$_3$, TMS) δ: 0.80-0.95 (m, 9H), 1.00-1.80 (m, 12H), 1.91 and 2.16 (s, 3H, 3-CH$_3$), 2.10-2.20 (m, 2H), 2.61 (brs, OH), 3.50-4.00 (m, 3H), 4.10-4.30 (m, 2H), 5.70 (brs, 1H).

Example 147

Synthesis of mono-O-(3,7,11-trimethyldodec-2-enoyl)erythritol

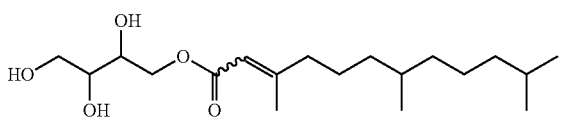 [SMILES: CC(=CC(=O)OCC(O)C(O)CO)CCCC(C)CCCC(C)C]

The title compound was synthesized using the same procedure as employed in Example 146, but with 0.78 g (6.4 mmol) of erythritol instead of glycerol. The compound was obtained (283 mg, 23% yield) having the following properties:

$^1$H-NMR spectrum (300 MHz, CDCl$_3$, TMS) δ: 0.80-0.95 (m, 9H), 1.00-1.80 (m, 12H), 1.92 and 2.17 (s, 3H, 3-CH$_3$), 2.10-2.20 (m, 2H), 3.60-4.00 (m, 4H), 4.20-4.45 (m, 2H), 5.72 (brs, 1H).

Example 148

Synthesis of mono-O-(3,7,11-trimethyldodec-2-enoyl)pentaerythritol

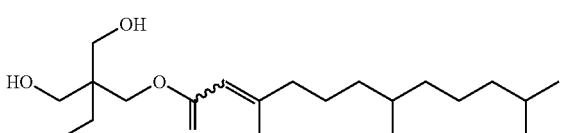

The title compound was synthesized using the same procedure as employed in Example 146, but with 0.87 g (6.4 mmol) of pentaerythritol instead of glycerol. The compound was obtained (459 mg, 36% yield) having the following properties:

$^1$H-NMR spectrum (300 MHz, CDCl$_3$, TMS) δ: 0.80-0.95 (m, 9H), 1.00-1.80 (m, 12H), 1.92 and 2.17 (s, 3H, 3-CH$_3$), 2.10-2.20 (m, 2H), 2.70 (brs, 30H), 3.65 (s, 6H), 4.20-4.30 (m, 2H), 5.70 (brs, 1H).

Example 149

Synthesis of mono-O-(3,7,11-trimethyldodec-2-enoyl)diglycerol

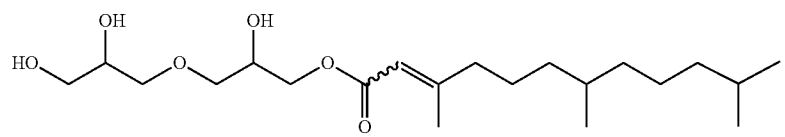 [SMILES: CC(=CC(=O)OCC(O)COCC(O)CO)CCCC(C)CCCC(C)C]

0.90 g (3.5 mmol) of methyl 3,7,11-trimethyldodec-2-enoate was slowly added dropwise to a solution of 1.06 g (6.37 mmol) of diglycerol and 0.88 g (6.4 mmol) of potassium carbonate in dry N,N-dimethylformamide (3 mL) at 100° C. After the reaction mixture was stirred at 100° C. for 18 hours, 1M hydrochloric acid was added. The resulting solution was extracted with ethyl acetate, and the extract was washed with saturated sodium bicarbonate aqueous solution and saturated brine, successively, and dried over anhydrous sodium sulfate. After filtration, the filtrate was concentrated, and the resulting residue was purified by silica gel column chromatography (methanol/methylene chloride mixture) to obtain 322 mg of the title compound (23% yield) as a slightly yellow viscous product.

The results of 1H-NMR analysis of the obtained compound are as shown below.

$^1$H-NMR spectrum (300 MHz, CDCl$_3$, TMS) δ: 0.80-0.95 (m, 9H), 1.00-1.80 (m, 12H), 1.90 and 2.16 (s, 3H, 3-CH$_3$), 2.10-2.20 (m, 2H), 3.40-4.30 (m, 10H), 5.70 (brs, 1H).

Example 150

Synthesis of mono-O-(3,7,11-trimethyldodec-2-enoyl)triglycerol

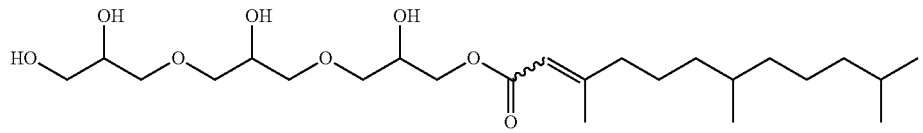 [SMILES: CC(=CC(=O)OCC(O)COCC(O)COCC(O)CO)CCCC(C)CCCC(C)C]

The title compound was synthesized using the same procedure as employed in Example 149, but with 1.53 g (6.4 mmol) of triglycerol instead of diglycerol. The compound was obtained (291 mg, 18% yield) having the following properties:

$^1$H-NMR spectrum (300 MHz, CDCl$_3$, TMS) δ: 0.80-0.95 (m, 9H), 1.00-1.80 (m, 12H), 1.90 and 2.15 (s, 3H, 3-CH$_3$), 2.10-2.20 (m, 2H), 3.45-4.20 (m, 15H), 5.70 (brs, Example 151

Synthesis of mono-O-(3,7,11-trimethyldodec-2-enoyl)xylitol

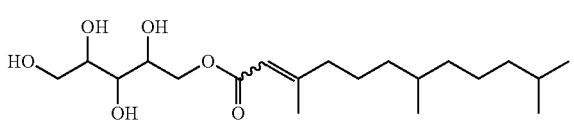 [SMILES: CC(=CC(=O)OCC(O)C(O)C(O)CO)CCCC(C)CCCC(C)C]

The title compound was synthesized using the same procedure as employed in Example 149, but with 0.97 g (6.4 mmol) of xylitol instead of diglycerol. The compound was obtained (169 mg, 13% yield) having the following properties:

$^1$H-NMR spectrum (300 MHz, CDCl$_3$, TMS) δ: 0.80-0.95 (m, 9H), 1.00-1.80 (m, 12H), 1.90 and 2.16 (s, 3H, 3-CH$_3$), 2.10-2.20 (m, 2H), 3.30-4.40 (m, 7H), 5.69 (brs, 1H).

Example 152

Synthesis of mono-O-(3,7,11-trimethyldodec-2-enoyl)mannitol

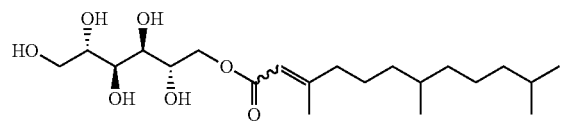 [SMILES: CC(=CC(=O)OC[C@H](O)[C@H](O)[C@@H](O)[C@@H](O)CO)CCCC(C)CCCC(C)C]

The title compound was synthesized using the same procedure as employed in Example 149, but with 1.16 g (6.37 mmol) of mannitol instead of diglycerol. The compound was obtained (183 mg, 13% yield) having the following properties:

$^1$H-NMR spectrum (300 MHz, CDCl$_3$+3% CD$_3$OD, TMS) δ: 0.80-0.95 (m, 9H), 1.00-1.80 (m, 12H), 1.91 and 2.16 (s, 3H, 3-CH$_3$), 2.10-2.20 (m, 2H), 3.65-3.95 (m, 6H), 4.20-4.45 (m, 2H), 5.74 (brs, 1H).

Example 153

Synthesis of mono-O-(3,7,11-trimethyldodec-2-enoyl)sorbitol

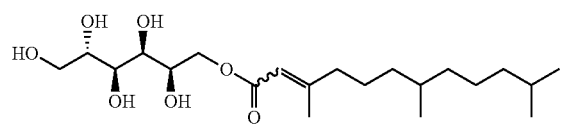 [SMILES: CC(=CC(=O)OC[C@@H](O)[C@H](O)[C@@H](O)[C@@H](O)CO)CCCC(C)CCCC(C)C]

The title compound was synthesized using the same procedure as employed in Example 149, but with 1.16 g (6.37 mmol) of sorbitol instead of diglycerol. The compound was obtained (184 mg, 13% yield) having the following properties:

$^1$H-NMR spectrum (300 MHz, CDCl$_3$, TMS) δ: 0.80-0.90 (m, 9H), 1.00-1.80 (m, 12H), 1.90-2.20 (m, 5H), 3.60-4.40 (m, 8H), 5.72 (brs, 1H).

Example 154

Synthesis of mono-O-(3,7,11-trimethyldodec-2-enoyl)dipentaerythritol

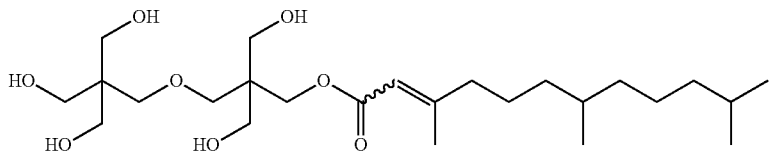 [SMILES: CC(=CC(=O)OCC(CO)(CO)COCC(CO)(CO)CO)CCCC(C)CCCC(C)C]

The title compound was synthesized using the same procedure as employed in Example 149, but with 1.62 g (6.37 mmol) of dipentaerythritol instead of diglycerol. The compound was obtained (101 mg, 6% yield) having the following properties:

$^1$H-NMR spectrum (300 MHz, CDCl$_3$+3% CD$_3$OD, TMS) δ: 0.80-0.90 (m, 9H), 1.00-1.80 (m, 12H), 1.91 and 2.16 (s, 3H, 3-CH$_3$), 2.10-2.20 (m, 2H), 3.35-3.45 (m, 4H), 3.50-3.60 (m, 8H), 4.08 (d, J=4.7 Hz, 2H), 5.68 (brs, 1H).

Example 155

Synthesis of mono-O-(3,7,11-trimethyldodec-2-enoyl)ascorbic acid

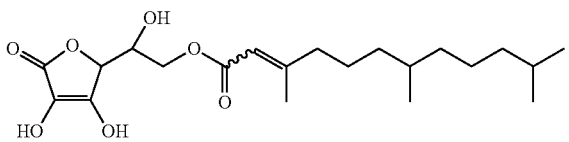 [SMILES: CC(=CC(=O)OCC(O)C1OC(=O)C(O)=C1O)CCCC(C)CCCC(C)C]

0.69 g (3.9 mmol) of ascorbic acid was dissolved in concentrated sulfuric acid (18 mL). After addition of 1.0 g (3.9 mmol) of methyl 3,7,11-trimethyldodec-2-enoate, the mixture was stirred for 24 hours at room temperature. The reaction mixture was poured into iced water, and extracted with ethyl acetate. The extract was washed with water, 1M hydrochloric acid, saturated sodium bicarbonate aqueous solution, and saturated brine, successively, and dried over anhydrous sodium sulfate. After filtration, the filtrate was concentrated, and the resulting residue was purified by silica gel column chromatography (methanol/methylene chloride mixture) to obtain the title compound.

Example 156

Synthesis of 1-O-(3,7,11-trimethyldodec-2-enyl)-D-glucoside

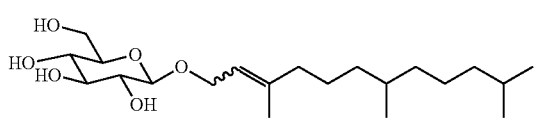 [SMILES: CC(=CCOC1OC(CO)C(O)C(O)C1O)CCCC(C)CCCC(C)C]

2.24 g (5.74 mmol) of β-D-glucose pentaacetate and 1.0 g (4.4 mmol) of tetrahydrofarnesol were dissolved in dry acetonitrile (8 mL). 1.12 mL (8.83 mmol) of boron trifluoride diethyl etherate complex was added to the solution with cooling on ice. The reaction mixture was allowed to warm up slowly to room temperature while being stirred for 24 hours before addition of 1.8 mL (13 mmol) of triethylamine at 0° C.

The resulting solution was diluted with ethyl acetate, and washed with water, 1M hydrochloric acid, saturated sodium bicarbonate aqueous solution, and saturated brine, successively, and dried over sodium sulfate. After filtration, the filtrate was concentrated to obtain 1-O-(3,7,11-trimethyldodec-2-enyl)-D-glucopyranoside tetraacetate as a crude product.

The above obtained crude product of 1-O-(3,7,11-trimethyldodec-2-enyl)-D-glucopyranoside tetraacetate was dissolved in methanol/tetrahydrofuran (1:1, 6 mL), and 0.45 mL (0.45 mmol) of 1M sodium methylate in methanol was added at room temperature. After being stirred for 24 hours, 33 µL (0.46 mmol) of acetyl chloride was added to the reaction mixture and the mixture was confirmed to be neutralized. After addition of water, the solution was extracted with ethyl acetate. The extract was washed with saturated brine, and dried over anhydrous sodium sulfate. After filtration, the filtrate was concentrated, and the resulting residue was purified by silica gel column chromatography (methanol/methylene chloride mixture) to obtain the title compound.

Example 157

Synthesis of 1-O-(3,7,11-trimethyldodec-2-enyl)-D-xylopyranoside

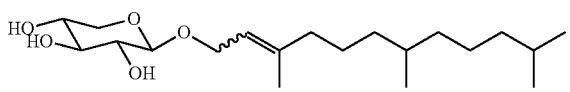 [SMILES: CC(=CCOC1OCC(O)C(O)C1O)CCCC(C)CCCC(C)C]

The title compound was synthesized using the same procedure as employed in Example 156, but with 1.83 g (5.74 mmol) of D-xylose tetraacetate instead of β-D-glucose pentaacetate.

Example 158

Synthesis of 1-O-(3,7,11-trimethyldodec-2-enyl)-D-galactoside

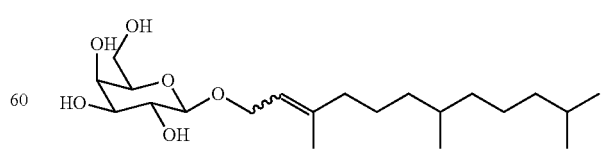

The title compound was synthesized using the same procedure as employed in Example 156, but with 2.24 g (5.74 mmol) of D-galactose pentaacetate instead of β-D-glucose pentaacetate.

Example 159

Synthesis of
1-O-(3,7,11-trimethyldodec-2-enyl)-D-mannoside

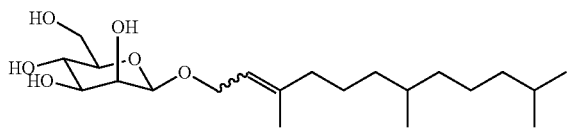 [SMILES: CC(=CCOC1OC(CO)C(O)C(O)C1O)CCCC(C)CCCC(C)C]

The title compound was synthesized using the same procedure as employed in Example 156, but with 2.24 g (5.74 mmol) of D-mannose pentaacetate instead of (3-D-glucose pentaacetate.

Example 160

Synthesis of
1-O-(3,7,11-trimethyldodec-2-enyl)-D-maltoside

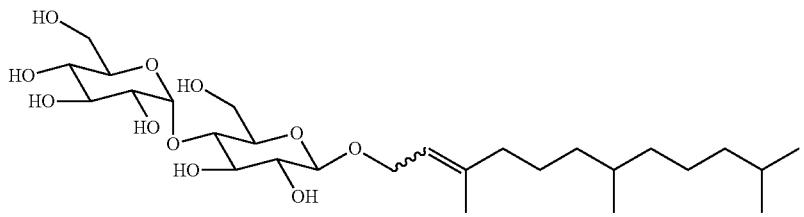 [SMILES: CC(=CCOC1OC(CO)C(OC2OC(CO)C(O)C(O)C2O)C(O)C1O)CCCC(C)CCCC(C)C]

3.9 g (5.7 mmol) of D-Maltose octaacetate and 1.0 g (4.4 mol) of tetrahydrofarnesol was dissolved in dry acetonitrile (4 mL). 1.12 mL (8.83 mmol) of boron trifluoride diethyl etherate complex was added to the solution with cooling on ice. The reaction mixture was allowed to warm up slowly to room temperature while being stirred for 24 hours before addition of 1.8 mL (13 mmol) of triethylamine at 0° C. The resulting solution was diluted with ethyl acetate, and washed with water, 1M hydrochloric acid, saturated sodium bicarbonate aqueous solution, and saturated brine, successively, and dried over sodium sulfate. After filtration, the filtrate was concentrated to obtain 1-O-(3,7,11-trimethyldodec-2-enyl)-D-maltoside heptaacetate as a crude product.

The above obtained crude product of 1-O-(3,7,11-trimethyldodec-2-enyl)-D-maltoside heptaacetate was dissolved in methanol/tetrahydrofuran (1:1, 6 mL), and 0.45 mL (0.45 mmol) of 1M sodium methylate in methanol was added at room temperature. After being stirred for 24 hours, 33 μL (0.46 mmol) of acetyl chloride was added to the reaction mixture and the mixture was confirmed to be neutralized. The mixture was concentrated, and the resulting residue was purified by silica gel column chromatography (methanol/methylene chloride mixture) to obtain the title compound.

Example 161

Synthesis of
mono-O-(3,7,11-trimethyldodec-2-enyl)glycerol

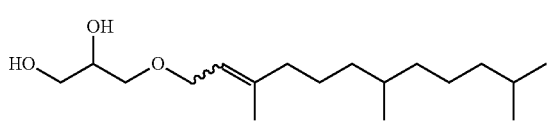 [SMILES: CC(=CCOCC(O)CO)CCCC(C)CCCC(C)C]

1.18 g (8.84 mmol) of N-chlorosuccinimide was suspended in methylene chloride (13 mL). After addition of 0.69 mL (9.3 mmol) of dimethylsulfide at 0° C., the solution was stirred for 20 min. After addition of 1.0 g (4.4 mmol) of tetrahydrofarnesol, the mixture was stirred for 1 hour at 0° C., with additional stirring for 6 hours at room temperature. After addition of saturated sodium bicarbonate aqueous solution, the reaction mixture was extracted with methylene chloride. The extract was washed with saturated brine, and dried over anhydrous sodium sulfate. After filtration, the filtrate was concentrated to obtain 3,7,11-trimethyldodec-2-ene-1-chloride as a crude product.

0.29 g (55%, 6.6 mmol) of sodium hydride was added to a solution of 0.61 g (6.6 mmol) of glycerol in dry N,N-dimethylformamide/tetrahydrofuran (1:1, 4 mL) at 0° C. with cooling on ice. After the mixture was stirred for 30 min at 50° C., the above 3,7,11-trimethyldodec-2-ene-1-chloride was added dropwise with additional stirring for 20 hours at the same temperature. After addition of water at 0° C., the reaction mixture was extracted with ether. The extract was washed with water, 1M hydrochloric acid, saturated sodium bicarbonate aqueous solution, and saturated brine, successively, and dried over anhydrous sodium sulfate. After filtration, the filtrate was concentrated, and the resulting residue was purified by silica gel column chromatography (ethyl acetate/hexane mixture) to obtain the title compound.

Example 162

Synthesis of
mono-O-(3,7,11-trimethyldodec-2-enyl)erythritol

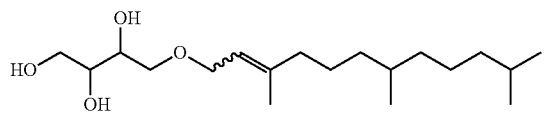 [SMILES: CC(=CCOCC(O)C(O)CO)CCCC(C)CCCC(C)C]

The title compound was synthesized using the same procedure as employed in Example 161, but with 0.81 g (6.6 mmol) of erythritol instead of glycerol.

Example 163

Synthesis of mono-O-(3,7,11-trimethyldodec-2-enyl) pentaerythritol

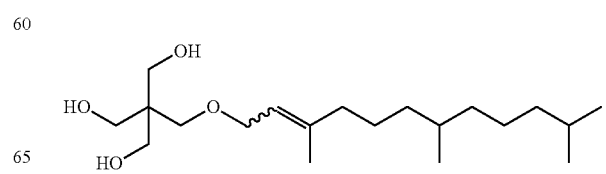

The title compound was synthesized using the same procedure as employed in Example 161, but with 0.90 g (6.6 mmol) of pentaerythritol instead of glycerol, having the following properties:

$^1$H-NMR spectrum (300 MHz, CDCl$_3$, TMS) δ: 0.80-0.90 (m, 9H), 1.00-1.60 (m, 12H), 1.65 and 1.74 (s, 3H, 3-CH$_3$), 1.95-2.05 (m, 2H), 2.87 (brs, 3H, OH), 3.45 (s, 2H), 3.72 (s, 6H), 3.97 (d, 0.1-7.3 Hz, 2H), 5.29 (t, J=7.3 Hz, 1H).

Example 164

Synthesis of mono-O-(3,7,11-trimethyldodec-2-enyl)diglycerol

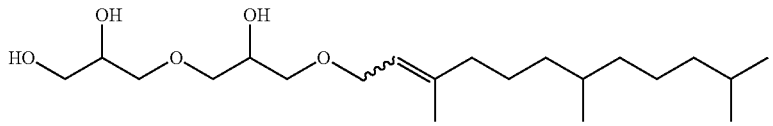 [SMILES: CC(=CCOCC(O)COCC(O)CO)CCCC(C)CCCC(C)C]

1.18 g (8.84 mmol) of N-Chlorosuccinimide was suspended in methylene chloride (13 mL). After addition of 0.69 mL (9.3 mmol) of dimethylsulfide at 0° C., the solution was stirred for 20 min. After addition of 1.0 g (4.4 mmol) of tetrahydrofarnesol, the mixture was stirred for 1 hour at 0° C., with additional stirring for 6 hours at room temperature. After addition of saturated sodium bicarbonate aqueous solution, the reaction mixture was extracted with methylene chloride. The extract was washed with saturated brine, and dried over anhydrous sodium sulfate. After filtration, the filtrate was concentrated to obtain 3,7,11-trimethyldodec-2-ene-1-chloride as a crude product.

0.29 g (55%, 6.6 mmol) of sodium hydride was added to a solution of 1.1 g (6.6 mmol) of diglycerol in dry N,N-dimethylformamide/tetrahydrofuran (1:1, 4 mL) with cooling on ice. After the mixture was stirred for 30 min at 50° C., the above 3,7,11-trimethyldodec-2-ene-1-chloride was added dropwise with additional stirring for 20 hours at the same temperature. After addition of water at 0° C., the reaction mixture was extracted with ether. The extract was washed with water, 1M hydrochloric acid, saturated sodium bicarbonate aqueous solution, and saturated brine, successively, and dried over anhydrous sodium sulfate. After filtration, the filtrate was concentrated, and the resulting residue was purified by silica gel column chromatography (methanol/methylene chloride mixture) to obtain the title compound.

Example 165

Synthesis of mono-O-(3,7,11-trimethyldodec-2-enyl)triglycerol

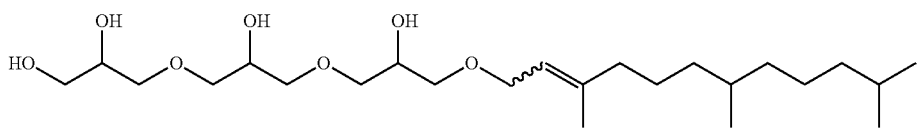 [SMILES: CC(=CCOCC(O)COCC(O)COCC(O)CO)CCCC(C)CCCC(C)C]

The title compound was synthesized using the same procedure as employed in Example 164, but with 1.6 g (6.6 mmol) of triglycerol instead of diglycerol.

Example 166

Synthesis of mono-O-(3,7,11-trimethyldodec-2-enyl)xylitol

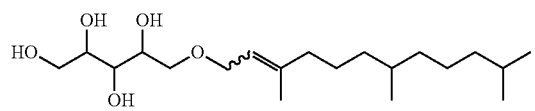 [SMILES: CC(=CCOCC(O)C(O)C(O)CO)CCCC(C)CCCC(C)C]

The title compound was synthesized using the same procedure as employed in Example 164, but with 1.0 g (6.6 mmol) of xylitol instead of diglycerol.

Example 167

Synthesis of mono-O-(3,7,11-trimethyldodec-2-enyl)mannitol]

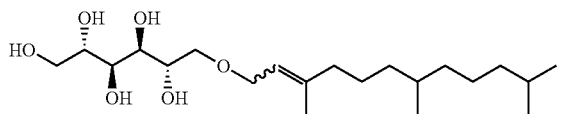 [SMILES: CC(=CCOC[C@H](O)[C@H](O)[C@@H](O)[C@@H](O)CO)CCCC(C)CCCC(C)C]

The title compound was synthesized using the same procedure as employed in Example 164, but with 1.2 g (6.6 mmol) of mannitol instead of diglycerol.

Example 168

Synthesis of mono-O-(3,7,11-trimethyldodec-2-enyl)sorbitol

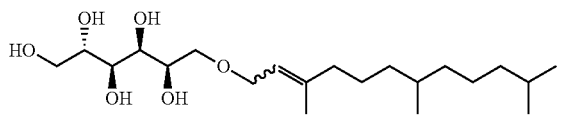 [SMILES: CC(=CCOC[C@@H](O)[C@H](O)[C@@H](O)[C@@H](O)CO)CCCC(C)CCCC(C)C]

The title compound was synthesized using the same procedure as employed in Example 164, but with 1.2 g (6.6 mmol) of sorbitol instead of diglycerol.

Example 169

Synthesis of mono-O-(3,7,11-trimethyldodec-2-enyl) dipentaerythritol

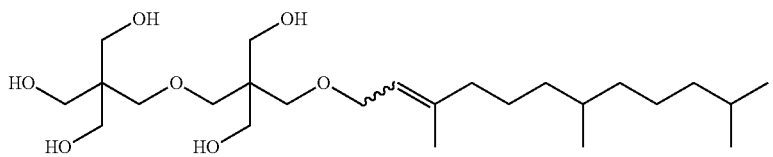 [SMILES: CC(=CCOCC(CO)(CO)COCC(CO)(CO)CO)CCCC(C)CCCC(C)C]

The title compound was synthesized using the same procedure as employed in Example 164, but with 1.7 g (6.6 mmol) of dipentaerythritol instead of diglycerol.

Example 170

Synthesis of mono-O-(3,7,11-trimethyldodec-2-enyl)ascorbic acid

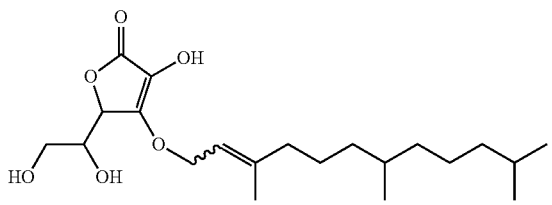 [SMILES: CC(=CCOC1=C(O)C(=O)OC1C(O)CO)CCCC(C)CCCC(C)C]

1.18 g (8.84 mmol) of N-Chlorosuccinimide was suspended in methylene chloride (13 mL). After addition of 0.69 mL (9.3 mmol) of dimethylsulfide at 0° C., the solution was stirred for 20 min. After addition of 1.0 g (4.4 mmol) of tetrahydrofarnesol, the mixture was stirred for 1 hour at 0° C., with additional stirring for 6 hours at room temperature. After addition of saturated sodium bicarbonate aqueous solution, the reaction mixture was extracted with methylene chloride. The extract was washed with saturated brine, and dried over anhydrous sodium sulfate. After filtration, the filtrate was concentrated to obtain 3,7,11-trimethyldodec-2-ene-1-chloride as a crude product.

0.66 mL (4.8 mmol) of triethylamine was added and dissolved in a suspension of 0.77 g (4.4 mmol) of ascorbic acid in acetonitrile (9 mL). After the above crude product of 3,7,11-trimethyldodec-2-ene-1-chloride was added at room temperature, the reaction mixture was heated for 2 hours at 90° C. The reaction mixture was concentrated, and resulting the residue was purified by silica gel column chromatography (methanol/methylene chloride mixture) to obtain the title compound.

Example 171

Formation of a liquid crystal by mono-O-(5,9,13,17-tetramethyloctadec-4-enoyl)glycerol and analysis thereof Mono-O-(5,9,13,17-tetramethyloctadec-4-enoyl)glycerol synthesized in Example 3 and water were homogeneously mixed in accordance with the same procedure as in Example 13 to obtain a sample of mono-O-(5,9,13,17-tetramethyloctadec-4-enoyl)glycerol/water system. SAXS analysis of the sample of mono-O-(5,9,13,17-tetramethyloctadec-4-enoyl)glycerol/water system was performed in the same manner as in Example 13. As a result, scattering peaks were observed. The peak value ratio exhibited the following ratio peculiar to the cubic liquid crystal belonging to the crystallographic space group Pn3m:

$$1:\sqrt{2}:\sqrt{3}:\sqrt{4}.$$

Thus, the sample of mono-O-(5,9,13,17-tetramethyloctadec-4-enoyl)glycerol/water system was confirmed to form a cubic liquid crystal that belong to the crystallographic space group Pn3m.

Example 172

Formation of a liquid crystal by mono-O-(5,9,13,17-tetramethyloctadec-4-enyl)diglycerol and analysis thereof Mono-O-(5,9,13,17-tetramethyloctadec-4-enyl)diglycerol synthesized in Example 32 and water were homogeneously mixed in accordance with the same procedure as in Example 13 to obtain a sample of mono-O-(5,9,13,17-tetramethyloctadec-4-enyl)diglycerol/water system. SAXS analysis of the sample of mono-O-(5,9,13,17-tetramethyloctadec-4-enyl)diglycerol/water system was performed in the same manner as in Example 13. As a result, scattering peaks were observed. The peak value ratio exhibited the following ratio peculiar to the cubic liquid crystal belonging to the crystallographic space group Pn3m:

$$\sqrt{2}:\sqrt{3}:\sqrt{4}.$$

Thus, the sample of mono-O-(5,9,13,17-tetramethyloctadec-4-enyl)diglycerol/water system was confirmed to form a cubic liquid crystal that belong to the crystallographic space group Pn3m.

Example 173

Formation of a liquid crystal by 1-O-(5,9,13-trimethyltetradec-4-enyl)-D-xylopyranoside and analysis thereof 1-O-(5,9,13-trimethyltetradec-4-enyl)-D-xylopyranoside synthesized in Example 103 and water were homogeneously mixed in accordance with the same procedure as in Example 13 to obtain a sample of 1-O-(5,9,13-trimethyltetradec-4-enyl)-D-xylopyranoside/water system. SAXS analysis of the sample of 1-O-(5,9,13-trimethyltetradec-4-enyl)-D-xylopyranoside/water system was performed in the same manner as in Example 13. As a result, scattering peaks were observed. The peak value ratio exhibited the following ratio peculiar to the cubic liquid crystal belonging to the crystallographic space group Pn3m:

$$\sqrt{2}:\sqrt{3}:\sqrt{4}.$$

Thus, the sample of 1-O-(5,9,13-trimethyltetradec-4-enyl)-D-xylopyranoside/water system was confirmed to form a cubic liquid crystal that belong to the crystallographic space group Pn3m.

Example 174

Formation of a liquid crystal by mono-O-(5,9,13-trimethyltetradec-4-enyl)glycerol and analysis thereof Mono-O-(5,9,13-trimethyltetradec-4-enyl)glycerol synthesized in Example 107 and water were homogeneously mixed in accordance with the same procedure as in Example 13 to obtain a sample of mono-O-(5,9,13-trimethyltetradec-4-enyl)glycerol/water system. SAXS analysis of the sample of mono-O-(5,9,13-trimethyltetradec-4-enyl)glycerol/water system was performed in the same manner as in Example 13. As a result, scattering peaks were observed. The peak value ratio exhibited the following ratio peculiar to the reverse hexagonal liquid crystal:

$1:\sqrt{3}:2.$

Thus, the sample of mono-O-(5,9,13-trimethyltetradec-4-enyl)glycerol/water system was confirmed to form a reverse hexagonal liquid crystal.

Example 175

Formation of a liquid crystal by mono-O-(4,8,12-trimethyltridec-3-enoyl)glycerol and analysis thereof Mono-O-(4,8,12-trimethyltridec-3-enoyl)glycerol synthesized in Example 120 and water were homogeneously mixed in accordance with the same procedure as in Example 13 to obtain a sample of mono-O-(4,8,12-trimethyltridec-3-enoyl)glycerol/water system. SAXS analysis of the sample of mono-O-(4,8,12-trimethyltridec-3-enoyl)glycerol/water system was performed in the same manner as in Example 13. As a result, scattering peaks were observed. The peak value ratio exhibited the following ratio peculiar to the cubic liquid crystal belonging to the crystallographic space group Pn3m:

$\sqrt{2}:\sqrt{3}:\sqrt{4}.$

Thus, the sample of mono-O-(4,8,12-trimethyltridec-3-enoyl)glycerol/water system was confirmed to form a cubic liquid crystal that belong to the crystallographic space group Pn3m.

Example 176

Formation of a liquid crystal by mono-O-(5,9,13-trimethyltetradec-4-enoyl)glycerol and analysis thereof Mono-O-(5,9,13-trimethyltetradec-4-enoyl)glycerol synthesized in Example 92 and water were homogeneously mixed in accordance with the same procedure as in Example 13 to obtain a sample of mono-O-(5,9,13-trimethyltetradec-4-enoyl)glycerol/water system. SAXS analysis of the sample of mono-O-(5,9,13-trimethyltetradec-4-enoyl)glycerol/water system was performed in the same manner as in Example 13. As a result, scattering peaks were observed. The peak value ratio exhibited the following ratio peculiar to the cubic liquid crystal belonging to the crystallographic space group Pn3m:

$\sqrt{2}:\sqrt{3}:\sqrt{4}.$ and the following ratio peculiar to the reverse hexagonal liquid crystal:

$1:\sqrt{3}:2.$

Thus, the sample of mono-O-(5,9,13-trimethyltetradec-4-enoyl)glycerol/water system was confirmed to form a mixture of a cubic liquid crystal that belong to the crystallographic space group Pn3m and a reverse hexagonal liquid crystal.

Example 177

Formation of a liquid crystal by mono-O-(5,9,13,17-tetramethyloctadec-4-enoyl)diglycerol and analysis thereof Mono-O-(5,9,13,17-tetramethyloctadec-4-enoyl)diglycerol synthesized in Example 4 and water were homogeneously mixed in accordance with the same procedure as in Example 13 to obtain a sample of mono-O-(5,9,13,17-tetramethyloctadec-4-enoyl)diglycerol/water system. SAXS analysis of the sample of mono-O-(5,9,13,17-tetramethyloctadec-4-enoyl)diglycerol/water system was performed in the same manner as in Example 13. As a result, scattering peaks were observed. The peak value ratio exhibited the following ratio peculiar to the reverse hexagonal liquid crystal:

$1:\sqrt{3}:2.$

Thus, the sample of mono-O-(5,9,13,17-tetramethyloctadec-4-enoyl)diglycerol/water system was confirmed to form a reverse hexagonal liquid crystal.

Example 178

Formation of a liquid crystal by mono-O-(3,7,11-trimethyldodec-2-enoyl)glycerol and analysis thereof Mono-O-(3,7,11-trimethyldodec-2-enoyl)glycerol synthesized in Example 146 and water were homogeneously mixed in accordance with the same procedure as in Example 13 to obtain a sample of mono-O-(3,7,11-trimethyldodec-2-enoyl)glycerol/water system. SAXS analysis of the sample of mono-O-(3,7,11-trimethyldodec-2-enoyl)glycerol/water system was performed in the same manner as in Example 13. As a result, scattering peaks were observed. The peak value ratio exhibited the following ratio peculiar to the cubic liquid crystal belonging to the crystallographic space group Pn3m:

$\sqrt{2}:\sqrt{3}:\sqrt{4}.$

Thus, the sample of mono-O-(3,7,11-trimethyldodec-2-enoyl)glycerol/water system was confirmed to form a cubic liquid crystal that belong to the crystallographic space group Pn3m.

Example 179

Viscosity Measurement of the Amphiphilic Compounds

The viscosities of the amphiphilic compounds synthesized above were measured at 25° C. and at a shear velocity of 105.7 $s^{-1}$ using a viscosity and viscoelasticity measuring apparatus MARS (Thermo Fisher Scientific). The representative results of the measurement are shown in Table 1.

TABLE 1

| Compound | Viscosity (Pas · sec) |
|---|---|
| Example 4 | 4.5 |
| Example 31 | 0.44 |
| Example 65 | 1.1 |
| Example 67 | 10.6 |
| Example 68 | 9.5 |
| Example 80 | 0.45 |
| Example 82 | 4.0 |
| Example 92 | 0.48 |
| Example 95 | 10.5 |
| Example 109 | 0.98 |
| Example 110 | 1.7 |
| Example 146 | 0.45 |
| Example 147 | 7.1 |
| Example 149 | 6.9 |
| Example 163 | 2.7 |
| Example 166 | 1.1 |

These results confirmed that the amphiphilic compounds of this invention had very low viscosities.

The invention claimed is:

1. An amphipathic compound having the following general formula (I):

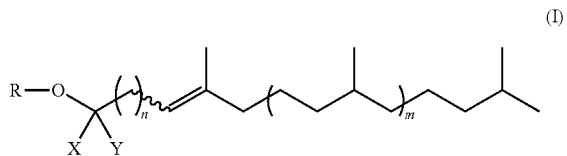

wherein
X and Y
 each denotes a hydrogen atom or together denote an oxygen atom,
n denotes the integer 1 or 2,
m denotes the integer 1 or 2, and
R denotes a hydrophilic group generated by removal of one hydroxyl group from any one selected from the group consisting of glycerol, erythritol, pentaerythritol, diglycerol, triglycerol, xylose, sorbitol, ascorbic acid, glucose, galactose, mannose, dipentaerythritol, maltose, mannitol, and xylitol.

2. The compound according to claim 1, which has viscosity of 11.0 Pa·s or less as determined at 25° C.

3. The compound according to claim 1, wherein the compound is selected from the group consisting of
mono-O-(5,9,13,17-tetramethyloctadec-4-enoyl)pentaerythritol,
mono-O-(5,9,13,17-tetramethyloctadec-4-enoyl)erythritol,
mono-O-(5,9,13,17-tetramethyloctadec-4-enoyl)glycerol,
mono-O-(5,9,13,17-tetramethyloctadec-4-enoyl)diglycerol,
1-O-(5,9,13,17-tetramethyloctadec-4-enyl)-D-xylopyranoside,
mono-O-(5,9,13,17-tetramethyloctadec-4-enyl)pentaerythritol,
mono-O-(5,9,13,17-tetramethyloctadec-4-enyl)glycerol,
mono-O-(5,9,13,17-tetramethyloctadec-4-enyl)erythritol,
mono-O-(5,9,13,17-tetramethyloctadec-4-enyl)diglycerol,
mono-O-(5,9,13-trimethyltetradec-4-enoyl)glycerol,
mono-O-(5,9,13-trimethyltetradec-4-enoyl)erythritol,
mono-O-(5,9,13-trimethyltetradec-4-enoyl)pentaerythritol,
mono-O-(5,9,13-trimethyltetradec-4-enoyl)diglycerol,
1-O-(5,9,13-trimethyltetradec-4-enyl)-D-xylopyranoside,
mono-O-(5,9,13-trimethyltetradec-4-enyl)glycerol,
mono-O-(5,9,13-trimethyltetradec-4-enyl)erythritol,
mono-O-(5,9,13-trimethyltetradec-4-enyl)pentaerythritol, and
mono-O-(5,9,13-trimethyltetradec-4-enyl)diglycerol.

4. A base for injection formulations, which comprises at least one type of the compound according to claim 1.

5. The base according to claim 4, which is a base for depot formulations.

6. A depot formulation, which comprises the base according to claim 5.

7. A composition comprising the compound according to claim 1 and an active ingredient.

8. The composition according to claim 7, wherein the composition further comprises an aqueous medium, and said amphipathic compound forms a non-lamellar liquid crystal in the composition.

9. A method for administering an active ingredient to a subject, comprising administering the composition according to claim 7, wherein said amphipathic compound forms a non-lamellar liquid crystal in a living body of a subject.

10. A method for administering an active ingredient to a subject, comprising administering the composition according to claim 8, wherein said amphipathic compound forms a non-lamellar liquid crystal in a living body of the subject.

* * * * *